(12) United States Patent
Hong et al.

(10) Patent No.: US 8,569,340 B2
(45) Date of Patent: *Oct. 29, 2013

(54) AMPK-ACTIVATING PIPERIDINYLOXYPYIRIDINE CARBOXAMIDE AND SULFONAMIDE COMPOUNDS AND METHODS FOR USING THE SAME

(75) Inventors: Hui Hong, Palo Alto, CA (US); Xiang Xu, Foster City, CA (US); Jiaxin Yu, San Carlos, CA (US); Rajinder Singh, Belmont, CA (US); Ihab S. Darwish, San Carlos, CA (US); Sambaiah Thota, Fremont, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/348,380

(22) Filed: Jan. 11, 2012

(65) Prior Publication Data
US 2012/0115838 A1 May 10, 2012

Related U.S. Application Data

(63) Continuation of application No. 12/272,581, filed on Nov. 17, 2008, now Pat. No. 8,119,809.

(60) Provisional application No. 60/988,721, filed on Nov. 16, 2007, provisional application No. 60/990,554, filed on Nov. 27, 2007, provisional application No. 60/990,558, filed on Nov. 27, 2007, provisional application No. 60/991,189, filed on Nov. 29, 2007, provisional application No. 61/013,924, filed on Dec. 14, 2007.

(51) Int. Cl.
*A61K 31/445* (2006.01)
*C07D 401/12* (2006.01)

(52) U.S. Cl.
USPC ............ 514/316; 546/187; 546/191; 546/194

(58) Field of Classification Search
USPC .......................... 514/316; 546/187, 191, 194
See application file for complete search history.

(56) References Cited

U.S. PATENT DOCUMENTS

| | | | |
|---|---|---|---|
| 4,987,141 A | 1/1991 | Bushell et al. | |
| 6,172,232 B1 | 1/2001 | Stahrfeldt | |
| 6,472,405 B1 | 10/2002 | Fisher et al. | |
| 7,001,900 B2 | 2/2006 | Jacobsen et al. | |
| 7,208,491 B2 | 4/2007 | Fertig et al. | |
| 7,253,286 B2 | 8/2007 | Funahashi et al. | |
| 7,273,868 B2 | 9/2007 | Yamada et al. | |
| 8,012,955 B2 * | 9/2011 | Singh et al. | 514/210.07 |
| 2002/0183327 A1 | 12/2002 | Gerlach et al. | |
| 2004/0002513 A1 | 1/2004 | Mazurov et al. | |
| 2004/0023972 A1 | 2/2004 | Sundermann et al. | |
| 2005/0165049 A1 | 7/2005 | Hulme et al. | |
| 2005/0282864 A1 | 12/2005 | McArthur et al. | |
| 2007/0123515 A1 | 5/2007 | Nettekoven et al. | |
| 2007/0123525 A1 | 5/2007 | Nettekoven et al. | |
| 2007/0123526 A1 | 5/2007 | Nettekoven et al. | |

FOREIGN PATENT DOCUMENTS

| | | |
|---|---|---|
| EP | 1813613 | 8/2007 |
| GB | 2 327 675 | 3/1999 |
| WO | WO9736903 | 10/1997 |
| WO | WO0012074 | 3/2000 |
| WO | WO0059904 | 10/2000 |
| WO | WO0164639 | 9/2001 |
| WO | WO0200651 | 1/2002 |
| WO | WO02089749 | 11/2002 |
| WO | WO03018586 | 3/2003 |
| WO | WO03022856 | 3/2003 |
| WO | WO03070732 | 8/2003 |
| WO | WO03072578 | 9/2003 |
| WO | WO2004000820 | 12/2003 |
| WO | WO2004054974 | 7/2004 |
| WO | WO2004085409 | 10/2004 |
| WO | WO2004111003 | 12/2004 |
| WO | WO2005002552 | 1/2005 |
| WO | WO2005020921 | 3/2005 |
| WO | WO2005061442 | 7/2005 |
| WO | WO2005116000 | 12/2005 |

(Continued)

OTHER PUBLICATIONS

Beurner et al. "Expedient synthesis . . . " J. Org, Chem. 74, 789-794 2009).*
Patani et al. "Bioisosterism . . . " Chem. Rev. 96, p. 3147-3176 (1996).*
Zhao et al. "Discovery and SAR . . . " Bioorg, Med. Chem. Lett v,17, p. 3254-3257 (2007).*
Copending U.S. Appl. No. 11/963,742, filed Dec. 21, 2007.
Copending U.S. Appl. No. 12/334,201, filed Dec. 12, 2008.
Copending U.S. Appl. No. 12/428,334, filed Apr. 22, 2009.
International Search Report and Written Opinion in PCT/US2008/083801, (May 18, 2010).
CAS Registry Nos. 896885-08-8; 896884-87-0; 896870-69-2; and 896870-65-8, report generated Dec. 10, 2007.

(Continued)

*Primary Examiner* — Celia Chang
(74) *Attorney, Agent, or Firm* — Travis Young; McDonnell Boehnen Hulbert & Berghoff LLP

(57) ABSTRACT

Disclosed are carboxamide, sulfonamide and amine compounds, as well as pharmaceutical compositions and methods of use. One embodiment is a compound having the structure

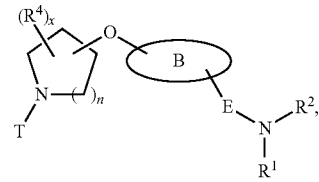

in which $R^1$, $R^2$, $R^4$, E, T, n and x are as described herein. In certain embodiments, a compound disclosed herein activates the AMPK pathway, and can be used to treat metabolism-related disorders and conditions.

27 Claims, No Drawings

(56) References Cited

FOREIGN PATENT DOCUMENTS

| | | |
|---|---|---|
| WO | WO2005117865 | 12/2005 |
| WO | WO2006045416 | 5/2006 |
| WO | WO2006046916 | 5/2006 |
| WO | WO2006058905 | 6/2006 |
| WO | WO2006064355 | 6/2006 |
| WO | WO2006067462 | 6/2006 |
| WO | WO2006076131 | 7/2006 |
| WO | WO2006094235 | 9/2006 |
| WO | WO2006099379 | 9/2006 |
| WO | WO2006101434 | 9/2006 |
| WO | WO2006114313 | 11/2006 |
| WO | WO2007005951 | 1/2007 |
| WO | WO2007075688 | 7/2007 |
| WO | WO2007087548 | 8/2007 |
| WO | WO2007087549 | 8/2007 |
| WO | WO2007098086 | 8/2007 |
| WO | WO2007099423 | 9/2007 |
| WO | WO2007122482 | 11/2007 |
| WO | WO2007143823 | 12/2007 |
| WO | WO2007143824 | 12/2007 |
| WO | WO2008017685 | 2/2008 |
| WO | WO2008083124 | 7/2008 |
| WO | WO2008133975 | 11/2008 |

OTHER PUBLICATIONS

CAS Registry Nos. 894782-16-2; 894780-97-3; 894780-86-0; 894780-85-9; 894780-83-7; and 894779-82-9, report generated Dec. 10, 2007.

CAS Registry Nos. 197893-73-5; 197893-70-2; 197893-61-1; 197892-93-6; 197890-89-4; 197890-86-1; 197890-77-0, report generated Dec. 10, 2007.

CAS Registry Nos. 197893-74-6 and 197890-90-7, report generated Dec. 10, 2007.

\* cited by examiner

AMPK-ACTIVATING PIPERIDINYLOXYPYRIDINE CARBOXAMIDE AND SULFONAMIDE COMPOUNDS AND METHODS FOR USING THE SAME

CROSS-REFERENCE TO RELATED APPLICATIONS

This application is a continuation of U.S. patent application Ser. No. 12/272,581, filed Nov. 17, 2008, which claims the benefit of the earlier filing dates of U.S. Provisional Patent Application Ser. No. 60/988,721, filed Nov. 16, 2007; Ser. No. 60/990,554, filed Nov. 27, 2007; Ser. No. 60/990,558, filed Nov. 27, 2007; Ser. No. 60/991,189, filed Nov. 29, 2007; and Ser. No. 61/013,924, filed Dec. 14, 2007. Each application referenced in this paragraph is hereby incorporated herein by reference in its entirety.

BACKGROUND

1. Field

This disclosure relates generally to compounds, pharmaceutical compositions and methods of use of the compounds and compositions containing them. This disclosure relates more particularly to certain carboxamide, sulfonamide and amine compounds and pharmaceutical compositions thereof, and to methods of treating and preventing metabolic disorders such as type II diabetes, atherosclerosis and cardiovascular disease using certain carboxamide, sulfonamide and amine compounds.

2. Technical Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptor-γ, increase endogenous adiponectin production in humans.

Adiponectin binds its receptors in liver and skeletal muscle and thereby activates the 5'-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis. What is needed are compounds, pharmaceutical compositions and methods of using them to treat disease states associated with circulating adiponectin levels, such as type II diabetes, atherosclerosis and cardiovascular disease.

SUMMARY

Disclosed herein are compounds having structural formula (I)

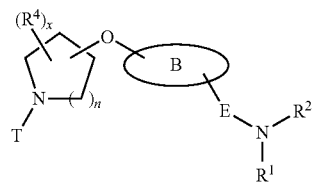

or a pharmaceutically acceptable salt, prodrug, solvate, hydrate, or N-oxide thereof, wherein "B" represents -(aryl or heteroaryl)-substituted by w $R^3$ and k $R^{14}$;

E is —C(O)—, —S(O)$_2$— or a single bond;

$R^1$ is H, —(C$_1$-C$_4$ alkyl) or —C(O)O—(C$_1$-C$_4$ alkyl);

$R^2$ is -Hca, -Cak-N($R^9$)-G-$R^{22}$ or —(C$_2$-C$_8$ alkyl)-N($R^9$)—$R^{24}$ in which one or two carbons of the (C$_2$-C$_8$ alkyl) are optionally replaced by —O—, —S— or —N($R^9$)— and $R^{24}$ is —$R^{23}$, -G-$R^{23}$, or —C(O)O—(C$_1$-C$_6$ alkyl);

each $R^3$ is substituted on a benzo or pyrido carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0\text{-}2}$R$^{10}$, -halogen, —NO$_2$ and —CN;

w is 0, 1, 2 or 3;

each $R^{14}$ is substituted on a non-benzo, non pyrido carbon of the ring system denoted by "B", and is independently selected from —(C$_1$-C$_6$ alkyl), —(C$_1$-C$_6$ halooalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0\text{-}2}$R$^{10}$, -halogen, —NO$_2$ and —CN;

k is 0, 1 or 2;

each $R^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0\text{-}2}$R$^{10}$, -halogen, —NO$_2$ and —CN, and two $R^4$ on the same carbon optionally combine to form oxo;

x is 0, 1, 2, 3 or 4;

n is 0, 1, 2 or 3;

T is —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0\text{-}2}$R$^{10}$ or

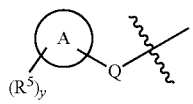

in which
- Q is —(C$_0$-C$_3$ alkyl)-, in which each carbon of the —(C$_0$-C$_3$ alkyl)- is optionally and independently substituted with one or two R$^{16}$, or —S(O)$_2$—;
- the ring system denoted by "A" is heteroaryl, aryl, cycloalkyl or heterocycloalkyl;
- each R$^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN; and
- y is 0, 1, 2, 3 or 4;

in which
- each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O—, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—,
- each R$^6$, R$^7$, R$^8$ and R$^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl),
- each R$^9$ is independently selected from —H, —(C$_1$-C$_4$ alkyl) and —C(O)O—(C$_1$-C$_4$ alkyl),
- each G is independently —(C$_0$-C$_3$ alkyl)-, in which each carbon of the —(C$_0$-C$_3$ alkyl)- is optionally and independently substituted with one or two R$^{16}$, or —S(O)$_2$—,
- each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo,
- each R$^{20}$, R$^{22}$ and R$^{23}$ is independently Ar or Het,
- each Ar is an optionally substituted aryl,
- each Het is an optionally substituted heteroaryl,
- each Cak is an optionally substituted cycloalkyl,
- each Hca is an optionally substituted heterocycloalkyl, and
- each alkyl is optionally substituted.

Also disclosed herein are pharmaceutical compositions. Examples of such compositions include those having at least one pharmaceutically acceptable carrier, diluent or excipient; and a compound, pharmaceutically acceptable salt, prodrug, solvate, hydrate or N-oxide described above.

Another aspect of the present disclosure includes methods for modulating metabolism in subjects. Accordingly, also disclosed are methods for treating metabolic disorders using the presently disclosed compounds and pharmaceutical compositions.

DETAILED DESCRIPTION

One aspect of the disclosure provides compounds having structural formula (I):

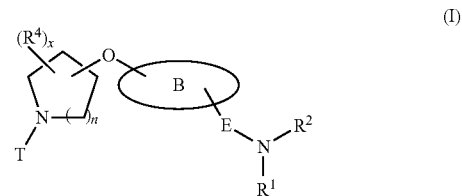

and pharmaceutically acceptable salts, prodrugs, solvates, hydrates, and N-oxides thereof, in which
- "B" represents -(aryl or heteroaryl)-substituted by w R$^3$ and k R$^{14}$;
- E is —C(O)—, —S(O)$_2$— or a single bond, provided that when "B" is phenyl, E is not —C(O)—;
- R$^1$ is H, —(C$_1$-C$_4$ alkyl) or —C(O)O—(C$_1$-C$_4$ alkyl);
- R$^2$ is -Hca, -Cak-N(R$^9$)-G-R$^{22}$ or —(C$_2$-C$_8$ alkyl)-N(R$^9$)—R$^{24}$ in which one or two carbons of the (C$_2$-C$_8$ alkyl) are optionally replaced by —O—, —S— or —N(R$^9$)— and R$^{24}$ is —R$^{23}$, -G-R$^{23}$, or —C(O)O—(C$_1$-C$_6$ alkyl);
- each R$^3$ is substituted on a benzo or pyrido carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;
- w is 0, 1, 2 or 3;
- each R$^{14}$ is substituted on a non-benzo, non-pyrido carbon of the ring system denoted by "B", and is independently selected from —(C$_1$-C$_6$ alkyl), —(C$_1$-C$_6$ halooalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;
- k is 0, 1 or 2;
- each R$^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;
- x is 0, 1, 2, 3 or 4;
- n is 0, 1, 2 or 3;
- T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

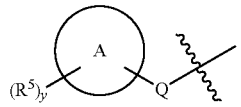

in which
- Q is —(C$_0$-C$_3$ alkyl)-, in which each carbon of the —(C$_0$-C$_3$ alkyl)- is optionally and independently substituted with one or two R$^{16}$, or —S(O)$_2$—;
- the ring system denoted by "A" is heteroaryl, aryl, cycloalkyl or heterocycloalkyl;
- each R$^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, —(C$_0$-C$_6$ alkyl)-C(O)R$^{10}$, -halogen, —NO$_2$ and —CN; and
- y is 0, 1, 2, 3 or 4;

in which
- each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—,
- each R$^6$, R$^7$, R$^8$ and R$^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl),
- each R$^9$ is independently selected from —H, —(C$_1$-C$_4$ alkyl) and —C(O)O—(C$_1$-C$_4$ alkyl),
- each G is independently —(C$_0$-C$_3$ alkyl)-, in which each carbon of the —(C$_0$-C$_3$ alkyl)- is optionally and independently substituted with one or two R$^{16}$, or —S(O)$_2$—,
- each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo,
- each R$^{20}$, R$^{22}$ and R$^{23}$ is independently Ar or Het,
- each Ar is an optionally substituted aryl,
- each Het is an optionally substituted heteroaryl,
- each Cak is an optionally substituted cycloalkyl,
- each Hca is an optionally substituted heterocycloalkyl, and
- each alkyl is optionally substituted.

In certain embodiments of the presently disclosed compounds of structural formula (I), the ring system denoted by "B" is

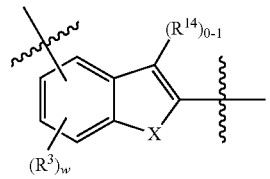

in which X is O or S, and E is —C(O)—. In certain such embodiments, one R$^{14}$ can be substituted on the furano or thieno carbon. In one such embodiment, R$^{14}$ is selected from —(C$_1$-C$_6$ alkyl), —(C$_1$-C$_6$ haloalkyl) (e.g., trifluoromethyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, R$^{14}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. R$^{14}$ can be, for example, halo (e.g., —Cl or —F), cyano, unsubstituted —(C$_1$-C$_4$ alkyl) (e.g., methyl or ethyl), or unsubstituted —(C$_1$-C$_4$ haloakyl) (e.g., trifluoromethyl). In certain embodiments, R$^{14}$ is H or methyl; in others, R$^{14}$ is halo (e.g., Cl). In other embodiments, no R$^{14}$ is substituted on the furano or thieno carbon.

In one embodiment, X is O.

In certain embodiments of the presently disclosed compounds of structural formula (I), the ring system denoted by "B" is

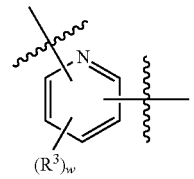

and E is —C(O)— or —S(O)$_2$—.

In certain embodiments of the presently disclosed compounds of structural formula (I), the ring system denoted by "B" is

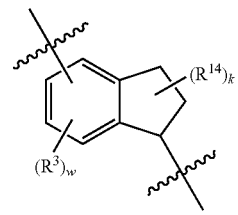

and E is a single bond. In one embodiment, k is 0. In another embodiment, k is 1 or 2. In certain embodiments, In each $R^{14}$ is independently selected from —$(C_1-C_6$ alkyl), —$(C_1-C_6$ haloalkyl) (e.g., trifluoromethyl), —$(C_0-C_6$ alkyl)-L-$R^7$, —$(C_0-C_6$ alkyl)-$NR^8R^9$, —$(C_0-C_6$ alkyl)-$OR^{10}$, —$(C_0-C_6$ alkyl)-$C(O)R^{10}$, —$(C_0-C_6$ alkyl)-$S(O)_{0-2}R^{10}$, -halogen, —$NO_2$ and —CN, in which each $R^7$, $R^8$ and $R^{10}$ is independently selected from H, —$(C_1-C_6$ alkyl), —$(C_1-C_6$ haloalkyl), —$(C_0-C_6$ alkyl)-L-$(C_0-C_6$ alkyl), —$(C_0-C_6$ alkyl)-$NR^9(C_0-C_6$ alkyl), —$(C_0-C_6$ alkyl)-O—$(C_0-C_6$ alkyl), —$(C_0-C_6$ alkyl)-C(O)—$(C_0-C_6$ alkyl), and —$(C_0-C_6$ alkyl)-$S(O)_{0-2}$—$(C_0-C_6$ alkyl), and in which no alkyl or haloalkyl is substituted with an aryl-, heteroaryl-, cycloalkyl- or heterocycloalkyl-containing group. For example, in one embodiment, each $R^{14}$ is independently selected from —$(C_1-C_3$ alkyl), —$(C_1-C_3$ haloalkyl), —$(C_0-C_3$ alkyl)-L-$R^7$, —$(C_0-C_3$ alkyl)-$NR^8R^9$, —$(C_0-C_3$ alkyl)-$OR^{10}$, —$(C_0-C_3$ alkyl)-$C(O)R^{10}$, —$(C_0-C_3$ alkyl)-$S(O)_{0-2}R^{10}$, -halogen, —$NO_2$ and —CN, in which each $R^7$, $R^8$ and $R^{10}$ is independently selected from H, —$(C_1-C_2$ alkyl), —$(C_1-C_2$ haloalkyl), —$(C_0-C_2$ alkyl)-L-$(C_0-C_2$ alkyl), —$(C_0-C_2$ alkyl)-$NR^9(C_0-C_2$ alkyl), —$(C_0-C_2$ alkyl)-O—$(C_0-C_2$ alkyl), —$(C_0-C_2$ alkyl)-C(O)—$(C_0-C_2$ alkyl) and —$(C_0-C_2$ alkyl)-$S(O)_{0-2}$—$(C_0-C_2$ alkyl), and in which no alkyl or haloalkyl is substituted with an aryl-, heteroaryl-, cycloalkyl- or heterocycloalkyl-containing group. Each $R^{14}$ can be, for example, halo (e.g., —Cl or —F), cyano unsubstituted —$(C_1-C_4$ alkyl) (e.g., methyl or ethyl) or unsubstituted —$(C_1-C_4$ haloakyl) (e.g., trifluoromethyl).

In certain embodiments of the presently disclosed compounds of structural formula (I), T is

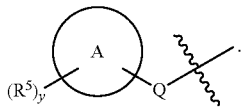

In such embodiments, Q is —$S(O)_2$— or —$(C_0-C_3$ alkyl)- in which each carbon of the $(C_0-C_3$ alkyl) is optionally and independently substituted with one or two $R^{16}$, in which each $R^{16}$ is independently selected from —$(C_1-C_6$ alkyl), —$(C_1-C_6$ haloalkyl), —$(C_0-C_6$ alkyl)-Ar, —$(C_0-C_6$ alkyl)-Het, —$(C_0-C_6$ alkyl)-Cak, —$(C_0-C_6$ alkyl)-Hca, —$(C_0-C_6$ alkyl)-L-$R^7$, —$(C_0-C_6$ alkyl)-$NR^8R^9$, —$(C_0-C_6$ alkyl)-$OR^{10}$, —$(C_0-C_6$ alkyl)-$C(O)R^{10}$, —$(C_0-C_6$ alkyl)-$S(O)_{0-2}R^{10}$, -halogen, —$NO_2$ and —CN, and optionally two of $R^{16}$ on the same carbon combine to form oxo. In certain embodiments, each $R^{16}$ is independently selected from —$(C_1-C_6$ alkyl), —$(C_1-C_6$ haloalkyl) (e.g., trifluoromethyl), —$(C_0-C_6$ alkyl)-L-$R^7$, —$(C_0-C_6$ alkyl)-$NR^8R^9$, —$(C_0-C_6$ alkyl)-$OR^{10}$, —$(C_0-C_6$ alkyl)-$C(O)R^{10}$, —$(C_0-C_6$ alkyl)-$S(O)_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —$(C_1-C_6$ alkyl), —$(C_1-C_6$ haloalkyl), —$(C_0-C_6$ alkyl)-L-$(C_0-C_6$ alkyl), —$(C_0-C_6$ alkyl)-$NR^9(C_0-C_6$ alkyl), —$(C_0-C_6$ alkyl)-O—$(C_0-C_6$ alkyl), —$(C_0-C_6$ alkyl)-C(O)—$(C_0-C_6$ alkyl), and —$(C_0-C_6$ alkyl)-$S(O)_{0-2}$—$(C_0-C_6$ alkyl), and in which no alkyl or haloalkyl is substituted with an aryl-, heteroaryl-, cycloalkyl- or heterocycloalkyl-containing group. For example, in particular compounds, each $R^{16}$ is —$(C_1-C_3$ alkyl), —$(C_1-C_3$ haloalkyl), —$(C_0-C_3$ alkyl)-L-$R^7$, —$(C_0-C_3$ alkyl)-$NR^8R^9$, —$(C_0-C_3$ alkyl)-$OR^{10}$, —$(C_0-C_3$ alkyl)-$C(O)R^{10}$, —$(C_0-C_3$ alkyl)-$S(O)_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —$(C_1-C_2$ alkyl), —$(C_1-C_2$ haloalkyl), —$(C_0-C_2$ alkyl)-L-$(C_0-C_2$ alkyl), —$(C_0-C_2$ alkyl)-$NR^9(C_0-C_2$ alkyl), —$(C_0-C_2$ alkyl)-O—$(C_0-C_2$ alkyl), —$(C_0-C_2$ alkyl)-C(O)—$(C_0-C_2$ alkyl) and —$(C_0-C_2$ alkyl)-$S(O)_{0-2}$—$(C_0-C_2$ alkyl), and in which no alkyl or haloalkyl is substituted with an aryl-, heteroaryl-, cycloalkyl- or heterocycloalkyl-containing group. In certain embodiments, Q has at most one $R^{16}$ or an oxo substituted thereon. Q can be, for example, an unsubstituted —$(C_0-C_3$ alkyl)-. In other embodiments, Q is a $(C_1-C_3$ alkyl) having as its only substitution a single oxo group. For example, in certain embodiments, Q is —$CH_2$—; a single bond; —$S(O)_2$—; —C(O)—; or —$CH(CH_3)$—.

In certain embodiments, the

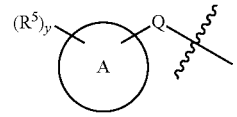

moiety is

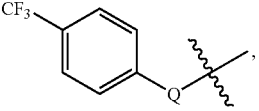

for example, p-(trifluoromethyl)phenyl. In other embodiments, the

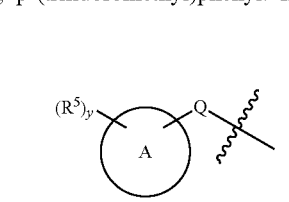

moiety is

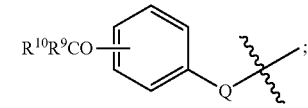

in one such embodiment, Q is a single bond.

The number of substituents on the ring system denoted by "A", y, is 0, 1, 2, 3 or 4. For example, in some embodiments, y is 0, 1, 2 or 3, for example 1. In one embodiment, y is not zero and at least one $R^5$ is halo, cyano, —$(C_1-C_4$ haloalkyl), —O—$(C_1-C_4$ haloalkyl), —$(C_1-C_4$ alkyl), —O—$(C_1-C_4$ alkyl), —C(O)—$(C_0-C_4$ alkyl), —C(O)O—$(C_0-C_4$ alkyl), —C(O)N($C_0-C_4$ alkyl)($C_0-C_4$ alkyl), $NO_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group.

In certain embodiments of the presently disclosed compounds of structural formula (I), each $R^5$ is independently selected from —$(C_1-C_6$ alkyl), —$(C_1-C_6$ haloalkyl) (e.g., trifluoromethyl), —$(C_0-C_6$ alkyl)-L-$R^7$, —$(C_0-C_6$ alkyl)-$NR^8R^9$, —$(C_0-C_6$ alkyl)-$OR^{10}$, —$(C_0-C_6$ alkyl)-$C(O)R^{10}$, —$(C_0-C_6$ alkyl)-$S(O)_{0-2}R^{10}$, -halogen, —$NO_2$ and —CN, in which each $R^7$, $R^8$ and $R^{10}$ is independently selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^5$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group.

In one embodiment of the compounds of structural formula (I), y is 0.

In the presently disclosed compounds, the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —(C$_0$-C$_3$ alkyl)- optionally substituted with oxo, and optionally substituted with one or more R$^{16}$. For example, Q can be a —(C$_1$-C$_3$ alkyl)- having its only substitution a single oxo, or an unsubstituted —(C$_0$-C$_3$ alkyl)-. For example, in certain embodiments, Q is —CH$_2$—; a single bond; —S(O)$_2$—; —C(O)—; or —CH(CH$_3$)—.

For example, in certain embodiments of the presently disclosed compounds, the ring system denoted by "A" is a phenyl. In one embodiment, y is 1 and R$^5$ is attached to the phenyl para to Q. In another embodiment, y is 1 and R$^5$ is selected from the group consisting of halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, and in which no (C$_0$-C$_4$ alkyl) or (C$_1$-C$_4$ alkyl) is substituted by an aryl, heteroaryl, cycloalkyl or heterocycloalkyl-containing group. R$^5$ can be, for example, —Cl, —F, cyano, —C(O)CH$_3$, —C(O)OH, —C(O)NH$_2$, trifluoromethyl, difluoromethyl, difluoromethoxy or trifluoromethoxy. In another embodiment, the

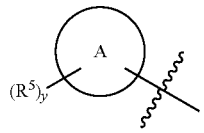

moiety is a 3,4-dihalophenyl.

In another embodiment of the presently disclosed compounds of structural formula (I), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —(C$_0$-C$_3$ alkyl)- optionally substituted with oxo, and optionally substituted with one or more R$^{16}$. For example, Q can be a —(C$_1$-C$_3$ alkyl)- having its only substitution a single oxo, or an unsubstituted —(C$_0$-C$_3$ alkyl)-. In certain embodiments, Q is —CH$_2$—; a single bond; —S(O)$_2$—; —C(O)—; or —CH(CH$_3$)—.

In one embodiment of the presently disclosed compounds, the compound has structural formula (II):

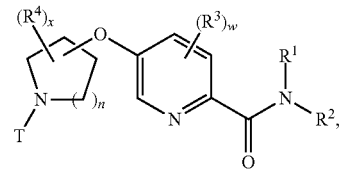

(II)

in which the variables are defined as described above with reference to structural formula (I).

In another embodiment of the presently disclosed compounds, the compound has structural formula (III):

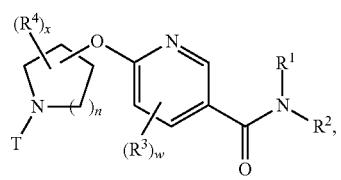

(III)

in which the variables are defined as described above with reference to structural formula (I).

In another embodiment of the presently disclosed compounds, the compound has structural formula (IV):

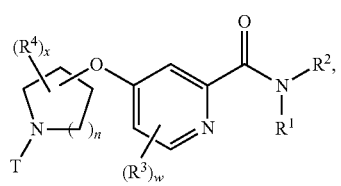

(IV)

in which the variables are defined as described above with reference to structural formula (I).

In another embodiment of the presently disclosed compounds, the compound has structural formula (V):

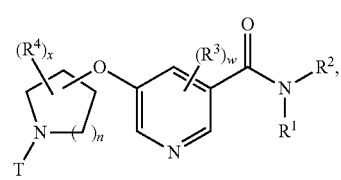

(V)

in which the variables are defined as described above with reference to structural formula (I).

In another embodiment of the presently disclosed compounds, the compound has structural formula (VI):

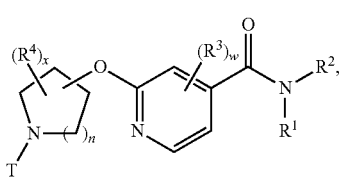

(VI)

in which the variables are defined as described above with reference to structural formula (I).

In another embodiment of the presently disclosed compounds, the compound has structural formula (VII):

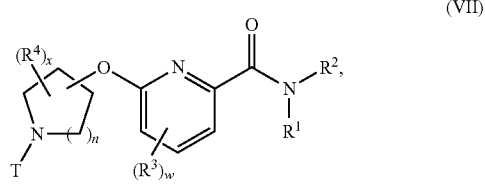

(VII)

in which the variables are defined as described above with reference to structural formula (I).

In another embodiment of the presently disclosed compounds, the compound has structural formula (VIII):

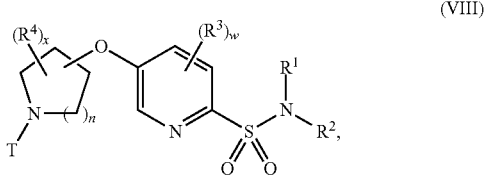

(VIII)

in which the variables are defined as described above with reference to structural formula (I).

In another embodiment of the presently disclosed compounds, the compound has structural formula (IX):

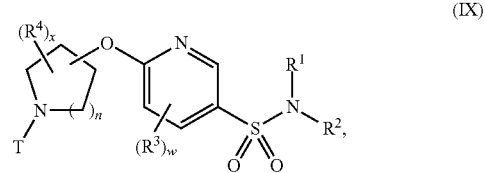

(IX)

in which the variables are defined as described above with reference to structural formula (I).

In another embodiment of the presently disclosed compounds, the compound has the structural formula (X):

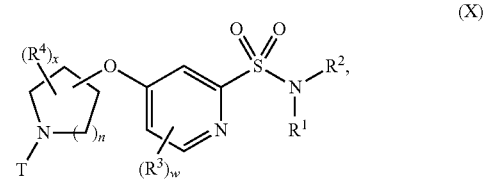

(X)

in which the variables are defined as described above with reference to structural formula (I).

In another embodiment of the presently disclosed compounds, the compound has structural formula (XI):

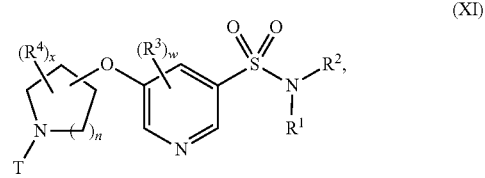

(XI)

in which the variables are defined as described above with reference to structural formula (I).

In another embodiment of the presently disclosed compounds, the compound has structural formula (XII):

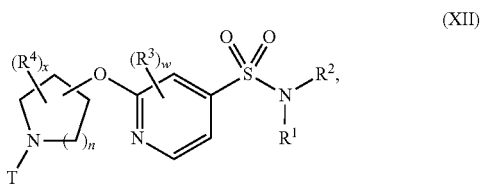

(XII)

in which the variables are defined as described above with reference to structural formula (I).

In another embodiment of the presently disclosed compounds, the compound has structural formula (XIII):

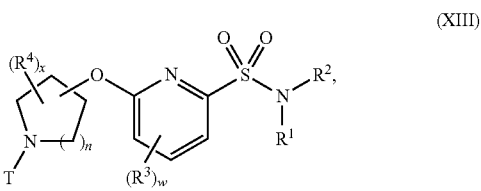

(XIII)

in which the variables are defined as described above with reference to structural formula (I).

In one embodiment of the presently disclosed compounds, the compound has structural formula (XIV):

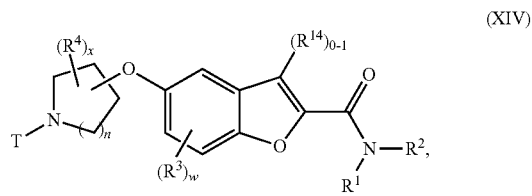

(XIV)

in which the variables are defined as described above with reference to structural formula (I). In certain embodiments, one $R^{14}$ is substituted on the furano carbon. In other embodiments, no $R^{14}$ is substituted on the furano carbon.

In another embodiment of the presently disclosed compounds, the compound has structural formula (XV):

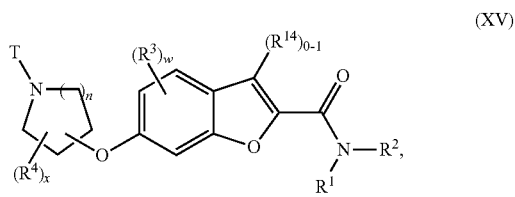

(XV)

in which the variables are defined as described above with reference to structural formula (I). In certain embodiments, one $R^{14}$ is substituted on the furano carbon. In other embodiments, no $R^{14}$ is substituted on the furano carbon.

In one embodiment of the presently disclosed compounds, the compound has structural formula (XVI):

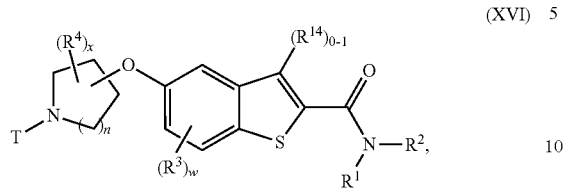

(XVI)

in which the variables are defined as described above with reference to structural formula (I). In certain embodiments, one $R^{14}$ is substituted on the thieno carbon. In other embodiments, no $R^{14}$ is substituted on the thieno carbon.

In another embodiment of the presently disclosed compounds, the compound has structural formula (XVII):

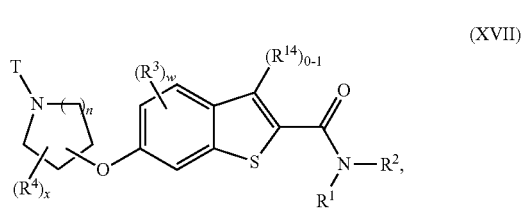

(XVII)

in which the variables are defined as described above with reference to structural formula (I). In certain embodiments, one $R^{14}$ is substituted on the thieno carbon. In other embodiments, no $R^{14}$ is substituted on the thieno carbon.

The presently disclosed compounds include S-oxidized forms of the benzothiophene compounds described (e.g., with reference to structural formulae (XVI) and (XVII). S-oxides include, for example, sulfoxides (—SO—) and sulfones (—SO$_2$—). Such compounds may be oxidized chemically or upon administration to e.g. a human subject, may be oxidized biologically. Chemically oxidized compounds may also be biologically reduced to the benzothiophene form.

In one embodiment of the presently disclosed compounds, the compound has structural formula (XVIII):

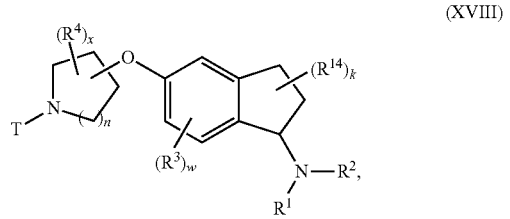

(XVIII)

in which the variables are defined as described above with reference to structural formula (I).

In another embodiment of the presently disclosed compounds, the compound has structural formula (XIX):

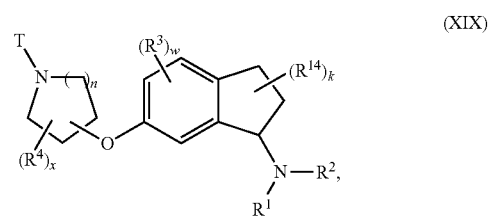

(XIX)

in which the variables are defined as described above with reference to structural formula (I).

In certain embodiments of the compounds disclosed with respect to structural formulae (I)-(XIX), n is 1 or 2. For example, in one embodiment, n is 2. In another embodiment, n is 1.

In one embodiment of the presently disclosed compounds, the compound has the structural formula (XX):

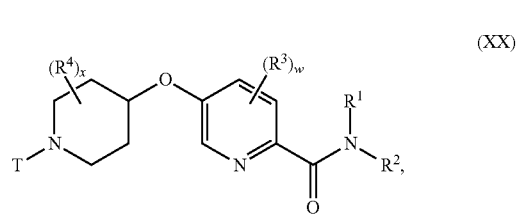

(XX)

in which the variables are defined as described above with reference to structural formula (I).

In another embodiment of the presently disclosed compounds, the compound has structural formula (XXI):

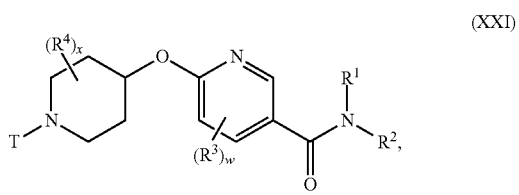

(XXI)

in which the variables are defined as described above with reference to structural formula (I).

In another embodiment of the presently disclosed compounds, the compound has structural formula (XXII):

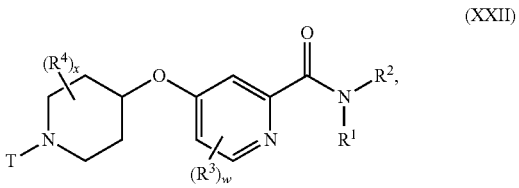

(XXII)

in which the variables are defined as described above with reference to structural formula (I).

In another embodiment of the presently disclosed compounds, the compound has structural formula (XXII):

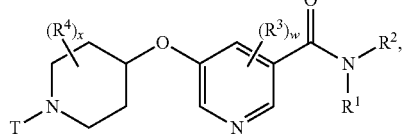
(XXIII)

in which the variables are defined as described above with reference to structural formula (I).

In another embodiment of the presently disclosed compounds, the compound has structural formula (XXIV):

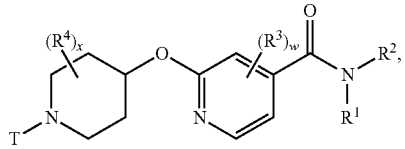
(XXIV)

in which the variables are defined as described above with reference to structural formula (I).

In another embodiment of the presently disclosed compounds, the compound has structural formula (XXV):

(XXV)

in which the variables are defined as described above with reference to structural formula (I).

In one embodiment of the presently disclosed compounds, the compound has structural formula (XXVI):

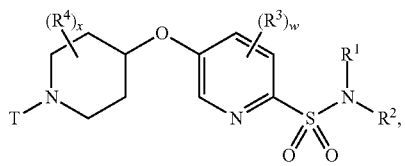
(XXVI)

in which the variables are defined as described above with reference to structural formula (I).

In another embodiment of the presently disclosed compounds, the compound has structural formula (XXVII):

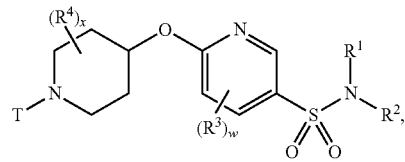
(XXVII)

in which the variables are defined as described above with reference to structural formula (I).

In another embodiment of the presently disclosed compounds, the compound has structural formula (XXVIII):

(XXVIII)

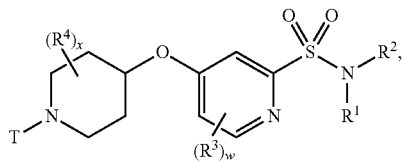

in which the variables are defined as described above with reference to structural formula (I).

In another embodiment of the presently disclosed compounds, the compound has structural formula (XXIX):

(XXIX)

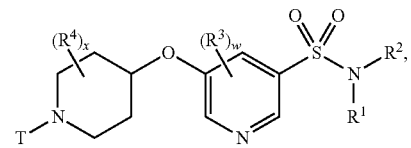

in which the variables are defined as described above with reference to structural formula (I).

In another embodiment of the presently disclosed compounds, the compound has structural formula (XXX):

(XXX)

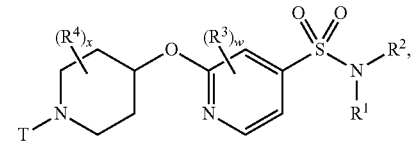

in which the variables are defined as described above with reference to structural formula (I).

In another embodiment of the presently disclosed compounds, the compound has structural formula (XXXI):

(XXXI)

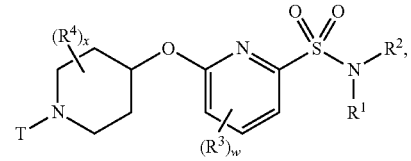

in which the variables are defined as described above with reference to structural formula (I).

In one embodiment of the presently disclosed compounds, the compound has structural formula (XXXII):

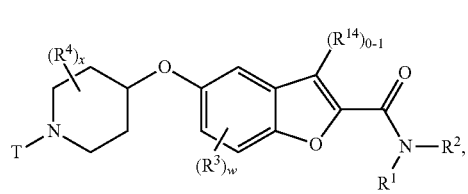

(XXXII)

in which the variables are defined as described above with reference to structural formula (I). In certain embodiments, one $R^{14}$ is substituted on the furano carbon. In other embodiments, no $R^{14}$ is substituted on the furano carbon.

In another embodiment of the presently disclosed compounds, the compound has structural formula (XXXIII):

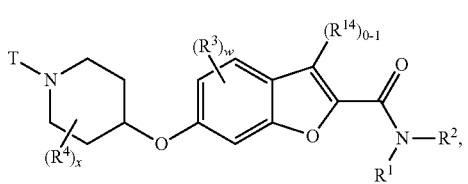

(XXXIII)

in which the variables are defined as described above with reference to structural formula (I). In certain embodiments, one $R^{14}$ is substituted on the furano carbon. In other embodiments, no $R^{14}$ is substituted on the furano carbon.

In one embodiment of the presently disclosed compounds, the compound has structural formula (XXXIV):

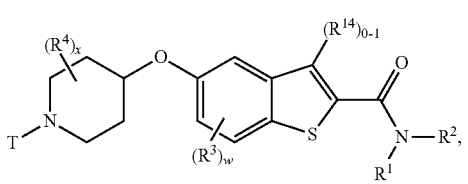

(XXXIV)

in which the variables are defined as described above with reference to structural formula (I). In certain embodiments, one $R^{14}$ is substituted on the thieno carbon. In other embodiments, no $R^{14}$ is substituted on the thieno carbon.

In another embodiment of the presently disclosed compounds, the compound has structural formula (XXXV):

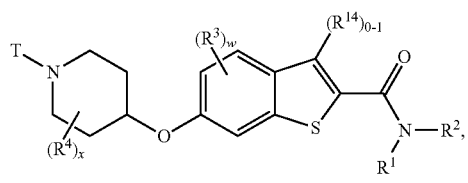

(XXXV)

in which the variables are defined as described above with reference to structural formula (I). In certain embodiments, one $R^{14}$ is substituted on the thieno carbon. In other embodiments, no $R^{14}$ is substituted on the thieno carbon.

In one embodiment of the presently disclosed compounds, the compound has structural formula (XXXVI):

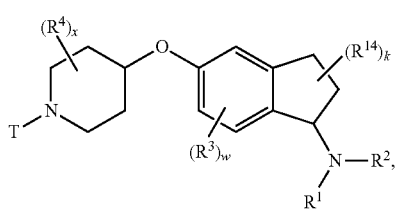

(XXXVI)

in which the variables are defined as described above with reference to structural formula (I).

In another embodiment of the presently disclosed compounds, the compound has structural formula (XXXVII):

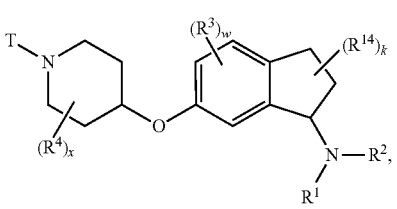

(XXXVII)

in which the variables are defined as described above with reference to structural formula (I).

In certain embodiments of the presently disclosed compounds of any of structural formulae (I)-(XXXVII), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (I)-(XXXVII), $R^2$ is -Hca. In certain embodiments, $R^2$ is an optionally-substituted monocyclic heterocycloalkyl. In another embodiment, $R^2$ is not an oxo-substituted heterocycloalkyl.

In certain particular compounds disclosed herein having any of structural formulae (I)-(XXXVII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In particular embodiments of the presently disclosed compounds of any of structural formulae (I)-(XXXVII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (I)-(XXXVII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (I)-(XXXVII), the azetidinyl, pyrrolidinyl, piperidinyl or azepanyl $R^2$ moiety is substituted at its 1-position with an optionally substituted pyridinylmethyl, an optionally substituted furanylmethyl or an optionally substituted thienylmethyl. For example, the azetidinyl, pyrrolidinyl, piperidinyl or azepanyl $R^2$ moiety can be substituted with an unsubstituted pyridinylmethyl, an unsubstituted furanylmethyl, or an unsubstituted thienylmethyl.

In other embodiments of the presently disclosed compounds of any of structural formulae (I)-(XXXVII), the azetidinyl, pyrrolidinyl, piperidinyl or azepanyl $R^2$ moiety is substituted at its 1-position with —C(O)—O($C_0$-$C_6$ alkyl), —C(O)—Het, —C(O)—Ar, —S(O)$_2$-Het, —S(O)$_2$—Ar or —S(O)$_2$—O($C_0$-$C_6$ alkyl).

In certain embodiments of the compounds of any of structural formulae (I)-(XXXVII), $R^2$ is -Cak-N($R^9$)-G-$R^{22}$, as described above. For example, in one embodiment of the disclosed compounds, $R^2$ has the structure

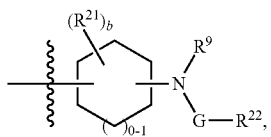

in which b is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, b is 1 or 2. In other embodiments, b is 0. In certain embodiments, $R^9$ is H. In certain embodiments, G is a single bond.

In one embodiment of compounds of any of structural formulae (I)-(XXXVII), $R^2$ has the structure

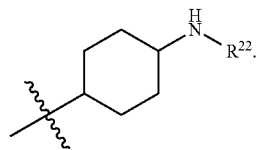

In certain embodiments of the compounds of any of structural formulae (I)-(XXXVII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -G$R^{23}$, or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —CH$_2$—CH$_2$—CH$_2$—N($R^9$)—$R^{24}$ or —CH$_2$—CH$_2$—CH$_2$—CH$_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —CH$_2$—CH$_2$—O—CH$_2$—CH$_2$—N($R^9$)—$R^{24}$; —CH$_2$—CH(CH$_3$)—N($R^9$)—$R^{24}$; or —CH$_2$—CH$_2$—O—CH$_2$—C(O)—N($R^9$)—$R^{24}$. In certain embodiments, $R^9$ is H. In certain embodiments, $R^{24}$ is Ar or Het. In certain embodiments, the ($C_2$-$C_8$ alkyl) is a ($C_2$-$C_5$ alkyl).

In the compounds of any of structural formulae (I)-(XXXVII), w is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In certain embodiments, an $R^3$ is substituted on the "B" ring system at a benzo or pyrido ring position meta to the alicyclic ethereal oxygen.

In certain embodiments of the compounds of any of structural formulae (I)-(XXXVII), each $R^3$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-

($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each R$^3$ is —($C_1$-$C_3$ alkyl), —($C_1$-$C_3$ haloalkyl), —($C_0$-$C_3$ alkyl)-L-R$^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each R$^7$, R$^8$ and R$^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments of the compounds of any of structural formulae (I)-(XXXVII), w is at least one, and at least one R$^3$ is —NR$^8$R$^9$. For example, in one embodiment, w is 1. In certain such embodiments, R$^3$ is substituted on the "B" ring system at a benzo or pyrido ring position meta to the alicyclic ethereal oxygen.

In other embodiments of the compounds of any of structural formulae (I)-(XXXVII), w is at least one, and at least one R$^3$ is —($C_0$-$C_3$ alkyl)-Y$^1$—($C_1$-$C_3$ alkyl)-Y$^2$—($C_0$-$C_3$ alkyl), in which each of Y$^1$ and Y$^2$ is independently L, —O—, —S— or —NR$^9$—. For example, in one embodiment, w is 1. In certain such embodiments, R$^3$ is substituted on the "B" ring system at a benzo or pyrido ring position meta to the alicyclic ethereal oxygen. In one particular embodiment, R$^3$ is —CH$_2$—N(CH$_3$)—CH$_2$—C(O)—OCH$_3$.

In the presently disclosed compounds of any of structural formulae (I)-(XXXVII), the number of substituents on the azacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (I)-(XXXVII), two R$^4$s combine to form an oxo. The oxo can be bound, for example, at the position alpha to the nitrogen of the azacycloalkyl ring. In other embodiments, no two R$^4$s combine to form an oxo.

In certain embodiments of the presently disclosed compounds of any of structural formulae (I)-(XXXVII), when x is 4, not all four R$^4$ moieties are ($C_1$-$C_6$ alkyl).

In certain embodiments of the presently disclosed compounds of any of structural formulae (I)-(XXXVII), each R$^4$ is independently selected from —($C_1$-$C_6$ alkyl), —($C_1$-$C_6$ haloalkyl) (e.g., trifluoromethyl), —($C_0$-$C_6$ alkyl)-L-R$^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each R$^7$, R$^8$ and R$^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each R$^4$ is —($C_1$-$C_3$ alkyl), —($C_1$-$C_3$ haloalkyl), —($C_0$-$C_3$ alkyl)-L-R$^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each R$^7$, R$^8$ and R$^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (XXXVIII):

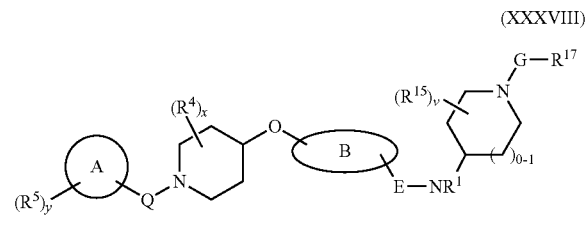

(XXXVIII)

in which Q and G are each independently a bond, —CH$_2$—, —C(H)(R$^{16}$)—, —C(R$^{16}$)$_2$— or —S(O)$_2$—; v is 0, 1, 2, 3 or 4; each R$^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-R$^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two R$^{15}$ on the same carbon optionally combine to form oxo; R$^{17}$ is Het or Ar, and all other variables are defined as described above with reference to structural formula (I)-(XXXVII). In one embodiment, Q is a single bond. In another embodiment, Q is —CH$_2$—. In other embodiments, Q is —C(O)— or —S(O)$_2$—. In certain embodiments, G is —CH$_2$—. In other embodiments, G is —C(O)— or —S(O)$_2$—. In other embodiments, G is —CH(CH$_3$)—. For example, in one embodiment, Q i)s a single bond and G is —CH$_2$— or —C(O)—. As described above, in certain embodiments, the ring system denoted by "A" is aryl or heteroaryl. In one embodiment, the ring system denoted by "A" is substituted with one or more electron-withdrawing groups. In another embodiment, R$^{17}$ is substituted with one or more electron-withdrawing groups. In certain embodiments, the ring system denoted by "A", R$^{17}$ or both are not substituted with an aryl, heteroaryl, cycloalkyl or heterocycloalkyl-containing group.

In the presently disclosed compounds of structural formula (XXXVIII), v is 0, 1, 2, 3 or 4. In one embodiment, v is 0, 1, 2 or 3. For example, v can be 0, or can be 1 or 2.

In certain embodiments of the presently disclosed compounds of structural formula (XXXVIII), two R$^{15}$s combine to form an oxo. The oxo can be bound, for example, at the position alpha to the nitrogen of the azacycloalkyl ring. In other embodiments, no two R$^{15}$s combine to form an oxo.

In certain embodiments of the presently disclosed compounds of structural formula (XXXVIII), when v is 4, not all four R$^{15}$ moieties are ($C_1$-$C_6$ alkyl).

In certain embodiments of the presently disclosed compounds of structural formula (XXXVIII), each R$^{15}$ is independently selected from —($C_1$-$C_6$ alkyl), —($C_1$-$C_6$ haloalkyl) (e.g., trifluoromethyl), —($C_0$-$C_6$ alkyl)-L-R$^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —C(O)$NR^9R^7$, which can be bound, for example, at a position alpha to the piperidine nitrogen, or at the position linked to the —N($R^1$)—.

In certain embodiments of the presently disclosed compounds of structural formula (XXXVIII), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca. $R^{17}$ can be substituted with, for example, one such substituent, or two such substituents.

In certain embodiments, the presently disclosed compounds have the structural formula (XXXIX):

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (I) and (XXXVIII).

In certain embodiments, the presently disclosed compounds have the structural formula (XL):

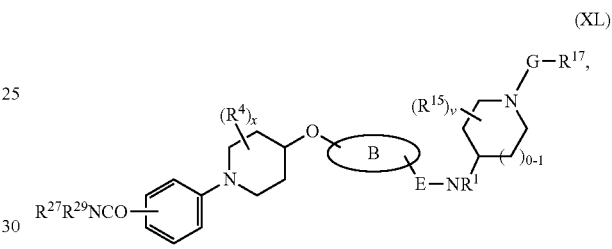

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (I) and (XXXVIII).

In certain embodiments, the presently disclosed compounds have the structural formula (XLI):

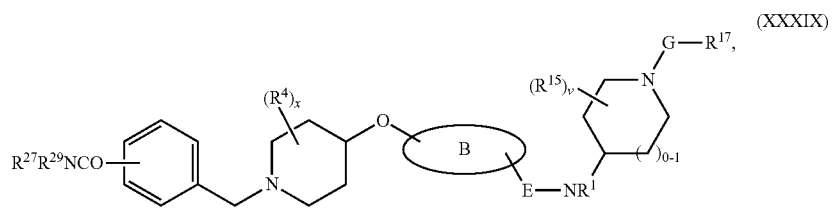

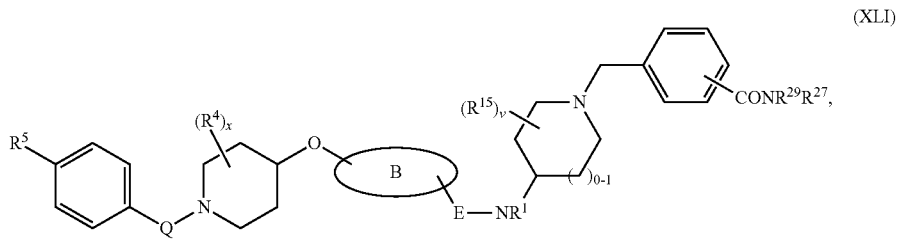
(XLI)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (I) and (XXXVIII).

In certain embodiments, the presently disclosed compounds have the structural formula (XLII):

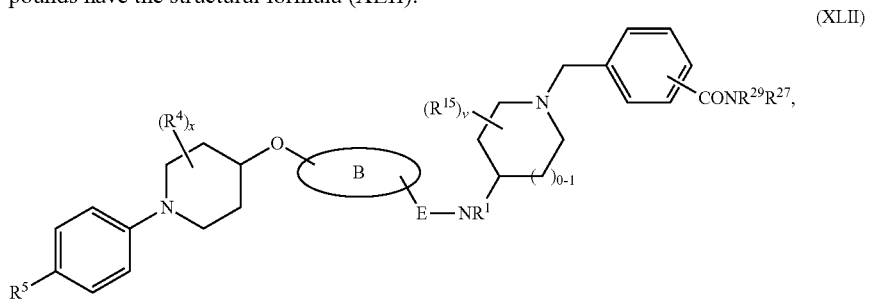
(XLII)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (I) and (XXXVIII).

In certain embodiments, the presently disclosed compounds have the structural formula (XLIII):

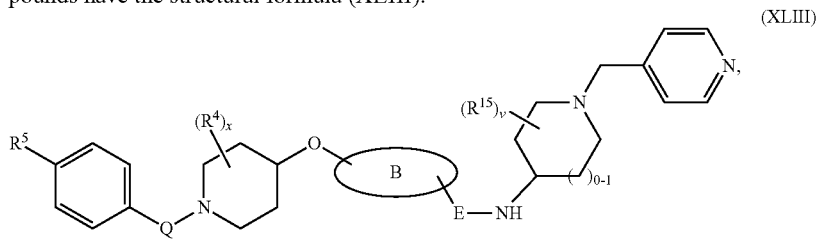
(XLIII)

in which all variables are as described above with respect to structural formulae (I) and (XXXVIII).

In certain embodiments, the presently disclosed compounds have the structural formula (XLIV):

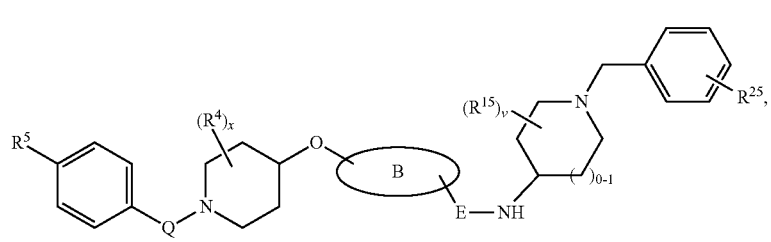

(XLIV)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with respect to structural formulae (I) and (XXXVIII). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (XLV):

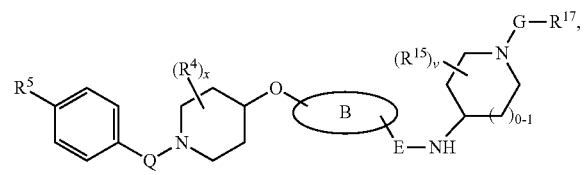

(XLV)

in which G is —C(O)— or —S(O)$_2$— and all other variables are as described above with respect to structural formulae (I) and (XXXVIII).

In certain embodiments, the presently disclosed compounds have the structural formula (XLVI):

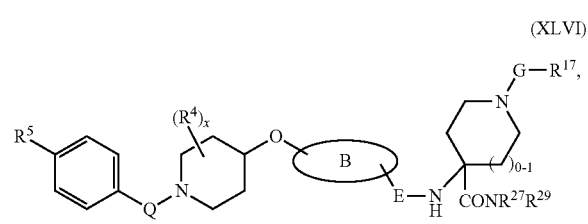

(XLVI)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (I) and (XXXVIII). In some embodiments, the compounds of structural formula (XLVI) are present as racemic mixtures or scalemic mixtures. In other embodiments, the compounds of structural formula (XLVI) are present in an enantiomerically-enriched form, for example as a substantially pure stereoisomer.

In certain embodiments, the presently disclosed compounds have the structural formula (XLVII):

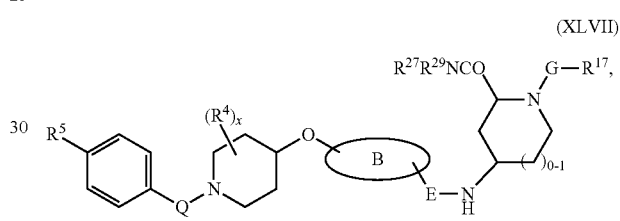

(XLVII)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (I) and (XXXVIII). In some embodiments, the compounds of structural formula (XLVII) are present as racemic mixtures or scalemic mixtures. In other embodiments, the compounds of structural formula (XLVII) are present in an enantiomerically-enriched form, for example as a substantially pure stereoisomer.

In certain embodiments, the presently disclosed compounds have the structural formula (XLVIII):

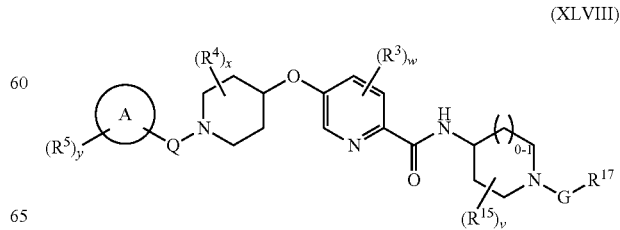

(XLVIII)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (XLIX):

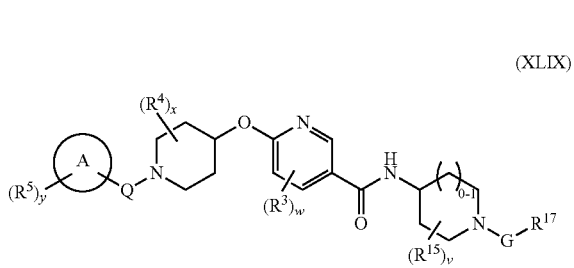

(XLIX)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (L):

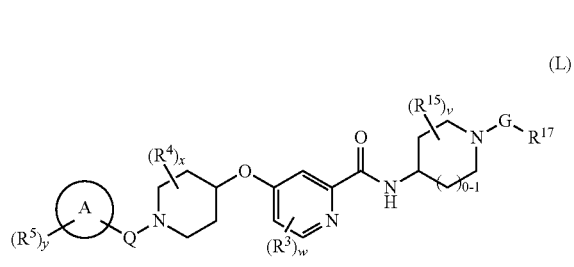

(L)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (LI):

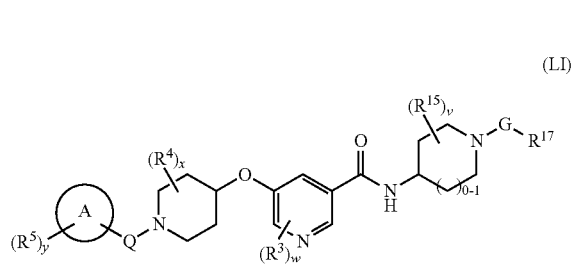

(LI)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (LII):

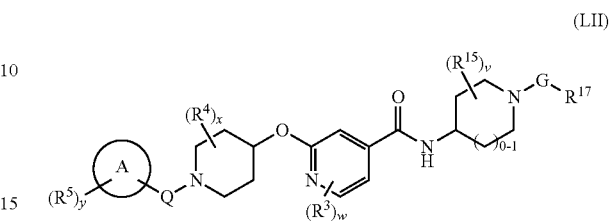

(LII)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (LIII):

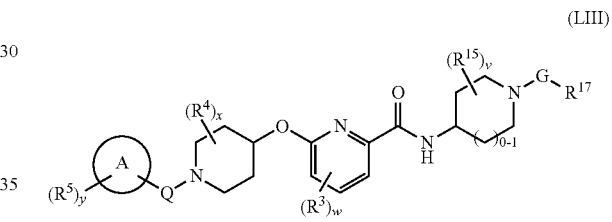

(LIII)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (LIV):

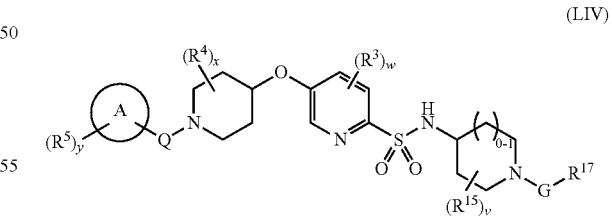

(LIV)

in which G, v, R$^{15}$ and R$^{17}$ are defined as described above with reference to structural formula (XXXVIII), and all other variables are defined as described above with reference to structural formulae (I) and (XXXVIII). R$^5$, v, R$^{15}$, R$^{17}$, Q, G and the ring denoted by "A" can be defined, for example, as described with respect to any of structural formulae (XXXIX)-(XLVII).

In certain embodiments, the presently disclosed compounds have the structural formula (LV):

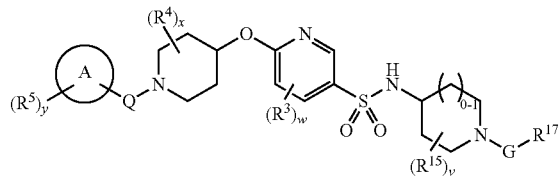

(LV)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII).

In certain embodiments, the presently disclosed compounds have the structural formula (LVI):

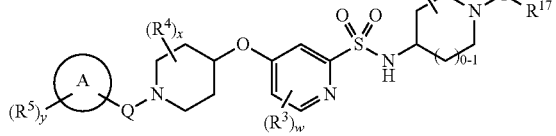

(LVI)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII).

In certain embodiments, the presently disclosed compounds have the structural formula (LVII):

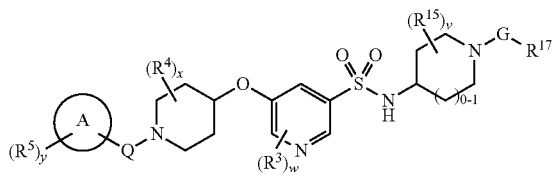

(LVII)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII).

In certain embodiments, the presently disclosed compounds have the structural formula (LVIII):

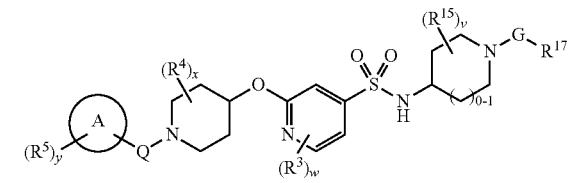

(LVIII)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII).

In certain embodiments, the presently disclosed compounds have the structural formula (LIX):

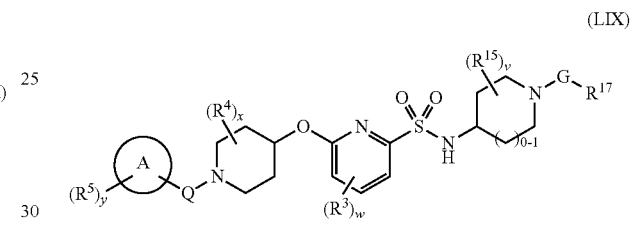

(LIX)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII).

In certain embodiments, the presently disclosed compounds have the structural formula (LX):

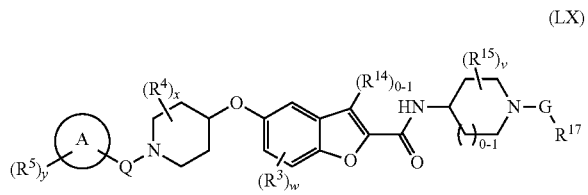

(LX)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII). In certain embodiments, one $R^{14}$ is substituted on the furano carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments, the presently disclosed compounds have the structural formula (LXI):

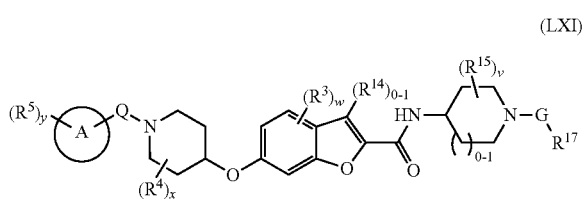

(LXI)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII). In certain embodiments, one $R^{14}$ is substituted on the furano carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments, the presently disclosed compounds have the structural formula (LXII):

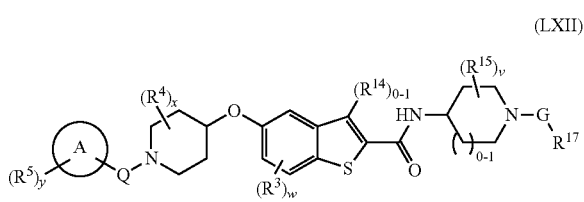

(LXII)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII). In certain embodiments, one $R^{14}$ is substituted on the thieno carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the thieno carbon.

In certain embodiments, the presently disclosed compounds have the structural formula (LXIII):

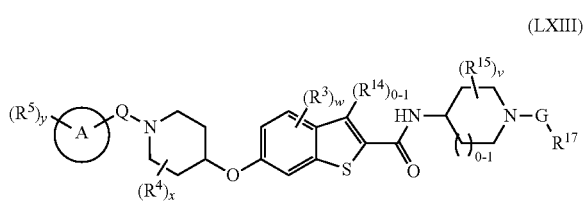

(LXIII)

in which G, v, $R^{15}$ and $R^{17}$ are defined as described above with reference to structural formula (XXXVIII), and all other variables are defined as described above with reference to structural formulae (I) and (XXXVIII). $R^5$, v, $R^{15}$, $R^{17}$, Q, G and the ring denoted by "A" can be defined, for example, as described with respect to any of structural formulae (XXXIX)-(XLVII). In certain embodiments, one $R^{14}$ is substituted on the thieno carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the thieno carbon.

In certain embodiments, the presently disclosed compounds have the structural formula (LXIV):

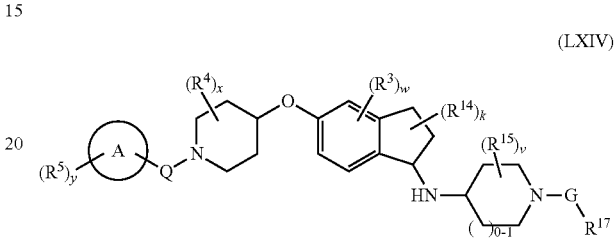

(LXIV)

in which Q, G, v, $R^{15}$ and $R^{17}$ are defined as described above with reference to structural formula (XXXVIII), and all other variables are defined as described above with reference to structural formula (I). $R^5$, $R^{15}$, $R^{17}$, Q, G and the ring denoted by "A" can be defined, for example, as described with respect to any of structural formulae (XXXIX)-(XLVII).

In certain embodiments, the presently disclosed compounds have the structural formula (LXV):

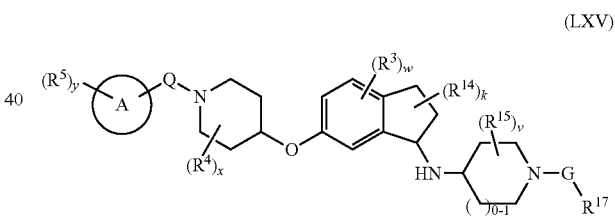

(LXV)

in which Q, G, v, $R^{15}$ and $R^{17}$ are defined as described above with reference to structural formula (XXXVIII), and all other variables are defined as described above with reference to structural formula (I). $R^5$, $R^{15}$, $R^{17}$, Q, G and the ring denoted by "A" can be defined, for example, as described with respect to any of structural formulae (XXXIX)-(XLVII).

In certain embodiments of compounds having structural formulae (XXXVIII)-(LXV), the

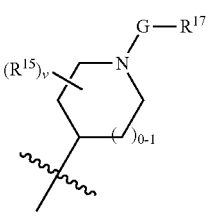

moiety has the structure

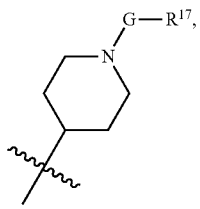

in which G is —CH$_2$—, —CH(CH$_3$)—, —C(O)— or —S(O)$_2$—. For example, in one embodiment, G is —CH$_2$—. In another embodiment, G is —C(O)— or —S(O)$_2$—.

In other embodiments of compounds having structural formulae (XXXVIII)-(LXV), the

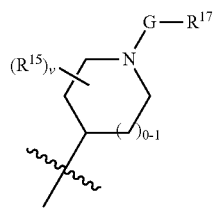

moiety has the structure

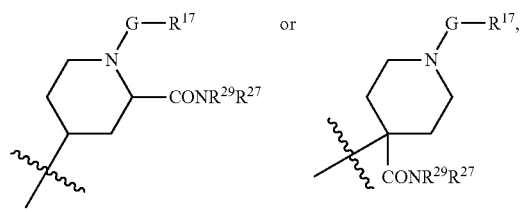

in which G is —CH$_2$—, —C(O)— or —S(O)$_2$—. In such embodiments, the compounds of structural formula (XLVII) can be present as racemic mixtures or scalemic mixtures, or in an enantiomerically-enriched form, for example as a substantially pure stereoisomer.

In other embodiments of compounds having structural formulae (XXXVIII)-(LXV), the

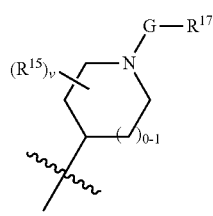

moiety has the structure

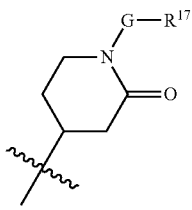

in which G is —CH$_2$—, —C(O)— or —S(O)$_2$—.

In certain embodiments of compounds having structural formulae (XXXVIII)-(LXV), the R$^{17}$ moiety has the structure

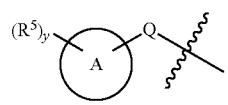

in which R$^{27}$ is selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) —(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

In certain embodiments of compounds having structural formulae (XXXVIII)-(LXV), the

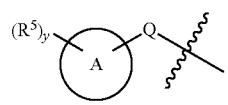

moiety is p-(trifluoromethyl)phenyl.

In one embodiment, the presently disclosed compounds have the structural formula (LXVI):

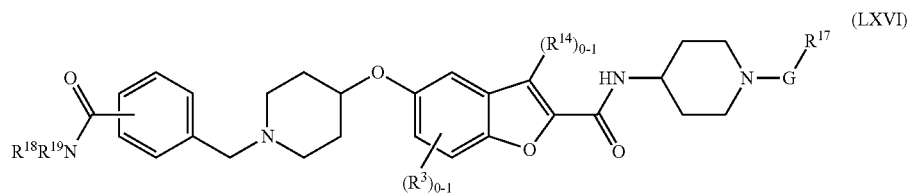

(LXVI)

in which G, $R^3$ and $R^{17}$ are as described above with respect to structural formula (XXXVIII); $R^{18}$ is H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca; and $R^{20}$ is Ar or Het. In certain embodiments, $R^{18}$ is H or ($C_1$-$C_4$ alkyl), and $R^{19}$ is —H. In certain embodiments, one $R^{14}$ is substituted on the furano carbon. $R^{14}$ can be, for example, as described above with reference to structural formula (I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments of compounds of structural formula (LXVI), w is 1, and $R^3$ is —$NR^8R^9$. In certain such embodiments, $R^3$ is substituted at a benzo or pyrido ring position meta to the alicyclic ethereal oxygen.

In other embodiments of compounds of structural formula (LXVI), w is 1, and $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. In certain such embodiments, $R^3$ is substituted at a benzo or pyrido ring position meta to the alicyclic ethereal oxygen.

In another embodiment, the presently disclosed compounds have the structural formula (LXVII):

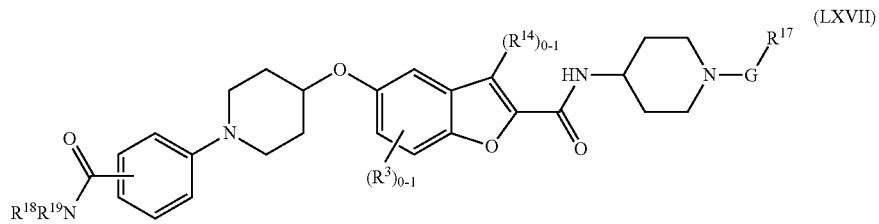

(LXVII)

in which $R^3$ and $R^{14}$ are defined as described above with reference to structural formulae (I) and (XXXVIII); G and $R^{17}$ are defined as described above with reference to structural formula (XXXVIII); and $R^{18}$ and $R^{19}$ are defined as described above with reference to structural formula (LXVI).

In another embodiment, the presently disclosed compounds have the structural formula (LXVIII):

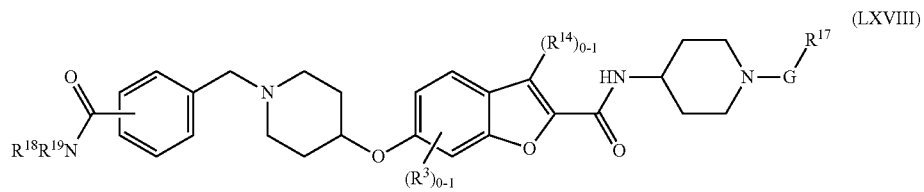

(LXVIII)

in which $R^3$ and $R^{14}$ are defined as described above with reference to structural formulae (I) and (XXXVIII); G and $R^{17}$ are defined as described above with reference to structural formula (XXXVIII); and $R^{18}$ and $R^{19}$ are defined as described above with reference to structural formula (LXVI).

In another embodiment, the presently disclosed compounds have the structural formula (LXIX):

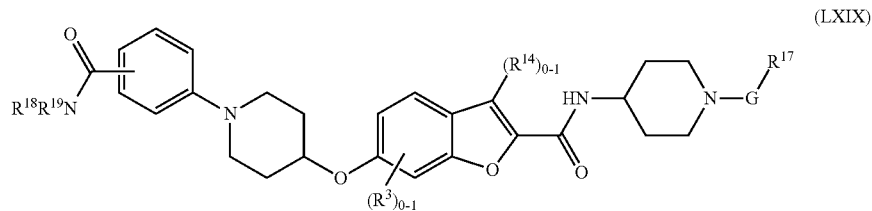

(LXIX)

in which $R^3$ and $R^{14}$ are defined as described above with reference to structural formulae (I) and (XXXVIII); G and $R^{17}$ are defined as described above with reference to structural formula (XXXVIII); and $R^{18}$ and $R^{19}$ are defined as described above with reference to structural formula (LXVI).

In another embodiment, the presently disclosed compounds have the structural formula (LXX):

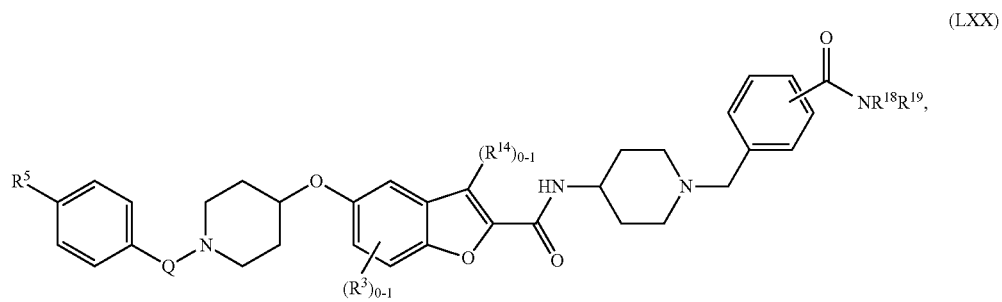

(LXX)

in which Q, $R^3$, $R^5$ and $R^{14}$ are defined as described above with reference to structural formulae (I) and (XXXVIII); and $R^{18}$ and $R^{19}$ are defined as described above with reference to structural formula (LXVI).

In another embodiment, the presently disclosed compounds have the structural formula (LXXI):

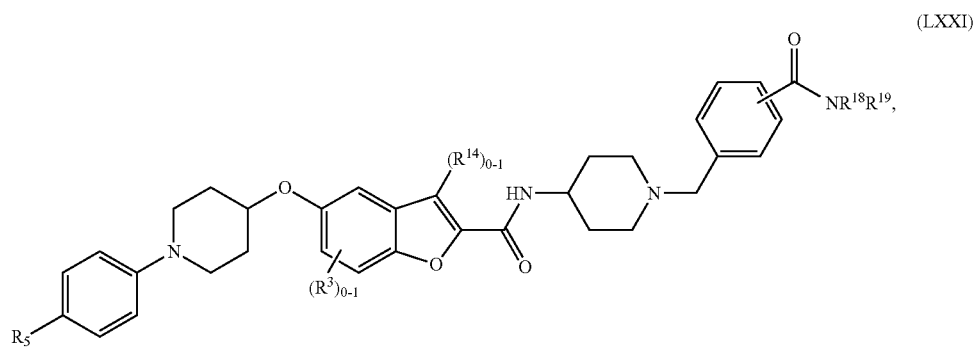

(LXXI)

in which $R^3$, $R^5$ and $R^{14}$ are defined as described above with reference to structural formulae (I) and (XXXVIII); and $R^{18}$ and $R^{19}$ are defined as described above with reference to structural formula (LXVI).-

In another embodiment, the presently disclosed compounds have the structural formula (LXXII):

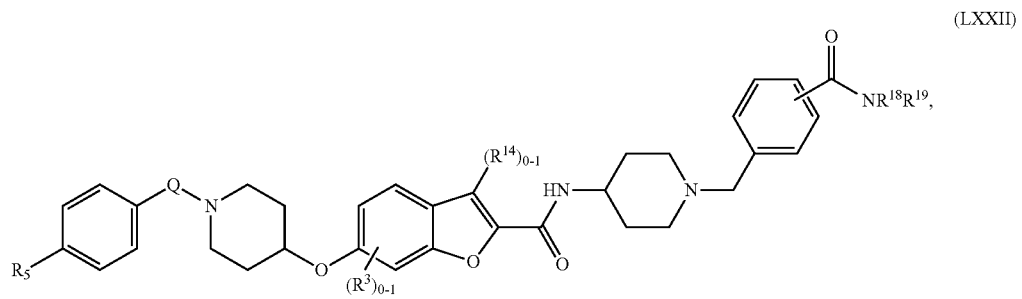

(LXXII)

in which Q, $R^3$, $R^5$ and $R^{14}$ are defined as described above with reference to structural formulae (I) and (XXXVIII); and $R^{18}$ and $R^{19}$ are defined as described above with reference to structural formula (LXVI).

In another embodiment, the presently disclosed compounds have the structural formula (LXXIII):

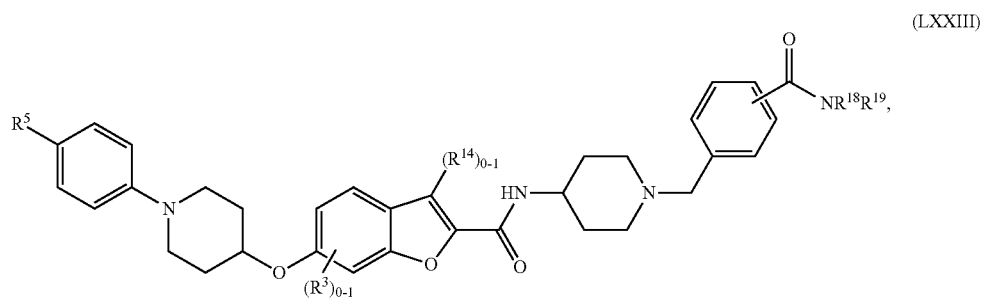

(LXXIII)

in which $R^3$, $R^5$ and $R^{14}$ are defined as described above with reference to structural formulae (I) and (XXXVIII); and $R^{18}$ and $R^{19}$ are defined as described above with reference to structural formula (LXVI).

In another embodiment, the presently disclosed compounds have the structural formula (LXXIV):

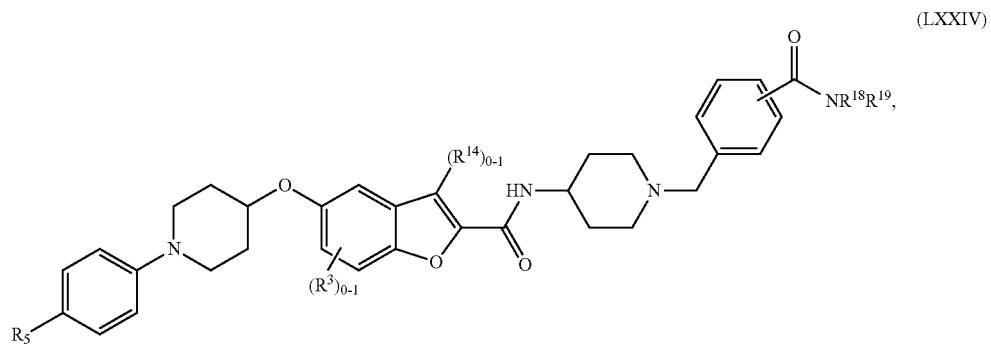

(LXXIV)

in which $R^3$, $R^5$ and $R^{14}$ are defined as described above with reference to structural formulae (I) and (XXXVIII); and $R^{18}$ and $R^{19}$ are defined as described above with reference to structural formula (LXVI).

In one embodiment, the presently disclosed compounds have the structural formula (LXXV):

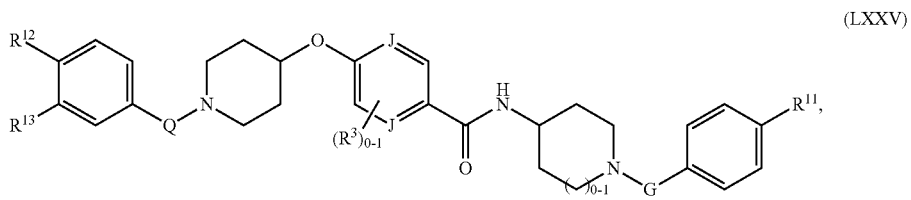
(LXXV)

in which one J is N and the other is CH; Q is —CH$_2$— or a single bond; G is CH$_2$ or C(O); R$^3$ is as described above with respect to structural formulae (I) and (XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (LXXVI):

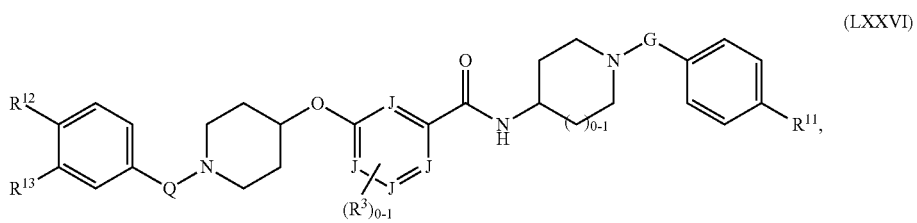
(LXXVI)

in which one J is N and the other is CH; Q is —CH$_2$— or a single bond; G is CH$_2$ or C(O); R$^3$ is as described above with respect to structural formulae (I) and (XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (LXXVII):

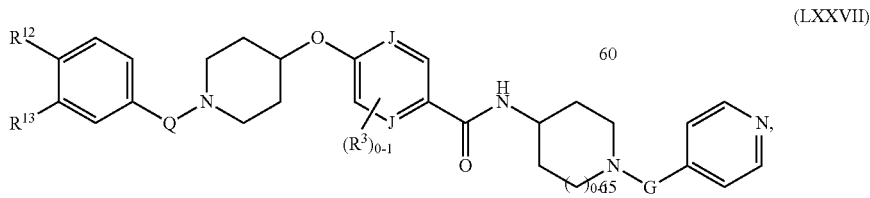
(LXXVII)

in which one J is N, and the other is CH; Q is —CH$_2$— or a single bond; G is CH$_2$ or C(O); R$^3$ is as described above with respect to structural formulae (I) and (XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (LXXVIII):

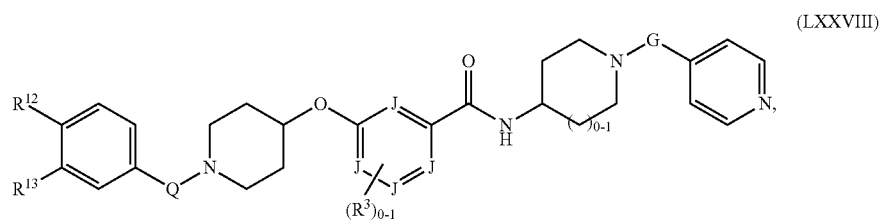

(LXXVIII)

in which one J is N, and the other three are CH; Q is —CH$_2$— or a single bond; G G is CH$_2$ or C(O); R$^3$ is as described above with respect to structural formulae (I) and (XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (LXXIX):

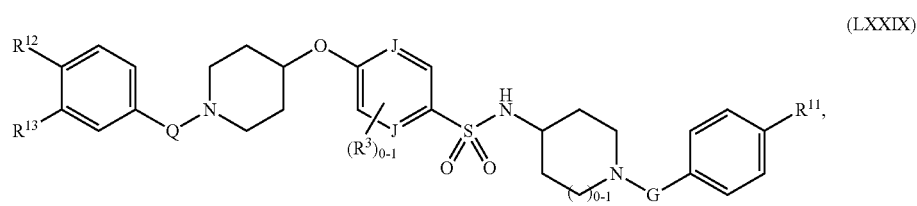

(LXXIX)

in which one J is N and the other is CH; Q is —CH$_2$— or a single bond G is CH$_2$ or C(O); R$^3$ is as described above with respect to structural formulae (I) and (XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.-

In certain embodiments, the presently disclosed compounds have the structural formula (LXXX):

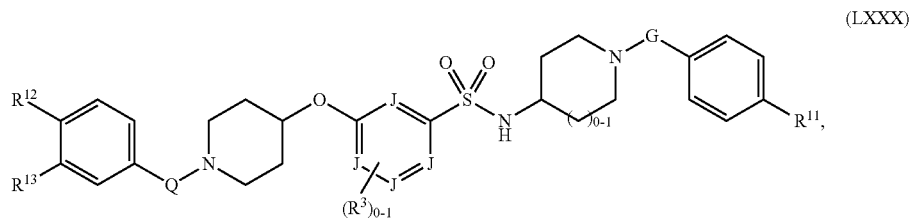

(LXXX)

in which one J is N, and the other three are CH; Q is —CH$_2$— or a single bond; G is CH$_2$ or C(O); R$^3$ is as described above with respect to structural formulae (I) and (XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (LXXXI):

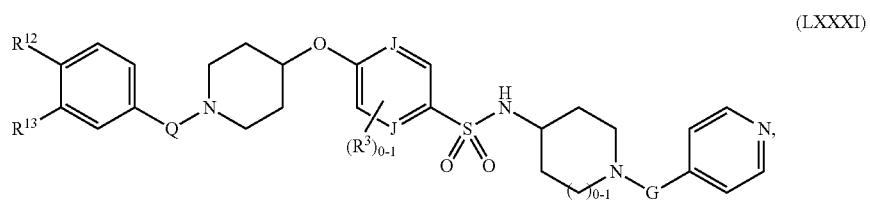

(LXXXI)

in which one J is N, and the other three are CH; Q is —CH$_2$— or a single bond; G is CH$_2$ or C(O); R$^3$ is as described above with respect to structural formulae (I) and (XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$

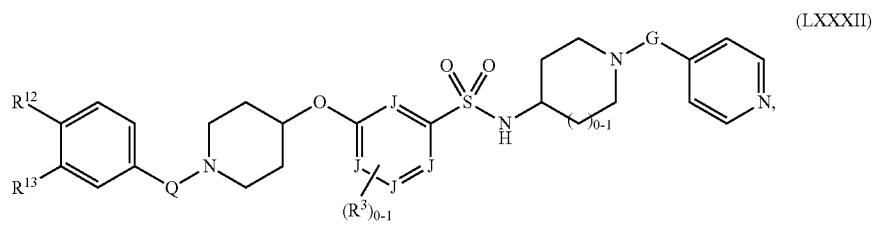

(LXXXII)

in which one J is N, and the other is CH; Q is —CH$_2$— or a single bond; G is CH$_2$ or C(O); R$^3$ is as described above with respect to structural formulae (I) and (XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (LXXXII):
alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H.

In certain embodiments, the presently disclosed compounds have the structural formula (LXXXIII):

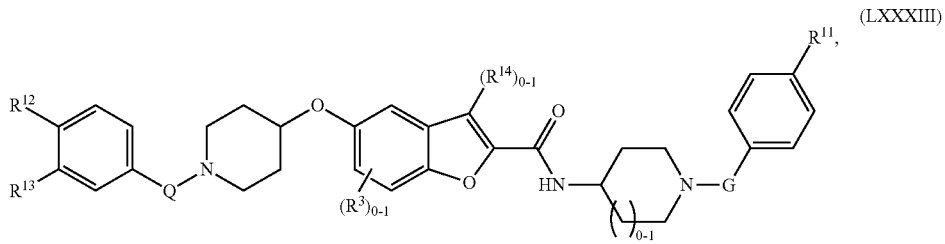

(LXXXIII)

in which Q is —$CH_2$— or a single bond; G is $CH_2$ or C(O); $R^3$ is as described above with respect to structural formulae (I) and (XXXVIII) (e.g., absent or halo); $R^{14}$ is as described above with respect to structural formulae (I) and (LX) (e.g., absent, methyl or halo); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (LXXXIV):

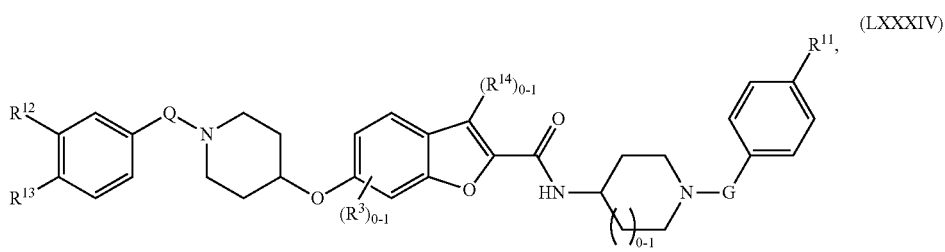

(LXXXIV)

in which Q is —$CH_2$— or a single bond; G is $CH_2$ or C(O); $R^3$ is as described above with respect to structural formulae (I) and (XXXVIII) (e.g., absent or halo); $R^{14}$ is as described above with respect to structural formulae (I) and (LXI) (e.g., absent, methyl or halo); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (LXXXV):

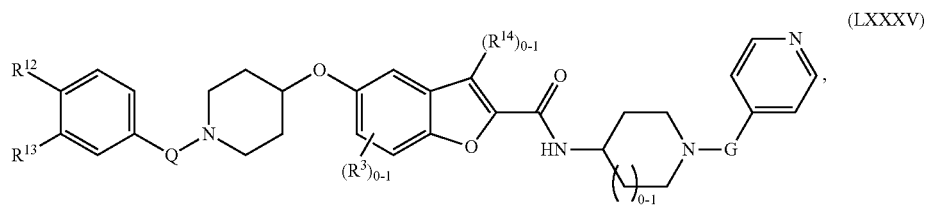

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formulae (I) and (LX) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (LXXXVI):

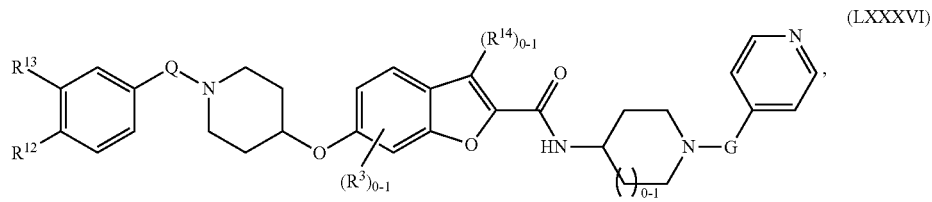

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formulae (I) and (LXI) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (LXXXVII):

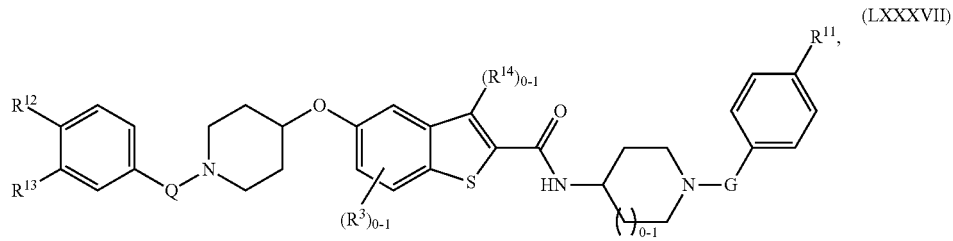

(LXXXVII)

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formulae (I) and (LXII) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (LXXXVIII):

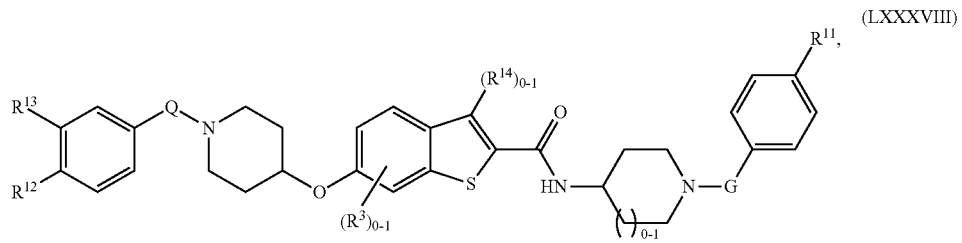

(LXXXVIII)

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formulae (I) and (LXIII) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.-

In certain embodiments, the presently disclosed compounds have the structural formula (LXXXIX):

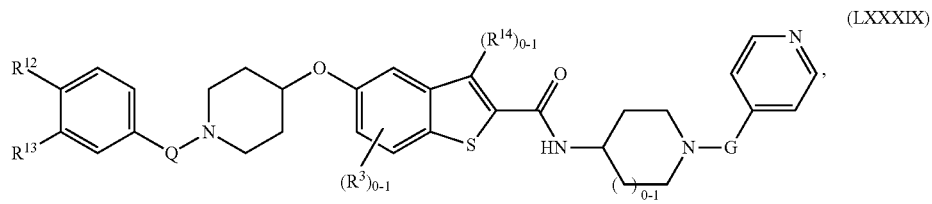

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formulae (I) and (LXII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (XC):

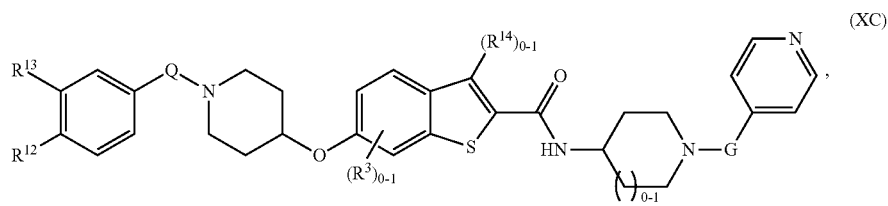

in which Q is —CH$_2$— or a single bond; G is CH$_2$ or CO; G is CH$_2$ or C(O); R$^3$ is as described above with respect to structural formulae (I) and (XXXVIII) (e.g., absent or halo); R$^{14}$ is as described above with respect to structural formulae (I) and (LXIII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (XCI):

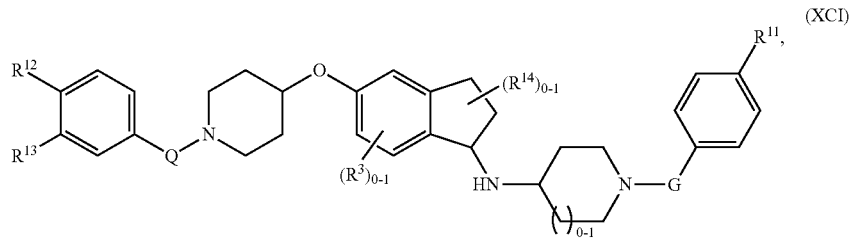

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formula (I) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (XCII):

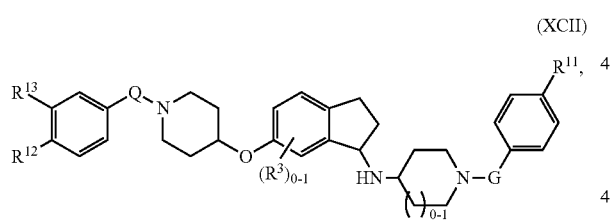

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formula (I) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (XCIII):

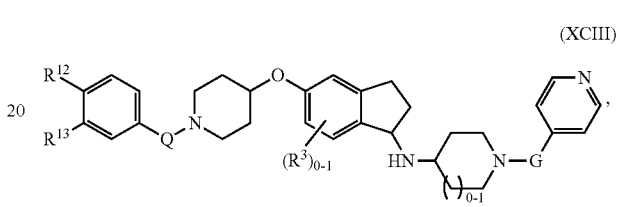

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formula (I) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (XCIV):

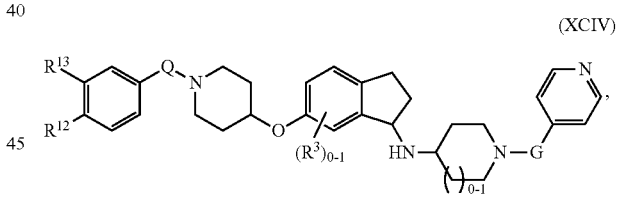

in which Q is —CH$_2$— or a single bond; G is CH$_2$ or C(O); R$^3$ is as described above with respect to structural formulae (I) and (XXXVIII) (e.g., absent or halo); R$^{14}$ is as described above with respect to structural formula (I) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

Examples of compounds according to structural formula (I) include those listed in Table 1. These compounds can be made according to the general schemes described below, for example using a procedure analogous to those described below in the Examples.

TABLE 1

| No. | Name | Structure |
|-----|------|-----------|
| 1 | 5-(1-(4-cyanophenyl)piperidin-4-yloxy)-N-(1-(pyridin-4-ylmethyl)piperidin-4-yl)picolinamide | 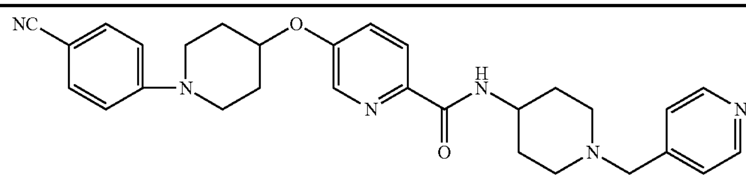 |
| 2 | N-(1-(4-cyanobenzyl)piperidin-4-yl)-5-(1-(4-cyanophenyl)piperidin-4-yloxy)picolinamide | 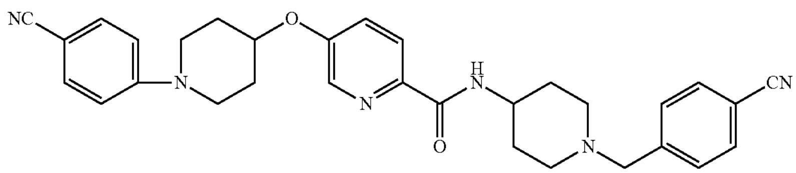 [SMILES: N#Cc1ccc(CN2CCC(NC(=O)c3ccc(OC4CCN(c5ccc(C#N)cc5)CC4)cn3)CC2)cc1] |
| 3 | N-(1-(pyridin-4-ylmethyl)piperidin-4-yl)-5-(1-(4-(trifluoromethyl)phenyl)piperidin-4-yloxy)picolinamide | 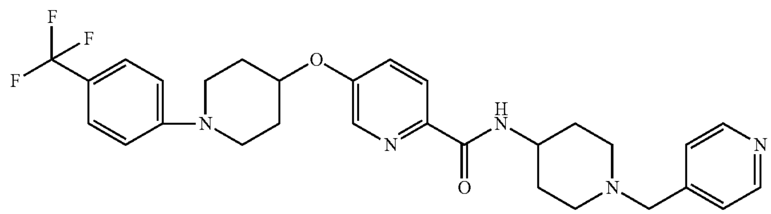 [SMILES: O=C(NC1CCN(Cc2ccncc2)CC1)c1ccc(OC2CCN(c3ccc(C(F)(F)F)cc3)CC2)cn1] |
| 4 | N-(1-(4-cyanobenzyl)piperidin-4-yl)-5-(1-(4-(trifluoromethyl)phenyl)piperidin-4-yloxy)picolinamide | 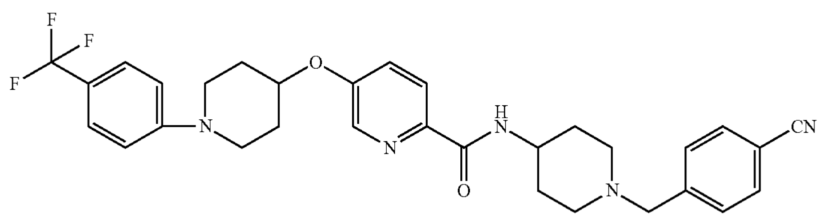 [SMILES: N#Cc1ccc(CN2CCC(NC(=O)c3ccc(OC4CCN(c5ccc(C(F)(F)F)cc5)CC4)cn3)CC2)cc1] |
| 5 | N-(1-(pyridin-3-ylmethyl)piperidin-4-yl)-5-(1-(4-(trifluoromethyl)phenyl)piperidin-4-yloxy)picolinamide | 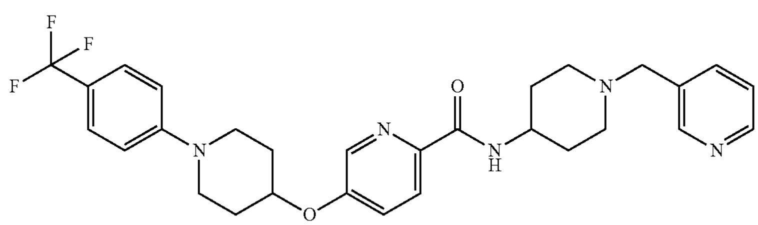 [SMILES: O=C(NC1CCN(Cc2cccnc2)CC1)c1ccc(OC2CCN(c3ccc(C(F)(F)F)cc3)CC2)cn1] |
| 6 | N-(1-(pyridin-3-ylmethyl)piperidin-4-yl)-5-(1-(4-cyanophenyl)piperidin-4-yloxy)picolinamide | 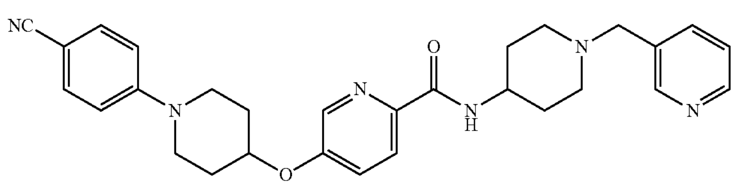 [SMILES: N#Cc1ccc(N2CCC(Oc3ccc(C(=O)NC4CCN(Cc5cccnc5)CC4)nc3)CC2)cc1] |
| 7 | methyl 4-((4-(5-(1-(4-cyanophenyl)piperidin-4-yloxy)picolinamido)piperidin-1-yl)methyl)benzoate | 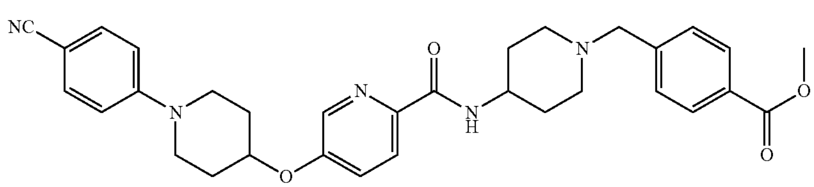 [SMILES: COC(=O)c1ccc(CN2CCC(NC(=O)c3ccc(OC4CCN(c5ccc(C#N)cc5)CC4)cn3)CC2)cc1] |
| 8 | methyl 4-((4-(5-(1-(4-(trifluoromethyl)phenyl)piperidin-4-yloxy)picolinamido)piperidin-1-yl)methyl)benzoate | 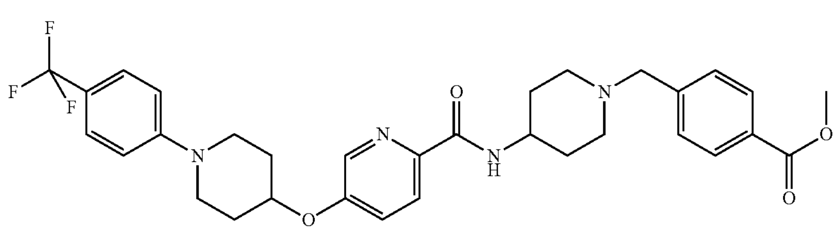 [SMILES: COC(=O)c1ccc(CN2CCC(NC(=O)c3ccc(OC4CCN(c5ccc(C(F)(F)F)cc5)CC4)cn3)CC2)cc1] |

TABLE 1-continued

| No. | Name | Structure |
|---|---|---|
| 9 | tert-butyl 4-(6-(1-(4-(trifluoromethyl)phenyl)piperidin-4-yloxy)nicotinamido)piperidine-1-carboxylate | 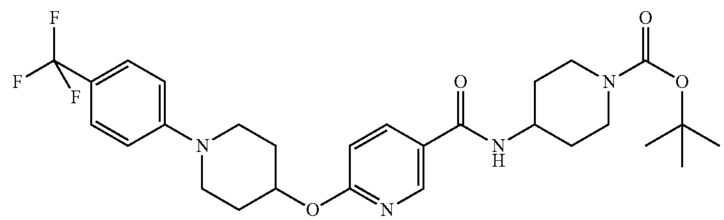 [SMILES: CC(C)(C)OC(=O)N1CCC(NC(=O)c2ccc(OC3CCN(c4ccc(C(F)(F)F)cc4)CC3)nc2)CC1] |
| 10 | N-(1-(pyridin-4-ylmethyl)piperidin-4-yl)-6-(1-(4-(trifluoromethyl)phenyl)piperidin-4-yloxy)nicotinamide | 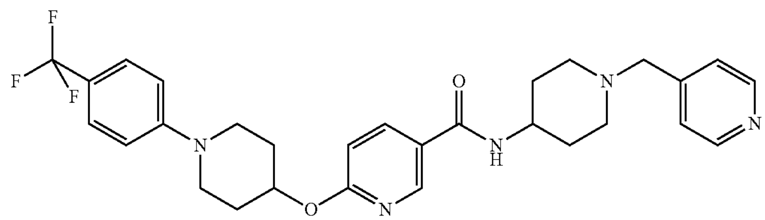 [SMILES: O=C(NC1CCN(Cc2ccncc2)CC1)c1ccc(OC2CCN(c3ccc(C(F)(F)F)cc3)CC2)nc1] |
| 11 | N-(1-(4-fluorobenzyl)piperidin-4-yl)-6-(1-(4-(trifluoromethyl)phenyl)piperidin-4-yloxy)nicotinamide | 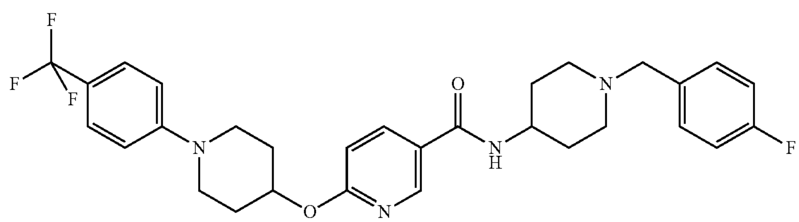 [SMILES: O=C(NC1CCN(Cc2ccc(F)cc2)CC1)c1ccc(OC2CCN(c3ccc(C(F)(F)F)cc3)CC2)nc1] |
| 12 | tert-butyl 4-(4-(1-(4-(trifluoromethyl)phenyl)piperidin-4-yloxy)picolinamido)piperidine-1-carboxylate | 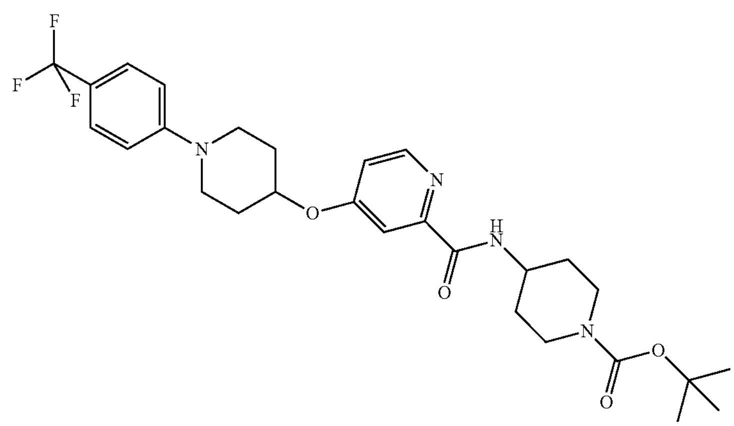 [SMILES: CC(C)(C)OC(=O)N1CCC(NC(=O)c2cc(OC3CCN(c4ccc(C(F)(F)F)cc4)CC3)ccn2)CC1] |
| 13 | N-(1-(pyridin-4-ylmethyl)piperidin-4-yl)-4-(1-(4-(trifluoromethyl)phenyl)piperidin-4-yloxy)picolinamide | 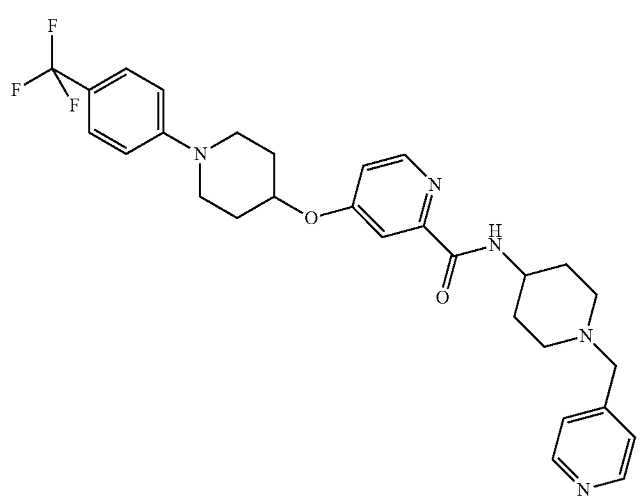 [SMILES: O=C(NC1CCN(Cc2ccncc2)CC1)c1cc(OC2CCN(c3ccc(C(F)(F)F)cc3)CC2)ccn1] |

TABLE 1-continued
| No. | Name | Structure |
|---|---|---|
| 14 | N-(1-(pyridin-4-ylmethyl)piperidin-4-yl)-5-(1-(4-(trifluoromethyl)phenyl)piperidin-4-yloxy)nicotinamide | 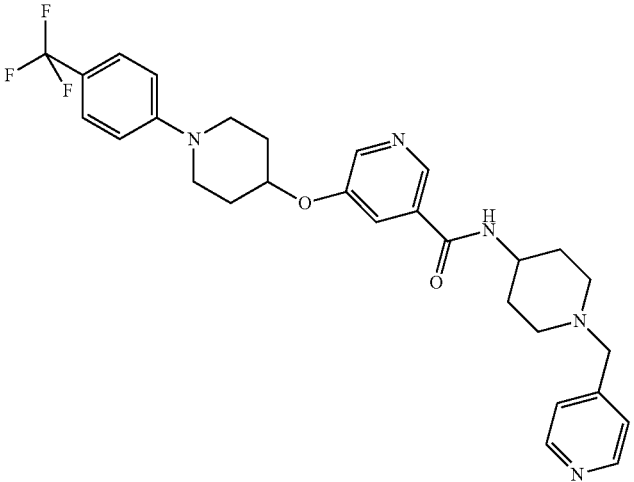 [SMILES: O=C(NC1CCN(Cc2ccncc2)CC1)c1cncc(OC2CCN(c3ccc(C(F)(F)F)cc3)CC2)c1] |
| 15 | tert-butyl 4-(2-(1-(4-(trifluoromethyl)phenyl)piperidin-4-yloxy)isonicotinamido)piperidine-1-carboxylate | 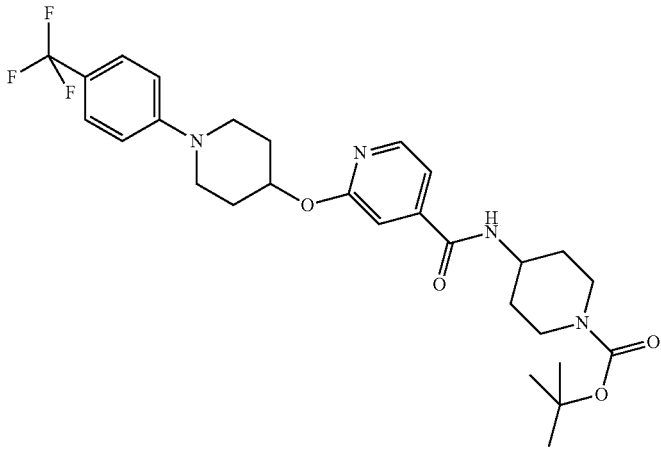 [SMILES: CC(C)(C)OC(=O)N1CCC(NC(=O)c2ccnc(OC3CCN(c4ccc(C(F)(F)F)cc4)CC3)c2)CC1] |
| 16 | N-(1-(4-fluorobenzyl)piperidin-4-yl)-5-(1-(4-(trifluoromethyl)phenyl)piperidin-4-yloxy)nicotinamide | 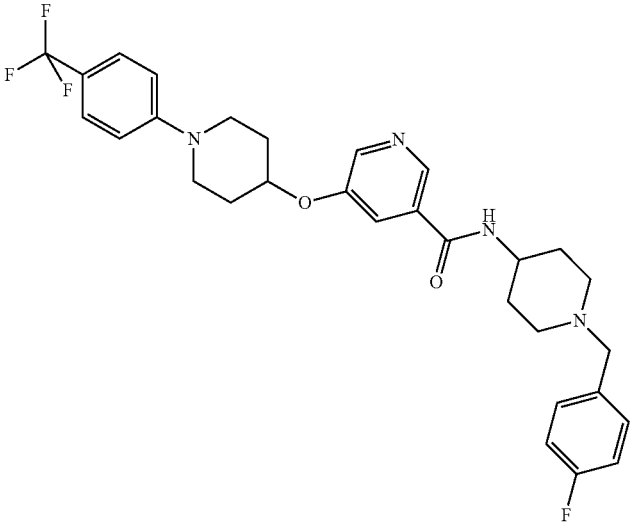 [SMILES: O=C(NC1CCN(Cc2ccc(F)cc2)CC1)c1cncc(OC2CCN(c3ccc(C(F)(F)F)cc3)CC2)c1] |

TABLE 1-continued
| No. | Name | Structure |
|---|---|---|
| 17 | N-(1-(4-cyanobenzyl)piperidin-4-yl)-5-(1-(4-(trifluoromethyl)phenyl)piperidin-4-yloxy)nicotinamide | 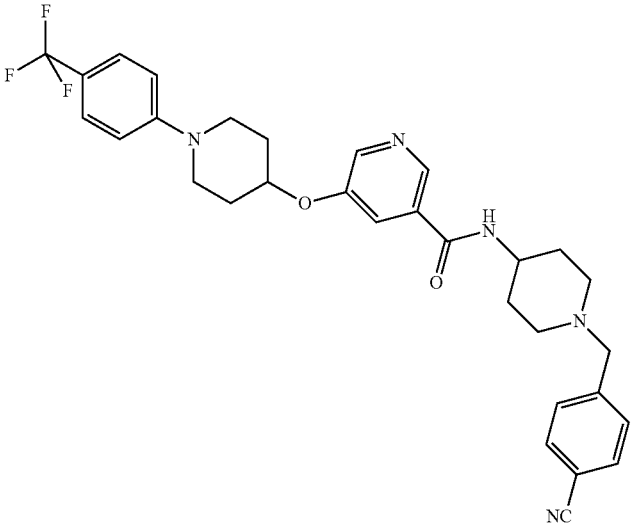 [SMILES: N#Cc1ccc(CN2CCC(NC(=O)c3cncc(OC4CCN(c5ccc(C(F)(F)F)cc5)CC4)c3)CC2)cc1] |
| 18 | N-(1-(pyridin-3-ylmethyl)piperidin-4-yl)-5-(1-(4-(trifluoromethyl)phenyl)piperidin-4-yloxy)nicotinamide | 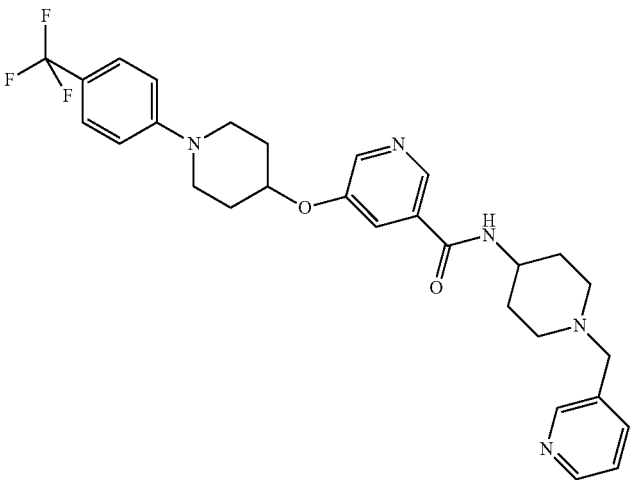 [SMILES: O=C(NC1CCN(Cc2cccnc2)CC1)c1cncc(OC2CCN(c3ccc(C(F)(F)F)cc3)CC2)c1] |
| 19 | N-(piperidin-4-yl)-2-(1-(4-(trifluoromethyl)phenyl)piperidin-4-yloxy)isonicotinamide | 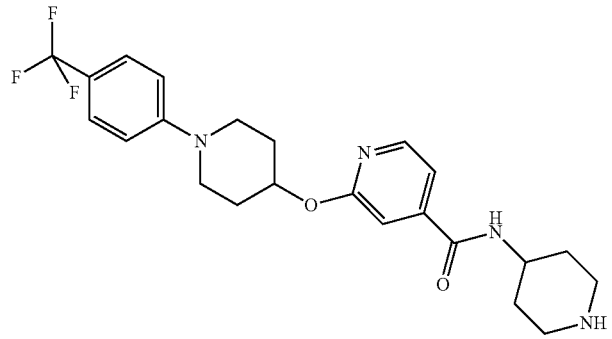 [SMILES: O=C(NC1CCNCC1)c1ccnc(OC2CCN(c3ccc(C(F)(F)F)cc3)CC2)c1] |

TABLE 1-continued

| No. | Name | Structure |
|---|---|---|
| 20 | N-(1-(pyridin-4-ylmethyl)piperidin-4-yl)-2-(1-(4-(trifluoromethyl)phenyl)piperidin-4-yloxy)isonicotinamide | 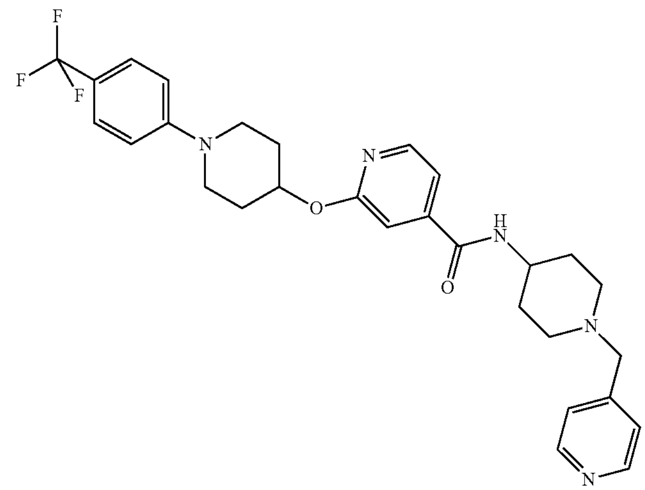 [SMILES: O=C(NC1CCN(Cc2ccncc2)CC1)c1ccnc(OC2CCN(c3ccc(C(F)(F)F)cc3)CC2)c1] |
| 21 | N-(1-(4-cyanobenzyl)piperidin-4-yl)-2-(1-(4-(trifluoromethyl)phenyl)piperidin-4-yloxy)isonicotinamide | 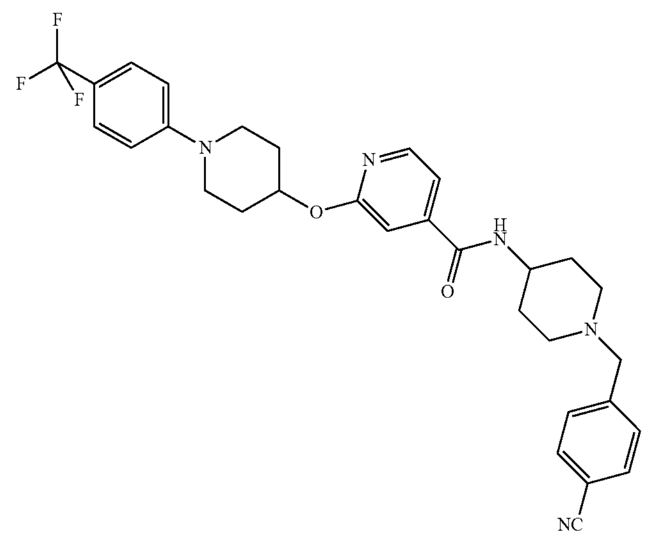 [SMILES: N#Cc1ccc(CN2CCC(NC(=O)c3ccnc(OC4CCN(c5ccc(C(F)(F)F)cc5)CC4)c3)CC2)cc1] |
| 22 | N-(1-(4-fluorobenzyl)piperidin-4-yl)-2-(1-(4-(trifluoromethyl)phenyl)piperidin-4-yloxy)isonicotinamide | 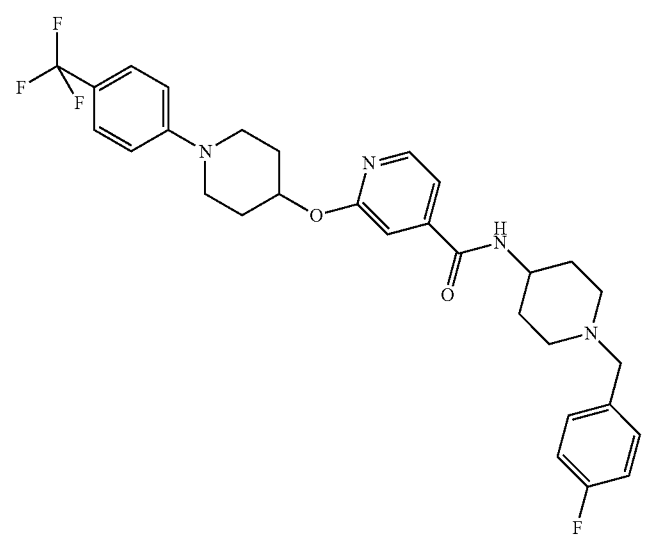 [SMILES: O=C(NC1CCN(Cc2ccc(F)cc2)CC1)c1ccnc(OC2CCN(c3ccc(C(F)(F)F)cc3)CC2)c1] |

TABLE 1-continued

| No. | Name |
|---|---|
| 23 | (R)-tert-butyl 3-(5-(1-(4-(trifluoromethyl)phenyl)piperidin-4-yloxy)picolinamido)pyrrolidine-1-carboxylate |
| 24 | (R)-N-(pyrrolidin-3-yl)-5-(1-(4-(trifluoromethyl)phenyl)piperidin-4-yloxy)picolinamide |
| 25 | (R)-N-(1-(pyridin-4-ylmethyl)pyrrolidin-3-yl)-5-(1-(4-(trifluoromethyl)phenyl)piperidin-4-yloxy)picolinamide |
| 26 | (S)-tert-butyl 3-(5-(1-(4-(trifluoromethyl)phenyl)piperidin-4-yloxy)picolinamido)pyrrolidine-1-carboxylate |
| 27 | (S)-N-(pyrrolidin-3-yl)-5-(1-(4-(trifluoromethyl)phenyl)piperidin-4-yloxy)picolinamide |

TABLE 1-continued

| No. | Name | Structure |
|---|---|---|
| 28 | N-(1-(4-cyanobenzyl)piperidin-4-yl)-4-(1-(4-(trifluoromethyl)phenyl)piperidin-4-yloxy)picolinamide | 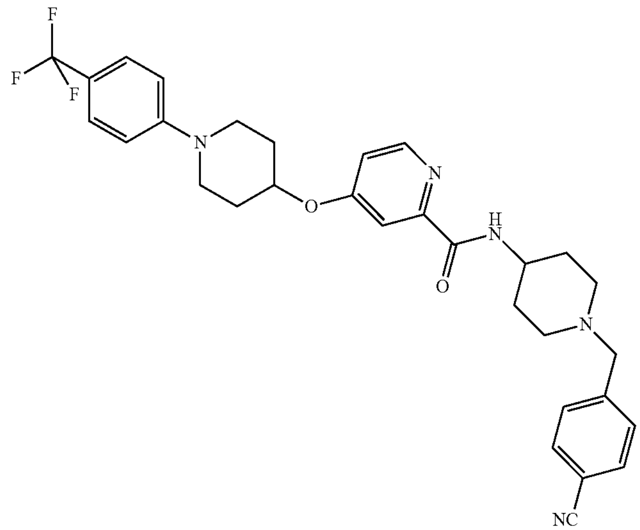 [SMILES: N#Cc1ccc(CN2CCC(NC(=O)c3cc(OC4CCN(c5ccc(C(F)(F)F)cc5)CC4)ccn3)CC2)cc1] |
| 29 | N-(1-(4-fluorobenzyl)piperidin-4-yl)-4-(1-(4-(trifluoromethyl)phenyl)piperidin-4-yloxy)picolinamide | 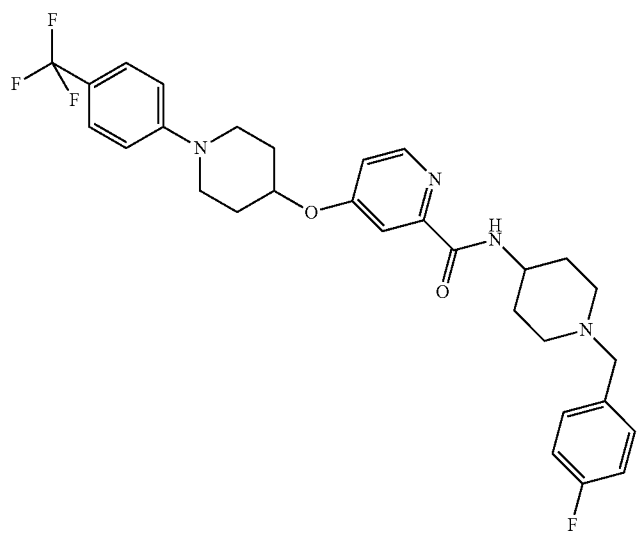 [SMILES: O=C(NC1CCN(Cc2ccc(F)cc2)CC1)c1cc(OC2CCN(c3ccc(C(F)(F)F)cc3)CC2)ccn1] |
| 30 | (S)-N-(1-(pyridin-4-ylmethyl)pyrrolidin-3-yl)-5-(1-(4-(trifluoromethyl)phenyl)piperidin-4-yloxy)picolinamide | 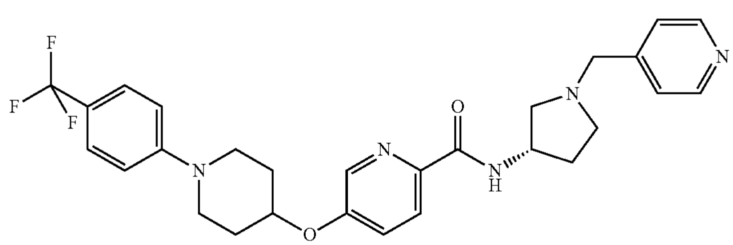 [SMILES: O=C(N[C@H]1CCN(Cc2ccncc2)C1)c1ccc(OC2CCN(c3ccc(C(F)(F)F)cc3)CC2)cn1] |
| 31 | (S)-N-(1-(4-cyanobenzyl)pyrrolidin-3-yl)-5-(1-(4-(trifluoromethyl)phenyl)piperidin-4-yloxy)picolinamide | 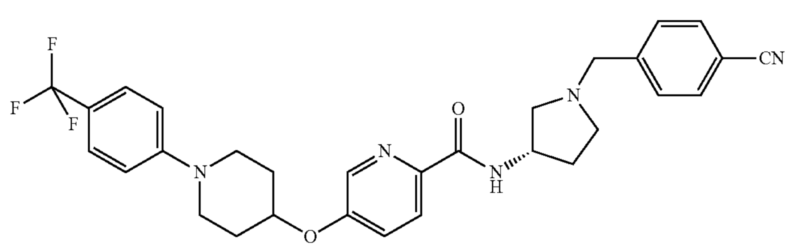 [SMILES: N#Cc1ccc(CN2CC[C@H](NC(=O)c3ccc(OC4CCN(c5ccc(C(F)(F)F)cc5)CC4)cn3)C2)cc1] |

TABLE 1-continued

| No. | Name | Structure |
|---|---|---|
| 32 | (S)-N-(1-(4-fluorobenzyl)pyrrolidin-3-yl)-5-(1-(4-(trifluoromethyl)phenyl)piperidin-4-yloxy)picolinamide | 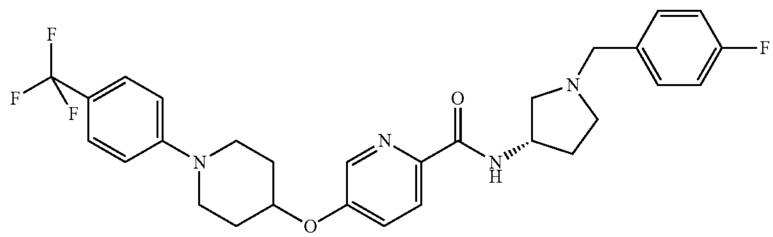 [SMILES: O=C(N[C@H]1CCN(Cc2ccc(F)cc2)C1)c1ccc(OC2CCN(c3ccc(C(F)(F)F)cc3)CC2)cn1] |
| 33 | (R)-N-(1-(4-cyanobenzyl)pyrrolidin-3-yl)-5-(1-(4-(trifluoromethyl)phenyl)piperidin-4-yloxy)picolinamide | 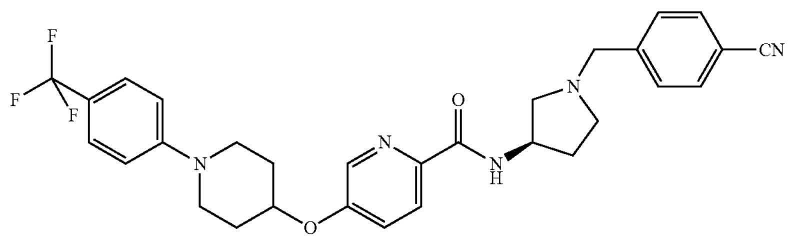 [SMILES: N#Cc1ccc(CN2CC[C@@H](NC(=O)c3ccc(OC4CCN(c5ccc(C(F)(F)F)cc5)CC4)cn3)C2)cc1] |
| 34 | (R)-N-(1-(4-fluorobenzyl)pyrrolidin-3-yl)-5-(1-(4-(trifluoromethyl)phenyl)piperidin-4-yloxy)picolinamide | 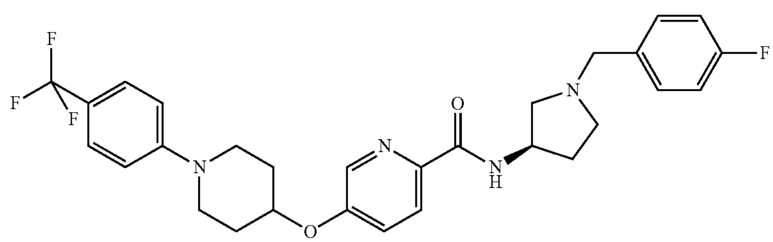 [SMILES: O=C(N[C@@H]1CCN(Cc2ccc(F)cc2)C1)c1ccc(OC2CCN(c3ccc(C(F)(F)F)cc3)CC2)cn1] |
| 35 | N-(1-(4-cyanobenzyl)piperidin-4-yl)-6-(1-(4-(trifluoromethyl)phenyl)piperidin-4-yloxy)nicotinamide | 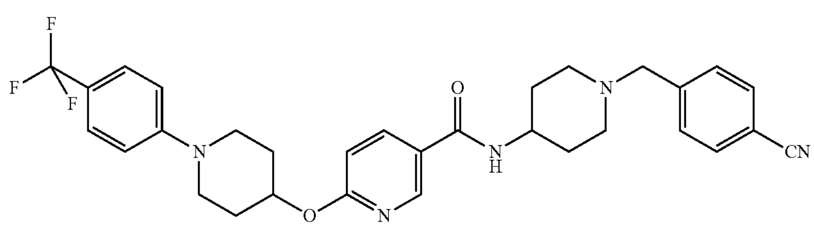 [SMILES: N#Cc1ccc(CN2CCC(NC(=O)c3ccc(OC4CCN(c5ccc(C(F)(F)F)cc5)CC4)nc3)CC2)cc1] |
| 36 | N-(1-phenethylpiperidin-4-yl)-5-(1-(4-(trifluoromethyl)phenyl)piperidin-4-yloxy)picolinamide | 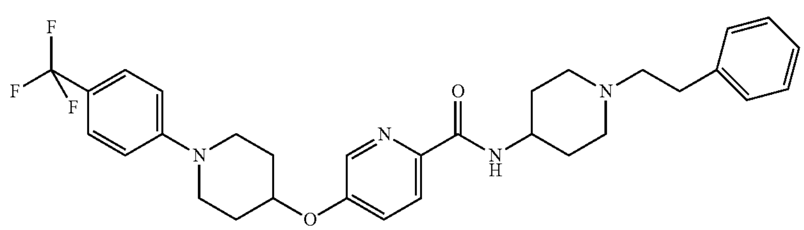 [SMILES: O=C(NC1CCN(CCc2ccccc2)CC1)c1ccc(OC2CCN(c3ccc(C(F)(F)F)cc3)CC2)cn1] |
| 37 | N-(1-(naphthalen-2-ylmethyl)piperidin-4-yl)-5-(1-(4-(trifluoromethyl)phenyl)piperidin-4-yloxy)picolinamide | 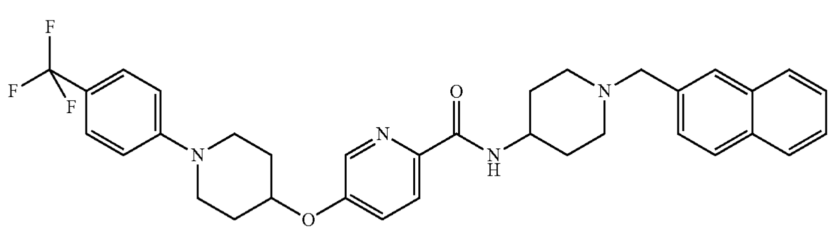 [SMILES: O=C(NC1CCN(Cc2ccc3ccccc3c2)CC1)c1ccc(OC2CCN(c3ccc(C(F)(F)F)cc3)CC2)cn1] |

TABLE 1-continued

| No. | Name | Structure |
|---|---|---|
| 38 | N-(1-benzylpiperidin-4-yl)-5-(1-(4-(trifluoromethyl)phenyl)piperidin-4-yloxy)picolinamide | 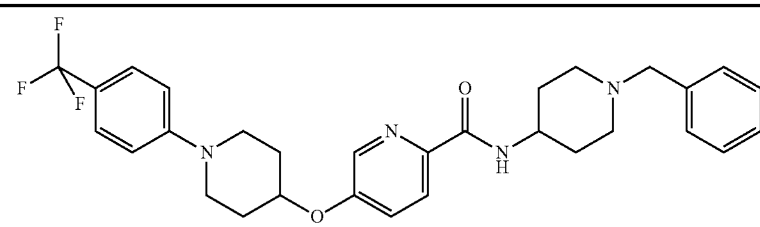 |
| 39 | N-(1-(4-(dimethylamino)benzyl)piperidin-4-yl)-5-(1-(4-(trifluoromethyl)phenyl)piperidin-4-yloxy)picolinamide | 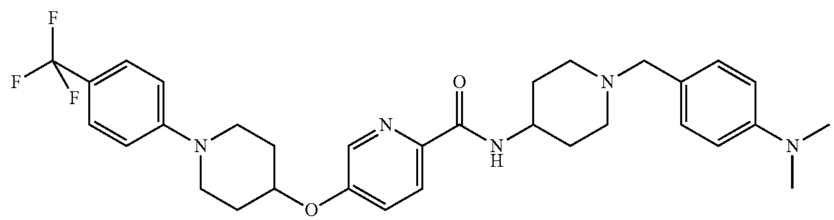 [SMILES: CN(C)c1ccc(CN2CCC(NC(=O)c3ccc(OC4CCN(c5ccc(C(F)(F)F)cc5)CC4)cn3)CC2)cc1] |
| 40 | N-(1-(4-morpholinobenzyl)piperidin-4-yl)-5-(1-(4-(trifluoromethyl)phenyl)piperidin-4-yloxy)picolinamide | 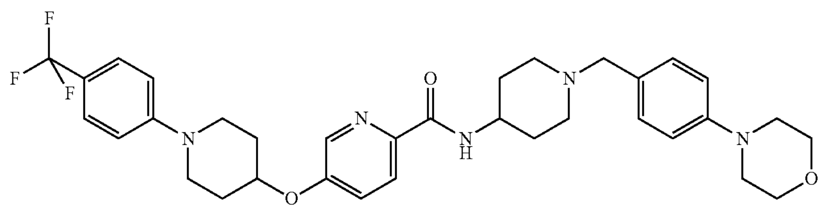 [SMILES: O=C(NC1CCN(Cc2ccc(N3CCOCC3)cc2)CC1)c1ccc(OC2CCN(c3ccc(C(F)(F)F)cc3)CC2)cn1] |
| 41 | N-(1-(4-cyanobenzyl)azetidin-3-yl)-5-(1-(4-(trifluoromethyl)phenyl)piperidin-4-yloxy)picolinamide | 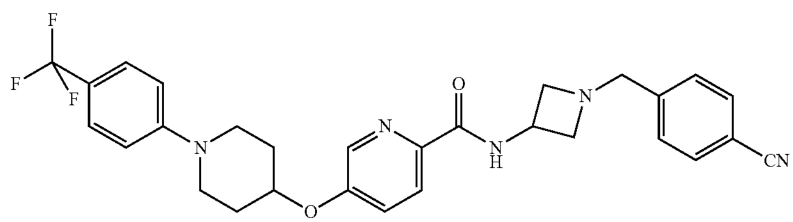 [SMILES: N#Cc1ccc(CN2CC(NC(=O)c3ccc(OC4CCN(c5ccc(C(F)(F)F)cc5)CC4)cn3)C2)cc1] |
| 42 | N-(1-(pyridin-4-ylmethyl)azetidin-3-yl)-5-(1-(4-(trifluoromethyl)phenyl)piperidin-4-yloxy)picolinamide | 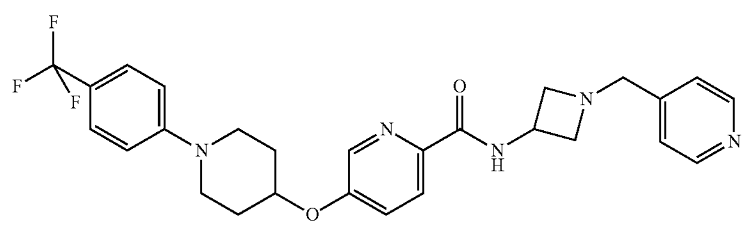 [SMILES: O=C(NC1CN(Cc2ccncc2)C1)c1ccc(OC2CCN(c3ccc(C(F)(F)F)cc3)CC2)cn1] |
| 43 | N-(1-(pyridin-4-ylmethyl)piperidin-4-yl)-6-(1-(4-(trifluoromethyl)phenyl)piperidin-4-yloxy)picolinamide | 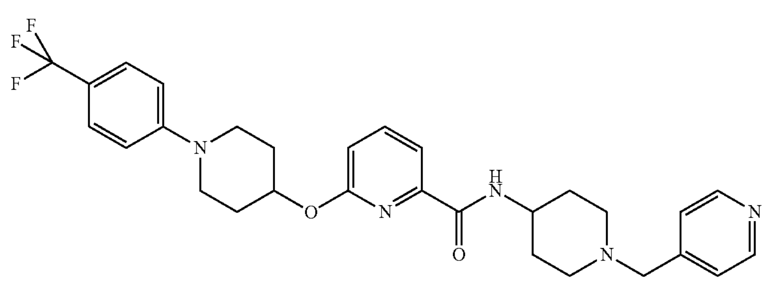 [SMILES: O=C(NC1CCN(Cc2ccncc2)CC1)c1cccc(OC2CCN(c3ccc(C(F)(F)F)cc3)CC2)n1] |
| 44 | N-(1-(pyrimidin-5-ylmethyl)piperidin-4-yl)-5-(1-(4-(trifluoromethyl)phenyl)piperidin-4-yloxy)picolinamide | 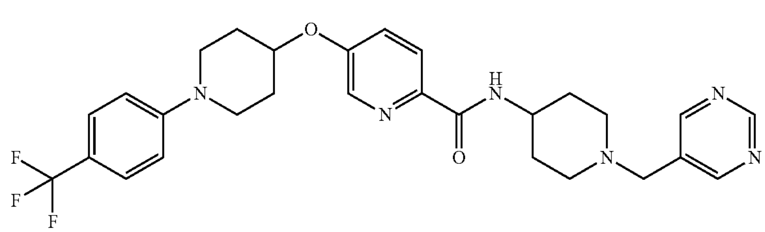 [SMILES: O=C(NC1CCN(Cc2cncnc2)CC1)c1ccc(OC2CCN(c3ccc(C(F)(F)F)cc3)CC2)cn1] |

TABLE 1-continued

| No. | Name | Structure |
|---|---|---|
| 45 | methyl 4-((4-(6-(1-(4-(trifluoromethyl)phenyl)piperidin-4-yloxy)nicotinamido)piperidin-1-yl)methyl)benzoate | 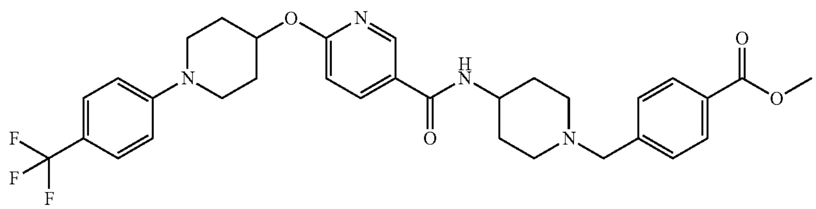 [SMILES: COC(=O)c1ccc(CN2CCC(NC(=O)c3ccc(OC4CCN(c5ccc(C(F)(F)F)cc5)CC4)nc3)CC2)cc1] |
| 46 | 4-((4-(6-(1-(4-(trifluoromethyl)phenyl)piperidin-4-yloxy)nicotinamido)piperidin-1-yl)methyl)benzoic acid | 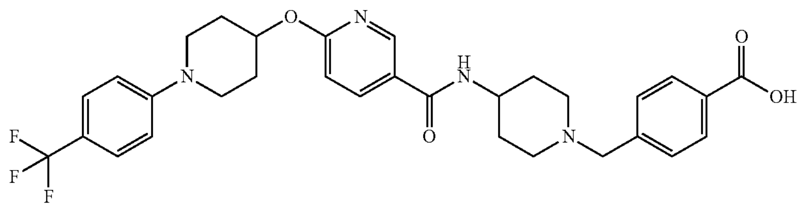 [SMILES: O=C(O)c1ccc(CN2CCC(NC(=O)c3ccc(OC4CCN(c5ccc(C(F)(F)F)cc5)CC4)nc3)CC2)cc1] |
| 47 | 5-(1-(4-(trifluoromethyl)phenyl)piperidin-4-yloxy)-N-(1-((1-trityl-1H-imidazol-4-yl)methyl)piperidin-4-yl)picolinamide | 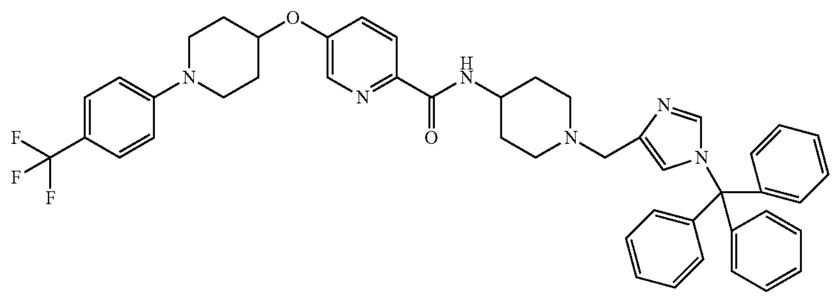 [SMILES: O=C(NC1CCN(Cc2cn(C(c3ccccc3)(c3ccccc3)c3ccccc3)cn2)CC1)c1ccc(OC2CCN(c3ccc(C(F)(F)F)cc3)CC2)cn1] |
| 48 | N-(1-((1H-imidazol-4-yl)methyl)piperidin-4-yl)-5-(1-(4-(trifluoromethyl)phenyl)piperidin-4-yloxy)picolinamide | 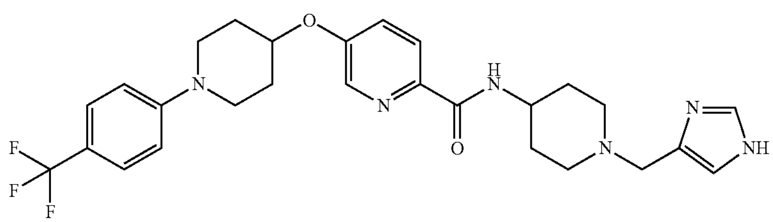 [SMILES: O=C(NC1CCN(Cc2c[nH]cn2)CC1)c1ccc(OC2CCN(c3ccc(C(F)(F)F)cc3)CC2)cn1] |
| 49 | tert-butyl 3-(5-(1-(4-(trifluoromethyl)phenyl)piperidin-4-yloxy)picolinamido)propyl-carbamate | 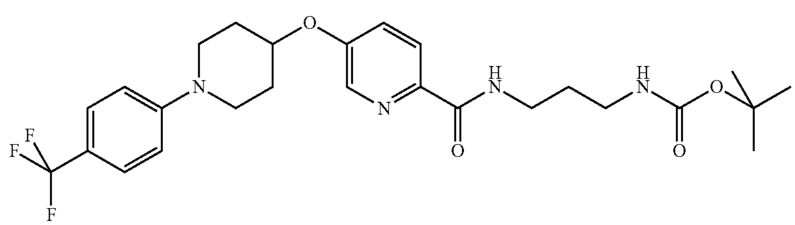 [SMILES: CC(C)(C)OC(=O)NCCCNC(=O)c1ccc(OC2CCN(c3ccc(C(F)(F)F)cc3)CC2)cn1] |
| 50 | N-(3-(pyridin-4-ylmethylamino)propyl)-5-(1-(4-(trifluoromethyl)phenyl)piperidin-4-yloxy)picolinamide | 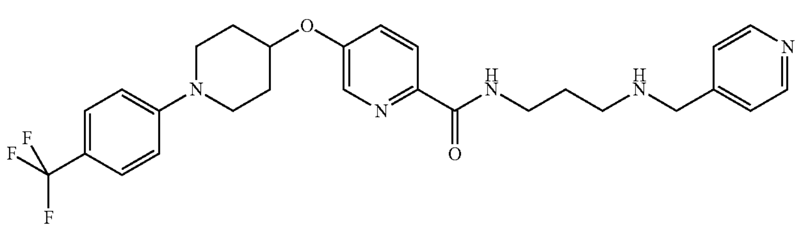 [SMILES: O=C(NCCCNCc1ccncc1)c1ccc(OC2CCN(c3ccc(C(F)(F)F)cc3)CC2)cn1] |
| 51 | N-(1-(pyridin-4-ylmethyl)piperidin-4-yl)-6-(1-(4-(trifluoromethyl)phenyl)piperidin-4-yloxy)pyridine-3-sulfonamide | 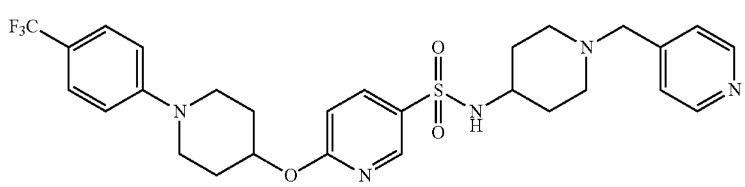 [SMILES: N#Cc1ccc(N2CCC(Oc3ccc(S(=O)(=O)NC4CCN(Cc5ccncc5)CC4)cn3)CC2)cc1] |

TABLE 1-continued

| No. | Name |
|---|---|
| 52 | N-(1-(pyridin-4-ylmethyl)piperidin-4-yl)-6-(1-(4-cyanophenyl)piperidin-4-yloxy)pyridine-3-sulfonamide |
| 53 | 6-(1-(4-cyanobenzyl)piperidin-4-yloxy)-N-(1-(pyridin-4-ylmethyl)piperidin-4-yl)pyridine-3-sulfonamide |
| 54 | tert-butyl 4-(6-(1-(4-(trifluoromethyl)phenyl)piperidin-4-yloxy)pyridine-3-sulfonamido)piperidine-1-carboxylate |
| 55 | N-(piperidin-4-yl)-6-(1-(4-(trifluoromethyl)phenyl)piperidin-4-yloxy)pyridine-3-sulfonamide |
| 56 | N-(1-(4-cyanobenzyl)piperidin-4-yl)-6-(1-(4-(trifluoromethyl)phenyl)piperidin-4-yloxy)pyridine-3-sulfonamide |
| 57 | N-(1-(3-cyanobenzyl)piperidin-4-yl)-6-(1-(4-(trifluoromethyl)phenyl)piperidin-4-yloxy)pyridine-3-sulfonamide |
| 58 | N-(1-(4-(trifluoromethyl)benzyl)piperidin-4-yl)-6-(1-(4-(trifluoromethyl)phenyl)piperidin-4-yloxy)pyridine-3-sulfonamide |
| 59 | N-(1-(3-(trifluoromethyl)benzyl)piperidin-4-yl)-6-(1-(4-(trifluoromethyl)phenyl)piperidin-4-yloxy)pyridine-3-sulfonamide |

TABLE 1-continued

| No. | Name | Structure |
|---|---|---|
| 60 | N-(1-(4-fluorobenzoyl)piperidin-4-yl)-6-(1-(4-(trifluoromethyl)phenyl)piperidin-4-yloxy)pyridine-3-sulfonamide | 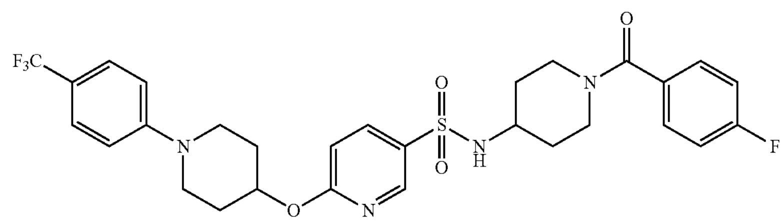 [SMILES: O=C(c1ccc(F)cc1)N1CCC(NS(=O)(=O)c2ccc(OC3CCN(c4ccc(C(F)(F)F)cc4)CC3)nc2)CC1] |
| 61 | tert-butyl 4-(3-methyl-6-(1-(4-(trifluoromethyl)phenyl)piperidin-4-yloxy)benzofuran-2-carboxamido)piperidine-1-carboxylate | 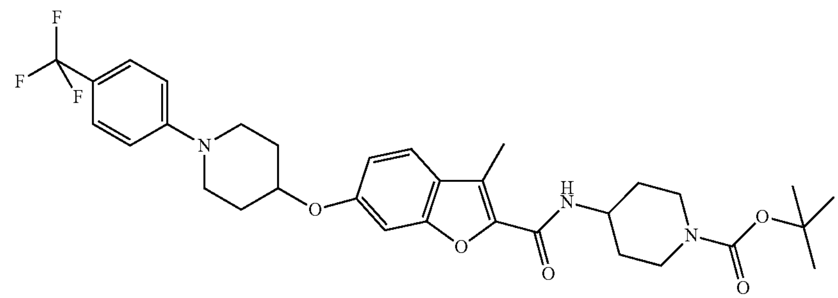 [SMILES: Cc1c(C(=O)NC2CCN(C(=O)OC(C)(C)C)CC2)oc2cc(OC3CCN(c4ccc(C(F)(F)F)cc4)CC3)ccc12] |
| 62 | 3-methyl-N-(piperidin-4-yl)-6-(1-(4-(trifluoromethyl)phenyl)piperidin-4-yloxy)benzofuran-2-carboxamide | 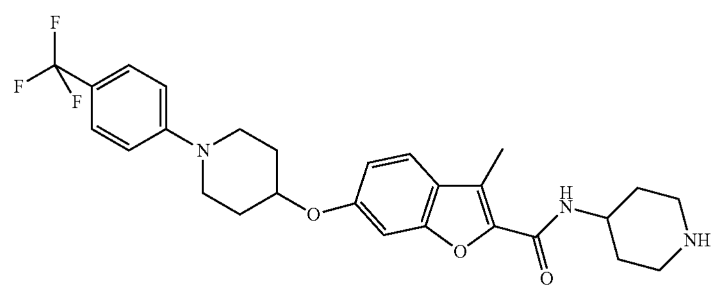 [SMILES: Cc1c(C(=O)NC2CCNCC2)oc2cc(OC3CCN(c4ccc(C(F)(F)F)cc4)CC3)ccc12] |
| 63 | N-(1-(4-fluorobenzyl)piperidin-4-yl)-3-methyl-6-(1-(4-(trifluoromethyl)phenyl)piperidin-4-yloxy)benzofuran-2-carboxamide | 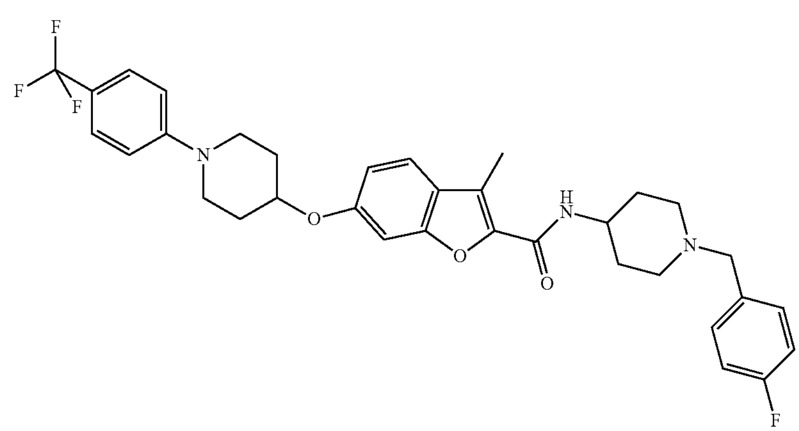 [SMILES: Cc1c(C(=O)NC2CCN(Cc3ccc(F)cc3)CC2)oc2cc(OC3CCN(c4ccc(C(F)(F)F)cc4)CC3)ccc12] |

TABLE 1-continued

| No. | Name | Structure |
|---|---|---|
| 64 | N-(1-(4-cyanobenzyl)piperidin-4-yl)-3-methyl-6-(1-(4-(trifluoromethyl)phenyl)piperidin-4-yloxy)benzofuran-2-carboxamide | 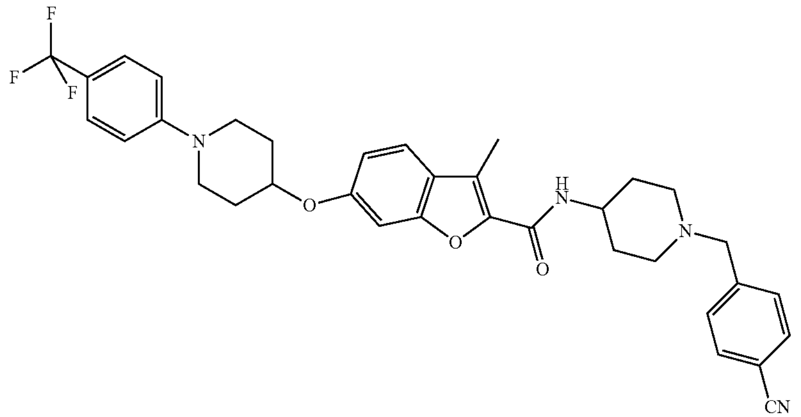 [SMILES: Cc1c(C(=O)NC2CCN(Cc3ccc(C#N)cc3)CC2)oc2cc(OC3CCN(c4ccc(C(F)(F)F)cc4)CC3)ccc12] |
| 65 | 3-methyl-N-(1-(pyridin-4-ylmethyl)piperidin-4-yl)-6-(1-(4-(trifluoromethyl)phenyl)piperidin-4-yloxy)benzofuran-2-carboxamide | 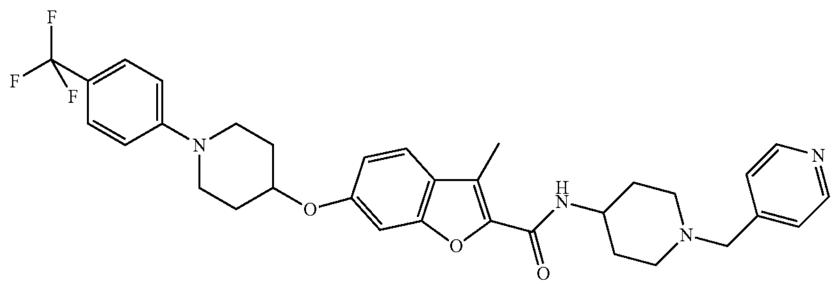 [SMILES: Cc1c(C(=O)NC2CCN(Cc3ccncc3)CC2)oc2cc(OC3CCN(c4ccc(C(F)(F)F)cc4)CC3)ccc12] |
| 66 | N-(1-(3-cyanobenzyl)piperidin-4-yl)-3-methyl-6-(1-(4-(trifluoromethyl)phenyl)piperidin-4-yloxy)benzofuran-2-carboxamide | 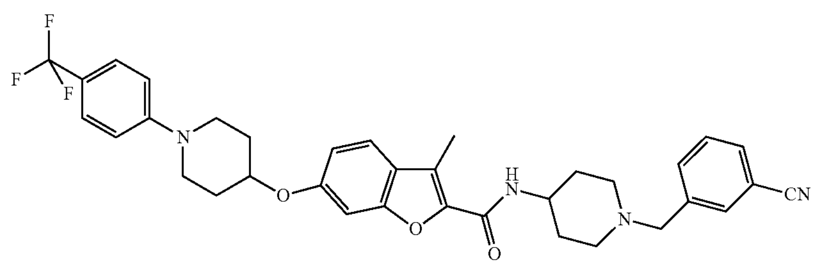 [SMILES: Cc1c(C(=O)NC2CCN(Cc3cccc(C#N)c3)CC2)oc2cc(OC3CCN(c4ccc(C(F)(F)F)cc4)CC3)ccc12] |
| 67 | N-(1-(2-cyanobenzyl)piperidin-4-yl)-3-methyl-6-(1-(4-(trifluoromethyl)phenyl)piperidin-4-yloxy)benzofuran-2-carboxamide | 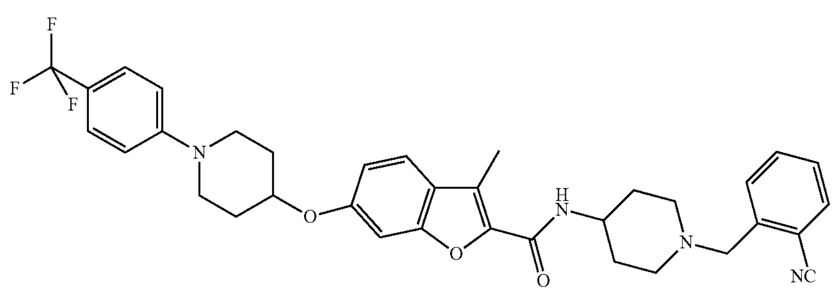 [SMILES: Cc1c(C(=O)NC2CCN(Cc3ccccc3C#N)CC2)oc2cc(OC3CCN(c4ccc(C(F)(F)F)cc4)CC3)ccc12] |
| 68 | 3-methyl-N-(1-(pyridin-2-ylmethyl)piperidin-4-yl)-6-(1-(4-(trifluoromethyl)phenyl)piperidin-4-yloxy)benzofuran-2-carboxamide | 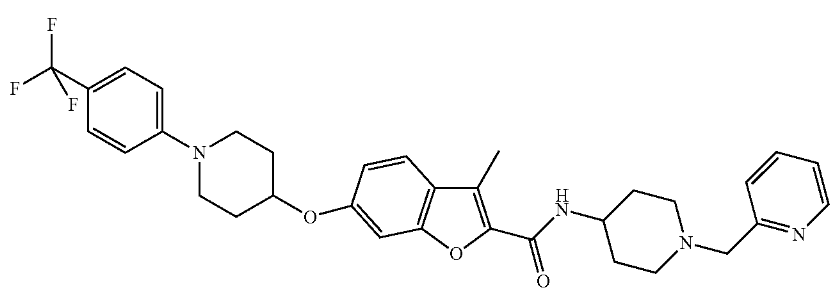 [SMILES: Cc1c(C(=O)NC2CCN(Cc3ccccn3)CC2)oc2cc(OC3CCN(c4ccc(C(F)(F)F)cc4)CC3)ccc12] |

TABLE 1-continued

| No. | Name | Structure |
|---|---|---|
| 69 | 3-methyl-N-(1-(pyridin-3-ylmethyl)piperidin-4-yl)-6-(1-(4-(trifluoromethyl)phenyl)piperidin-4-yloxy)benzofuran-2-carboxamide | 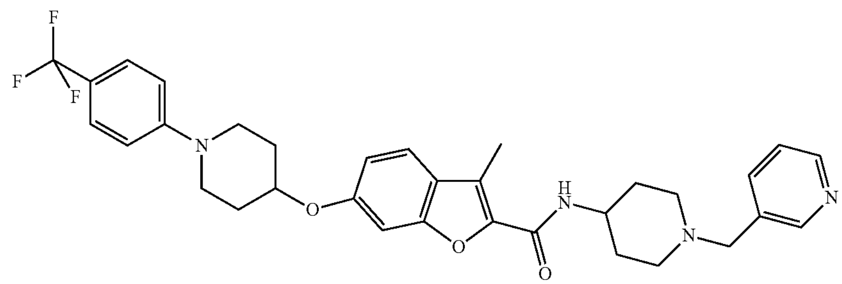 [SMILES: Cc1c(C(=O)NC2CCN(Cc3cccnc3)CC2)oc2cc(OC3CCN(c4ccc(C(F)(F)F)cc4)CC3)ccc12] |
| 70 | N-(1-benzylpiperidin-4-yl)-5-(1-(4-cyanobenzyl)piperidin-4-yloxy)benzofuran-2-carboxamide | 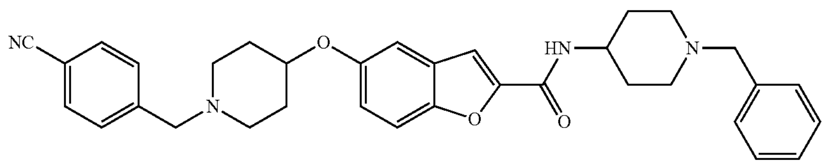 [SMILES: N#Cc1ccc(CN2CCC(Oc3ccc4oc(C(=O)NC5CCN(Cc6ccccc6)CC5)cc4c3)CC2)cc1] |
| 71 | N-(1-benzylpiperidin-4-yl)-5-(1-(4-cyanophenyl)piperidin-4-yloxy)benzofuran-2-carboxamide | 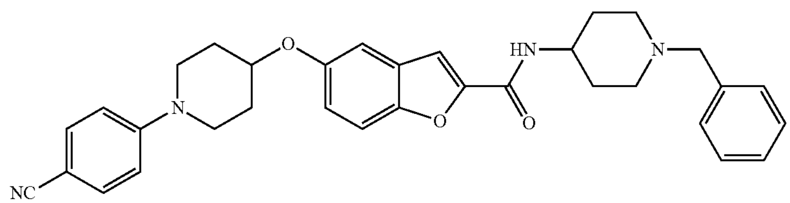 [SMILES: N#Cc1ccc(N2CCC(Oc3ccc4oc(C(=O)NC5CCN(Cc6ccccc6)CC5)cc4c3)CC2)cc1] |
| 72 | N-(1-benzylpiperidin-4-yl)-5-(1-(4-chlorobenzyl)piperidin-4-yloxy)benzofuran-2-carboxamide | 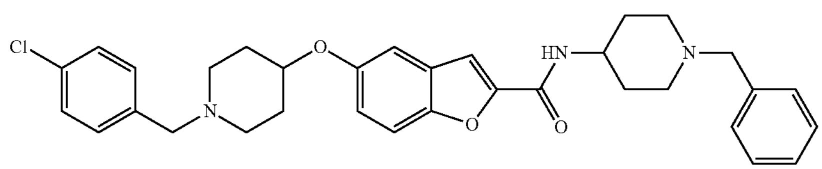 [SMILES: O=C(NC1CCN(Cc2ccccc2)CC1)c1cc2cc(OC3CCN(Cc4ccc(Cl)cc4)CC3)ccc2o1] |
| 73 | N-(1-benzylpiperidin-4-yl)-5-(1-(3-(trifluoromethyl)benzyl)piperidin-4-yloxy)benzofuran-2-carboxamide | 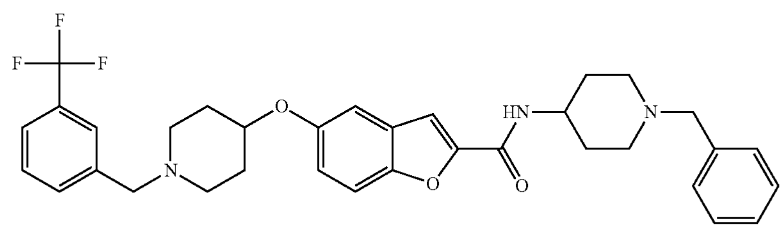 [SMILES: O=C(NC1CCN(Cc2ccccc2)CC1)c1cc2cc(OC3CCN(Cc4cccc(C(F)(F)F)c4)CC3)ccc2o1] |
| 74 | N-(1-benzylpipcridin-4-yl)-5-(1-(3,4-difluorobenzyl)piperidin-4-yloxy)benzofuran-2-carboxamide | 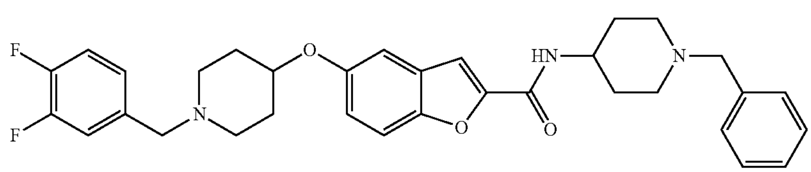 [SMILES: O=C(NC1CCN(Cc2ccccc2)CC1)c1cc2cc(OC3CCN(Cc4ccc(F)c(F)c4)CC3)ccc2o1] |
| 75 | N-(1-benzylpiperidin-4-yl)-5-(1-(4-(trifluoromethyl)phenyl)piperidin-4-yloxy)benzofuran-2-carboxamide | 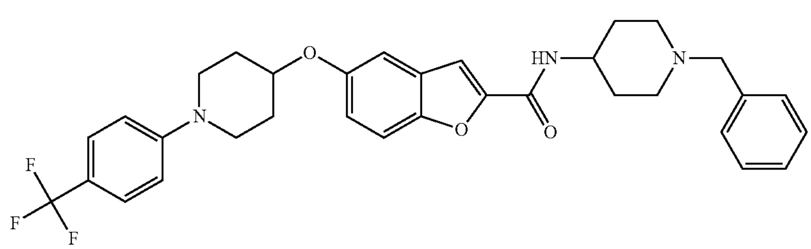 [SMILES: O=C(NC1CCN(Cc2ccccc2)CC1)c1cc2cc(OC3CCN(c4ccc(C(F)(F)F)cc4)CC3)ccc2o1] |

TABLE 1-continued

| No. | Name | Structure |
|---|---|---|
| 76 | N-(1-(pyridin-4-ylmethyl)piperidin-4-yl)-5-(1-(4-(trifluoromethyl)phenyl)piperidin-4-yloxy)benzofuran-2-carboxamide | 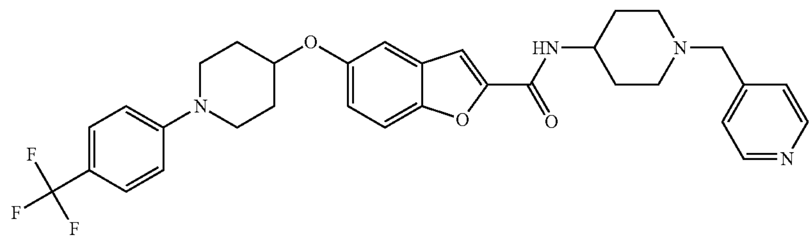 [SMILES: O=C(NC1CCN(Cc2ccncc2)CC1)c1cc2cc(OC3CCN(c4ccc(C(F)(F)F)cc4)CC3)ccc2o1] |
| 77 | 5-(1-(4-chlorobenzyl)piperidin-4-yloxy)-N-(1-(pyridin-4-ylmethyl)piperidin-4-yl)benzofuran-2-carboxamide | 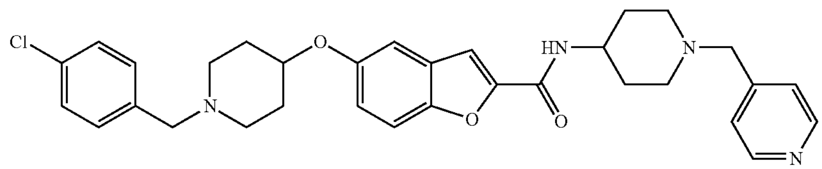 |
| 78 | N-(1-(pyridin-4-ylmethyl)piperidin-4-yl)-5-(1-(4-(trifluoromethoxy)phenyl)piperidin-4-yloxy)benzofuran-2-carboxamide | 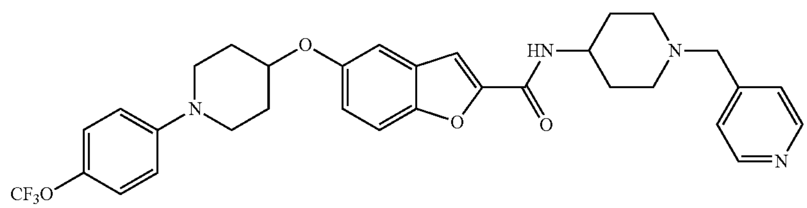 |
| 79 | 5-(1-(4-cyanobenzyl)piperidin-4-yloxy)-N-(1-(pyridin-4-ylmethyl)piperidin-4-yl)benzofuran-2-carboxamide | 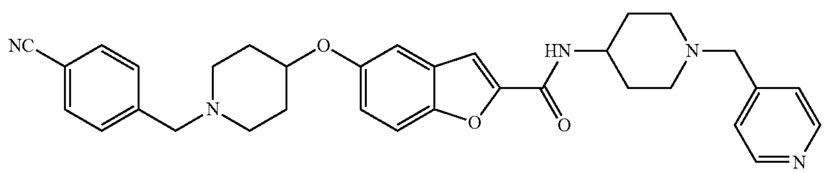 [SMILES: N#Cc1ccc(CN2CCC(Oc3ccc4oc(C(=O)NC5CCN(Cc6ccncc6)CC5)cc4c3)CC2)cc1] |
| 80 | N-(1-benzylpiperidin-4-yl)-5-(1-(4-(trifluoromethoxy)phenyl)piperidin-4-yloxy)benzofuran-2-carboxamide | 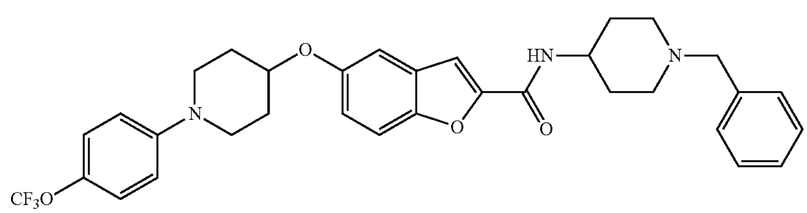 |
| 81 | tert-butyl 4-(6-(1-(4-(trifluoromethoxy)phenyl)piperidin-4-yloxy)benzofuran-2-carboxamido)piperidine-1-carboxylate | 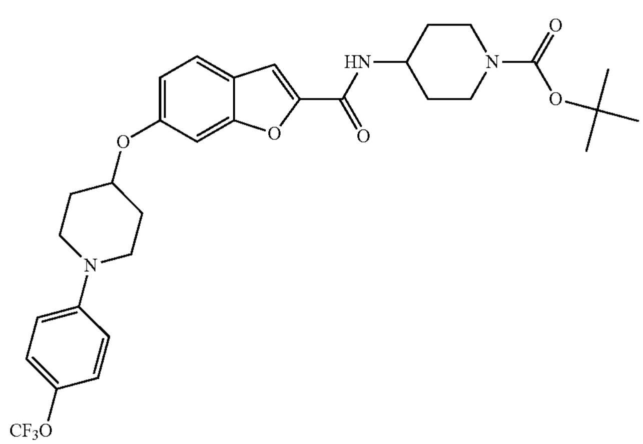 |

TABLE 1-continued

| No. | Name |
|---|---|
| 82 | tert-butyl 4-(6-(1-(4-(trifluoromethyl)phenyl)piperidin-4-yloxy)benzofuran-2-carboxamido)piperidine-1-carboxylate |
| 83 | N-(piperidin-4-yl)-6-(1-(4-(trifluoromethoxy)phenyl)piperidin-4-yloxy)benzofuran-2-carboxamide |
| 84 | N-(piperidin-4-yl)-6-(1-(4-(trifluoromethyl)phenyl)piperidin-4-yloxy)benzofuran-2-carboxamide |
| 85 | tert-butyl 4-(5-(1-(4-(trifluoromethyl)phenyl)piperidin-4-yloxy)benzofuran-2-carboxamido)piperidine-1-carboxylate |
| 86 | N-(piperidin-4-yl)-5-(1-(4-(trifluoromethyl)phenyl)piperidin-4-yloxy)benzofuran-2-carboxamide |
| 87 | N-(1-(pyridin-4-ylmethyl)piperidin-4-yl)-6-(1-(4-(trifluoromethyl)phenyl)piperidin-4-yloxy)benzofuran-2-carboxamide |
| 88 | N-(1-(pyridin-4-ylmethyl)piperidin-4-yl)-6-(1-(4-(trifluoromethoxy)phenyl)piperidin-4-yloxy)benzofuran-2-carboxamide |

TABLE 1-continued

| No. | Name | Structure |
|---|---|---|
| 89 | N-(1-(4-cyanobenzyl)piperidin-4-yl)-6-(1-(4-(trifluoromethoxy)phenyl)piperidin-4-yloxy)benzofuran-2-carboxamide | 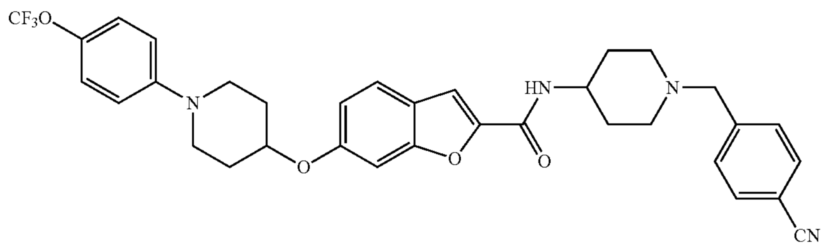 |
| 90 | N-(1-(4-cyanobenzyl)piperidin-4-yl)-6-(1-(4-(trifluoromethyl)phenyl)piperidin-4-yloxy)benzofuran-2-carboxamide | 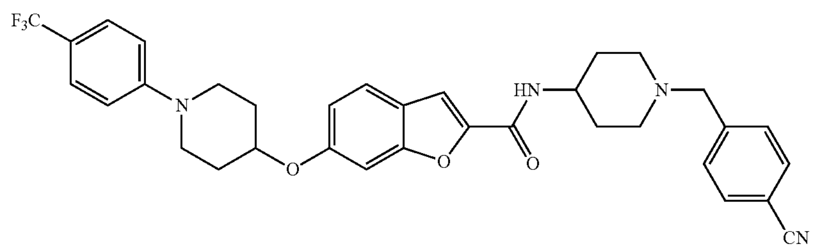 |
| 91 | N-(1-(4-fluorobenzyl)piperidin-4-yl)-6-(1-(4-(trifluoromethyl)phenyl)piperidin-4-yloxy)benzofuran-2-carboxamide | 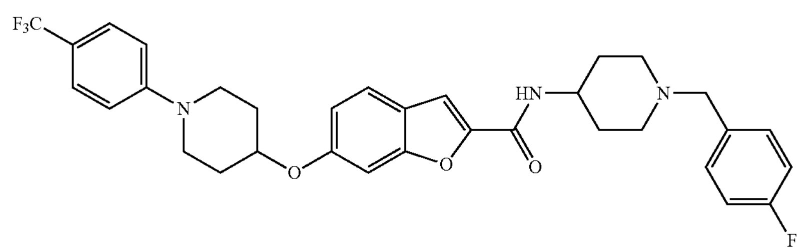 [SMILES: O=C(NC1CCN(Cc2ccc(F)cc2)CC1)c1cc2ccc(OC3CCN(c4ccc(C(F)(F)F)cc4)CC3)cc2o1] |
| 92 | N-(1-(pyridin-2-ylmethyl)piperidin-4-yl)-6-(1-(4-(trifluoromethoxy)phenyl)piperidin-4-yloxy)benzofuran-2-carboxamide | 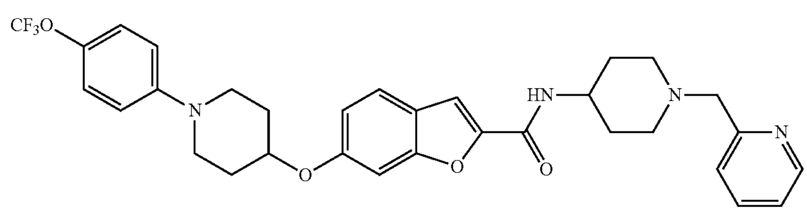 |
| 93 | N-(1-(pyridin-2-ylmethyl)piperidin-4-yl)-6-(1-(4-(trifluoromethyl)phenyl)piperidin-4-yloxy)benzofuran-2-carboxamide | 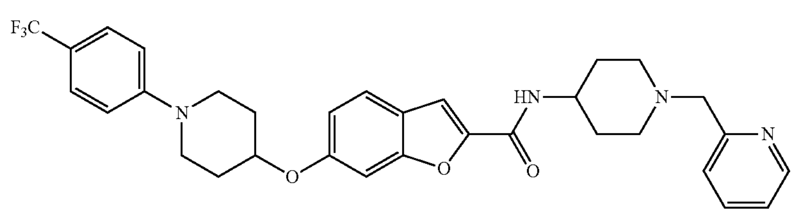 [SMILES: O=C(NC1CCN(Cc2ccccn2)CC1)c1cc2ccc(OC3CCN(c4ccc(C(F)(F)F)cc4)CC3)cc2o1] |
| 94 | N-(1-(4-fluorobenzyl)piperidin-4-yl)-6-(1-(4-(trifluoromethoxy)phenyl)piperidin-4-yloxy)benzofuran-2-carboxamide | 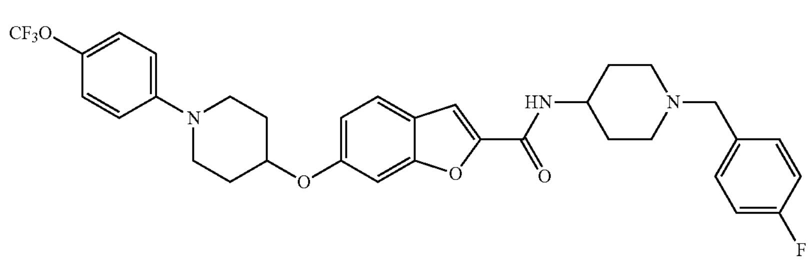 |

TABLE 1-continued

| No. | Name | Structure |
|---|---|---|
| 95 | N-(1-(pyridin-3-ylmethyl)piperidin-4-yl)-6-(1-(4-(trifluoromethoxy)phenyl)piperidin-4-yloxy)benzofuran-2-carboxamide | 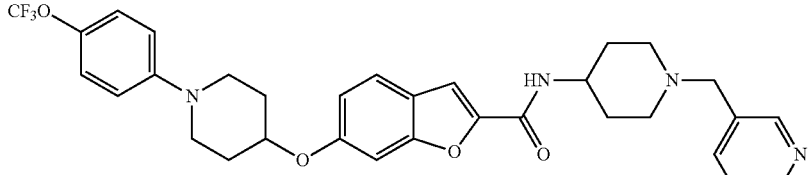 |
| 96 | N-(1-(pyridin-3-ylmethyl)piperidin-4-yl)-6-(1-(4-(trifluoromethyl)phenyl)piperidin-4-yloxy)benzofuran-2-carboxamide | 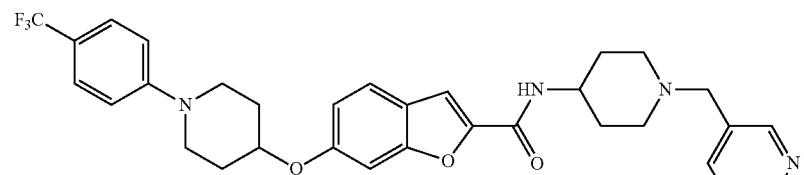 |
| 97 | N-(1-(2-cyanobenzyl)piperidin-4-yl)-6-(1-(4-(trifluoromethoxy)phenyl)piperidin-4-yloxy)benzofuran-2-carboxamide | 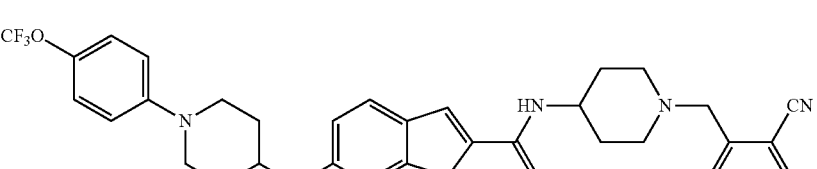 |
| 98 | N-(1-(2-cyanobenzyl)piperidin-4-yl)-6-(1-(4-(trifluoromethyl)phenyl)piperidin-4-yloxy)benzofuran-2-carboxamide | 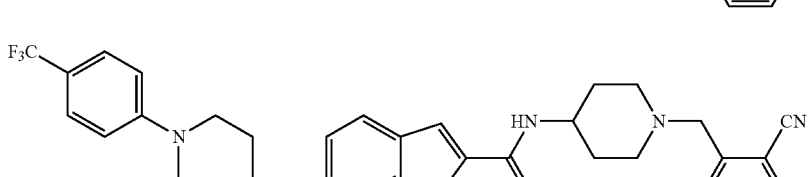 |
| 99 | N-(1-(4-(trifluoromethyl)benzyl)piperidin-4-yl)-6-(1-(4-(trifluoromethyl)phenyl)piperidin-4-yloxy)benzofuran-2-carboxamide | 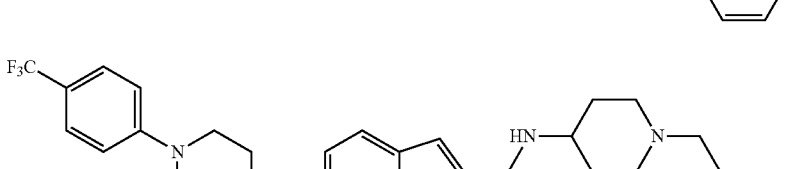 |
| 100 | N-(1-(4-(trifluoromethyl)benzyl)piperidin-4-yl)-5-(1-(4-(trifluoromethyl)phenyl)piperidin-4-yloxy)benzofuran-2-carboxamide | 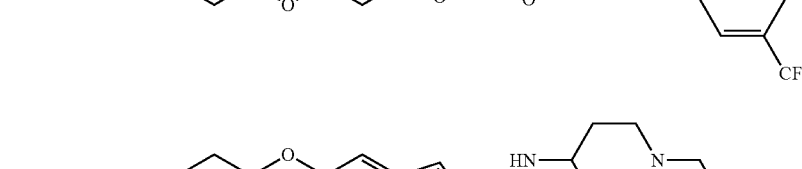 |
| 101 | N-(1-(pyridin-3-ylmethyl)piperidin-4-yl)-5-(1-(4-(trifluoromethyl)phenyl)piperidin-4-yloxy)benzofuran-2-carboxamide | 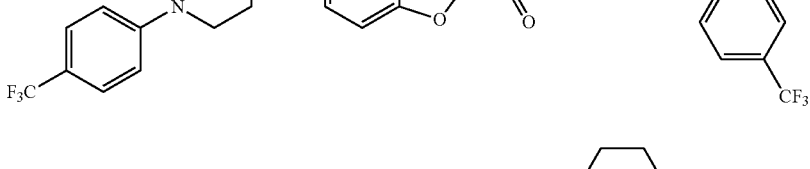 |

TABLE 1-continued

| No. | Name |
|---|---|
| 102 | tert-butyl 4-(N-methyl-5-(1-(4-(trifluoromethyl)phenyl)piperidin-4-yloxy)benzofuran-2-carboxamido)piperidine-1-carboxylate |
| 103 | N-methyl-N-(piperidin-4-yl)-5-(1-(4-(trifluoromethyl)phenyl)piperidin-4-yloxy)benzofuran-2-carboxamide |
| 104 | N-methyl-N-(1-(pyridin-4-ylmethyl)piperidin-4-yl)-5-(1-(4-(trifluoromethyl)phenyl)piperidin-4-yloxy)benzofuran-2-carboxamide |
| 105 | N-(1-(pyridin-4-ylmethyl)piperidin-4-yl)-5-(1-(4-(trifluoromethyl)phenyl)piperidin-4-yloxy)benzofuran-2-carboxamide, formate salt |
| 106 | N-(1-(pyridin-3-ylsulfonyl)piperidin-4-yl)-6-(1-(4-(trifluoromethyl)phenyl)piperidin-4-yloxy)benzofuran-2-carboxamide |
| 107 | N-(1-(4-cyanobenzyl)piperidin-4-yl)-N-methyl-5-(1-(4-(trifluoromethyl)phenyl)piperidin-4-yloxy)benzofuran-2-carboxamide |

TABLE 1-continued

| No. | Name | Structure |
|---|---|---|
| 108 | N-(1-(pyridin-3-ylsulfonyl)piperidin-4-yl)-6-(1-(4-(trifluoromethoxy)phenyl)piperidin-4-yloxy)benzofuran-2-carboxamide | 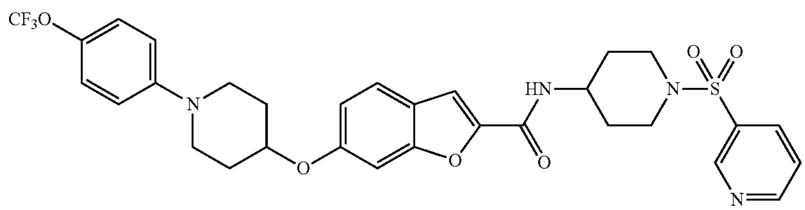 |
| 109 | N-methyl-N-(1-(pyridin-3-ylmethyl)piperidin-4-yl)-5-(1-(4-(trifluoromethyl)phenyl)piperidin-4-yloxy)benzofuran-2-carboxamide | 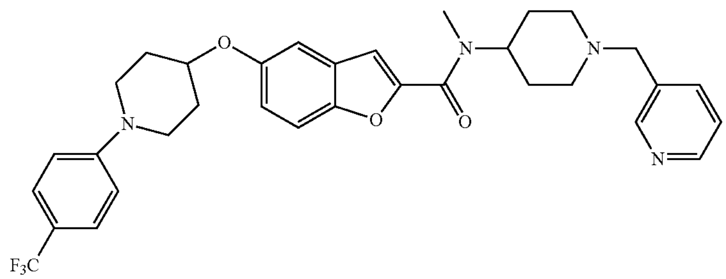 [SMILES: CN(C(=O)c1cc2cc(OC3CCN(c4ccc(C(F)(F)F)cc4)CC3)ccc2o1)C1CCN(Cc2cccnc2)CC1] |
| 110 | N-(1-(3-cyanobenzyl)piperidin-4-yl)-N-methyl-5-(1-(4-(trifluoromethyl)phenyl)piperidin-4-yloxy)benzofuran-2-carboxamide | 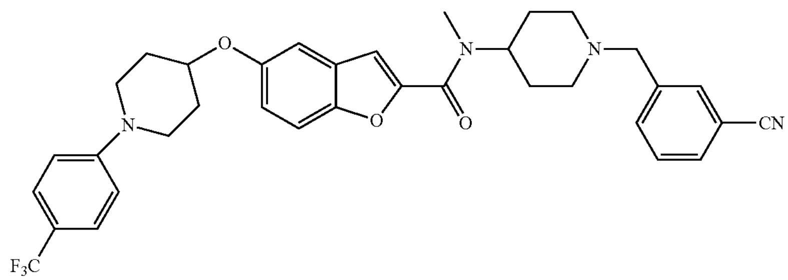 [SMILES: CN(C(=O)c1cc2cc(OC3CCN(c4ccc(C(F)(F)F)cc4)CC3)ccc2o1)C1CCN(Cc2cccc(C#N)c2)CC1] |
| 111 | N-(1-(2-cyanobenzyl)piperidin-4-yl)-N-methyl-5-(1-(4-(trifluoromethyl)phenyl)piperidin-4-yloxy)benzofuran-2-carboxamide | 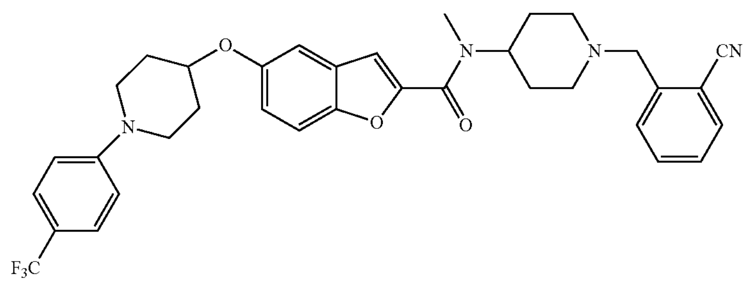 [SMILES: CN(C(=O)c1cc2cc(OC3CCN(c4ccc(C(F)(F)F)cc4)CC3)ccc2o1)C1CCN(Cc2ccccc2C#N)CC1] |
| 112 | N-(1-isonicotinoylpiperidin-4-yl)-6-(1-(4-(trifluoromethyl)phenyl)piperidin-4-yloxy)benzofuran-2-carboxamide | 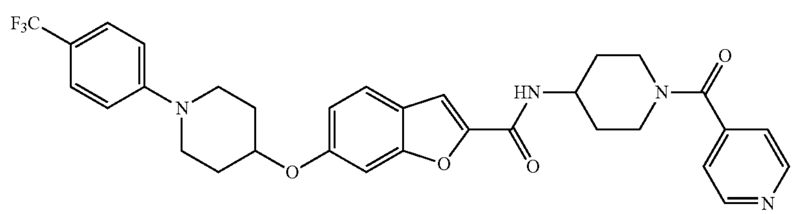 |
| 113 | tert-butyl 4-(5-(1-(4-cyanobenzyl)piperidin-4-yloxy)benzofuran-2-carboxamido)piperidine-1-carboxylate | 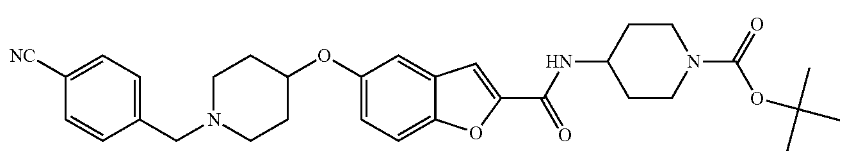 [SMILES: CC(C)(C)OC(=O)N1CCC(NC(=O)c2cc3cc(OC4CCN(Cc5ccc(C#N)cc5)CC4)ccc3o2)CC1] |
| 114 | N-(1-benzylpiperidin-4-yl)-5-(1-(4-cyanobenzyl)piperidin-4-yloxy)benzofuran-2-carboxamide | 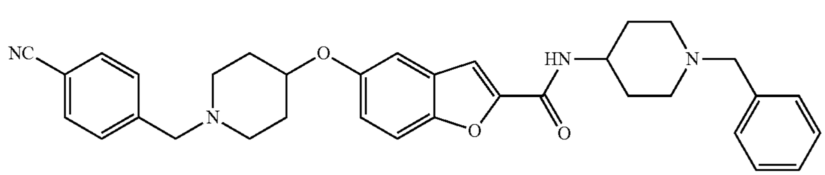 |

TABLE 1-continued

| No. | Name |
|---|---|
| 115 | N-(1-isonicotinoylpiperidin-4-yl)-5-(1-(4-(trifluoromethyl)phenyl)piperidin-4-yloxy)benzofuran-2-carboxamide |
| 116 | N-(1-benzylpiperidin-4-yl)-5-(1-(4-carbamoylbenzyl)piperidin-4-yloxy)benzofuran-2-carboxamide |
| 117 | N-methyl-N-(1-(pyridin-2-ylmethyl)piperidin-4-yl)-5-(1-(4-(trifluoromethyl)phenyl)piperidin-4-yloxy)benzofuran-2-carboxamide |
| 118 | N-(1-isonicotinoylpiperidin-4-yl)-N-methyl-5-(1-(4-(trifluoromethyl)phenyl)piperidin-4-yloxy)benzofuran-2-carboxamide |
| 119 | N-methyl-N-(1-(4-(trifluoromethyl)benzyl)piperidin-4-yl)-5-(1-(4-(trifluoromethyl)phenyl)piperidin-4-yloxy)benzofuran-2-carboxamide |
| 120 | (R)-tert-butyl 3-(5-(1-(4-(trifluoromethyl)phenyl)piperidin-4-yloxy)benzofuran-2-carboxamido)pyrrolidine-1-carboxylate |

TABLE 1-continued

| No. | Name | Structure |
|---|---|---|
| 121 | (R)-N-(pyrrolidin-3-yl)-5-(1-(4-(trifluoromethyl)phenyl)piperidin-4-yloxy)benzofuran-2-carboxamide | 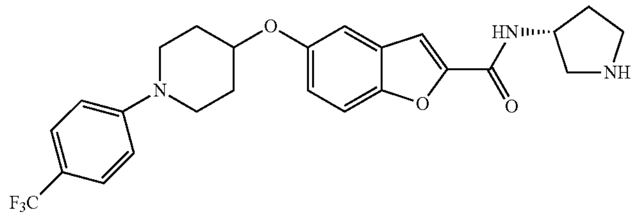 [SMILES: O=C(N[C@@H]1CCNC1)c1cc2cc(OC3CCN(c4ccc(C(F)(F)F)cc4)CC3)ccc2o1] |
| 122 | (R)-N-(1-(pyridin-4-ylmethyl)pyrrolidin-3-yl)-5-(1-(4-(trifluoromethyl)phenyl)piperidin-4-yloxy)benzofuran-2-carboxamide | 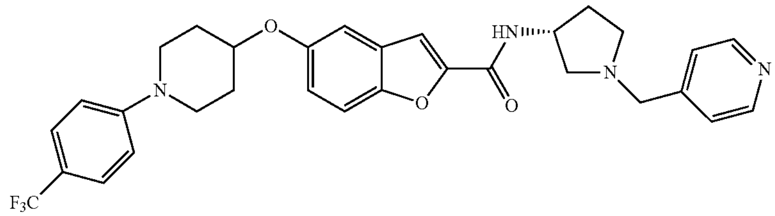 [SMILES: O=C(N[C@@H]1CCN(Cc2ccncc2)C1)c1cc2cc(OC3CCN(c4ccc(C(F)(F)F)cc4)CC3)ccc2o1] |
| 123 | (R)-N-(1-(pyridin-3-ylmethyl)pyrrolidin-3-yl)-5-(1-(4-(trifluoromethyl)phenyl)piperidin-4-yloxy)benzofuran-2-carboxamide | 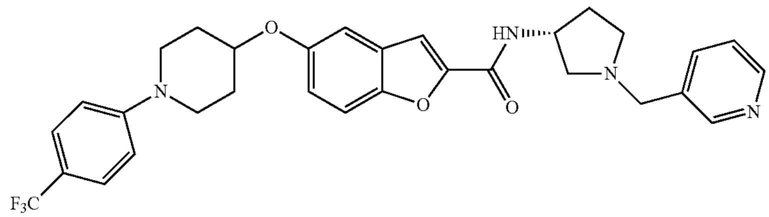 |
| 124 | (R)-N-(1-(pyridin-2-ylmethyl)pyrrolidin-3-yl)-5-(1-(4-(trifluoromethyl)phenyl)piperidin-4-yloxy)benzofuran-2-carboxamide | 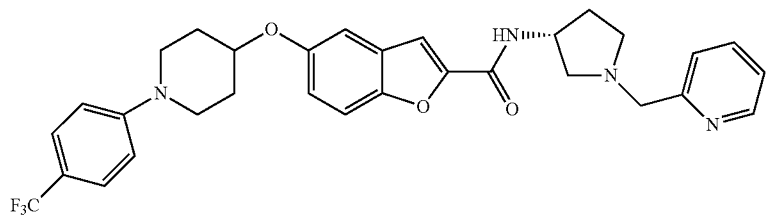 [SMILES: O=C(N[C@@H]1CCN(Cc2ccccn2)C1)c1cc2cc(OC3CCN(c4ccc(C(F)(F)F)cc4)CC3)ccc2o1] |
| 125 | (R)-N-(1-isonicotinoylpyrrolidin-3-yl)-5-(1-(4-(trifluoromethyl)phenyl)piperidin-4-yloxy)benzofuran-2-carboxamide | 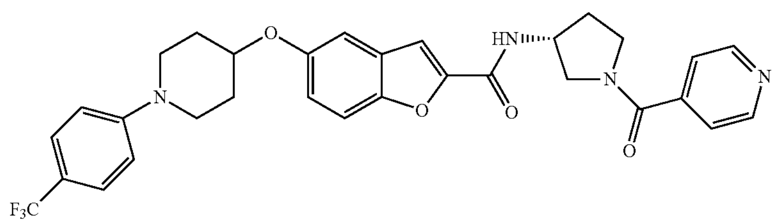 [SMILES: O=C(N[C@@H]1CCN(C(=O)c2ccncc2)C1)c1cc2cc(OC3CCN(c4ccc(C(F)(F)F)cc4)CC3)ccc2o1] |
| 126 | (R)-N-(1-(pyridin-3-ylsulfonyl)pyrrolidin-3-yl)-5-(1-(4-(trifluoromethyl)phenyl)piperidin-4-yloxy)benzofuran-2-carboxamide | 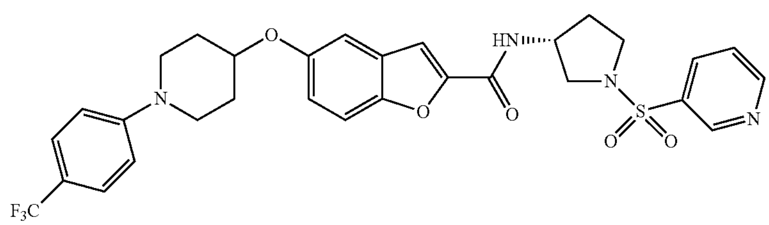 [SMILES: O=C(N[C@@H]1CCN(S(=O)(=O)c2cccnc2)C1)c1cc2cc(OC3CCN(c4ccc(C(F)(F)F)cc4)CC3)ccc2o1] |
| 127 | (S)-tert-butyl 3-(5-(1-(4-chlorobenzyl)piperidin-4-yloxy)benzofuran-2-carboxamido)pyrrolidine-1-carboxylate | 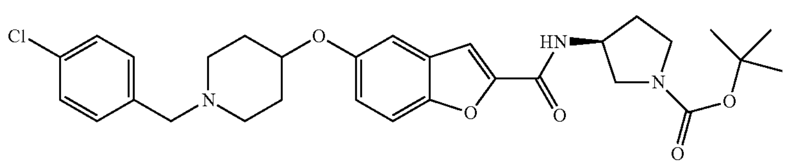 [SMILES: CC(C)(C)OC(=O)N1CC[C@H](NC(=O)c2cc3cc(OC4CCN(Cc5ccc(Cl)cc5)CC4)ccc3o2)C1] |

TABLE 1-continued

| No. | Name |
|---|---|
| 128 | (S)-5-(1-(4-chlorobenzyl)piperidin-4-yloxy)-N-(pyrrolidin-3-yl)benzofuran-2-carboxamide |
| 129 | (S)-5-(1-(4-chlorobenzyl)piperidin-4-yloxy)-N-(1-(pyridin-4-ylmethyl)pyrrolidin-3-yl)benzofuran-2-carboxamide |
| 130 | (S)-5-(1-(4-chlorobenzyl)piperidin-4-yloxy)-N-(1-(pyridin-3-ylmethyl)pyrrolidin-3-yl)benzofuran-2-carboxamide |
| 131 | 5-(1-(4-carbamoylbenzyl)piperidin-4-yloxy)-N-(1-(pyridin-4-ylmethyl)piperidin-4-yl)benzofuran-2-carboxamide |
| 132 | 5-(1-(4-carbamoylbenzyl)piperidin-4-yloxy)-N-(1-isonicotinoylpiperidin-4-yl)benzofuran-2-carboxamide |
| 133 | 5-(1-(4-carbamoylbenzyl)piperidin-4-yloxy)-N-(1-(4-cyanobenzyl)piperidin-4-yl)benzofuran-2-carboxamide |
| 134 | 5-(1-(4-carbamoylphenyl)piperidin-4-yloxy)-N-(1-(pyridin-4-ylmethyl)piperidin-4-yl)benzofuran-2-carboxamide |

TABLE 1-continued

| No. | Name | Structure |
|---|---|---|
| 135 | 5-(1-(4-carbamoylphenyl)piperidin-4-yloxy)-N-(1-isonicotinoylpiperidin-4-yl)benzofuran-2-carboxamide | 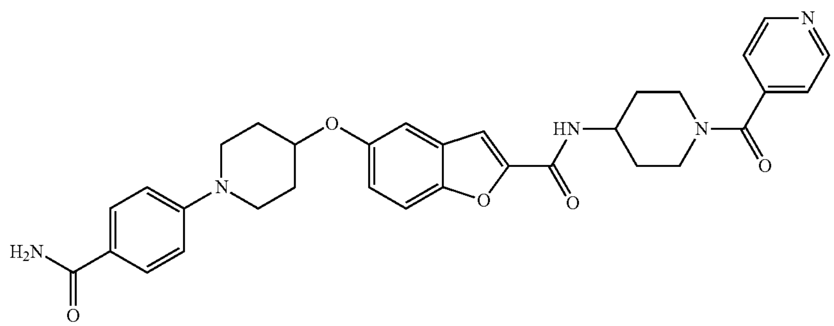 [SMILES: NC(=O)c1ccc(N2CCC(Oc3ccc4oc(C(=O)NC5CCN(C(=O)c6ccncc6)CC5)cc4c3)CC2)cc1] |
| 136 | 5-(1-(4-carbamoylphenyl)piperidin-4-yloxy)-N-(1-(4-cyanobenzyl)piperidin-4-yl)benzofuran-2-carboxamide | 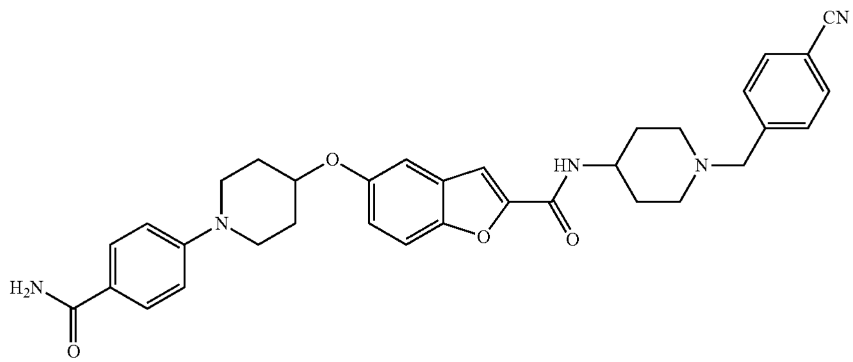 [SMILES: N#Cc1ccc(CN2CCC(NC(=O)c3cc4cc(OC5CCN(c6ccc(C(N)=O)cc6)CC5)ccc4o3)CC2)cc1] |
| 137 | N-(1-(pyridin-4-ylmethyl)piperidin-4-yl)-5-(1-(4-(trifluoromethoxy)phenyl)piperidin-4-yloxy)benzo[b]thiophene-2-carboxamide | 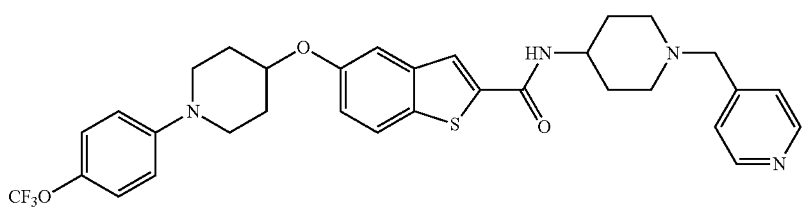 |
| 138 | N-(1-(pyridin-4-ylmethyl)piperidin-4-yl)-5-(1-(4-(trifluoromethyl)phenyl)piperidin-4-yloxy)benzo[b]thiophene-2-carboxamide | 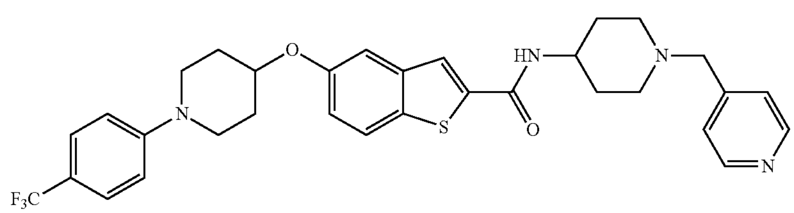 [SMILES: O=C(NC1CCN(Cc2ccncc2)CC1)c1cc2cc(OC3CCN(c4ccc(C(F)(F)F)cc4)CC3)ccc2s1] |
| 139 | N-(1-(pyridin-4-ylmethyl)piperidin-4-yl)-5-(1-(4-chlorophenyl)piperidin-4-yloxy)benzo[b]thiophene-2-carboxamide | 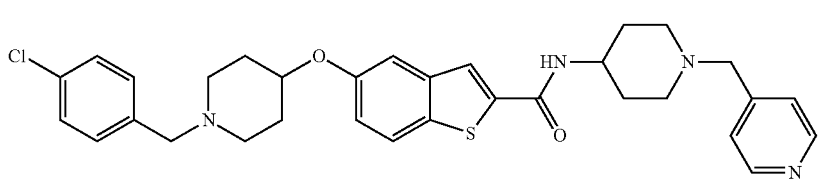 [SMILES: O=C(NC1CCN(Cc2ccncc2)CC1)c1cc2cc(OC3CCN(Cc4ccc(Cl)cc4)CC3)ccc2s1] |
| 140 | tert-butyl 4-(6-(1-(4-(trifluoromethyl)phenyl)piperidin-4-yloxy)benzo[b]thiophene-2-carboxamido)piperidine-1-carboxylate | 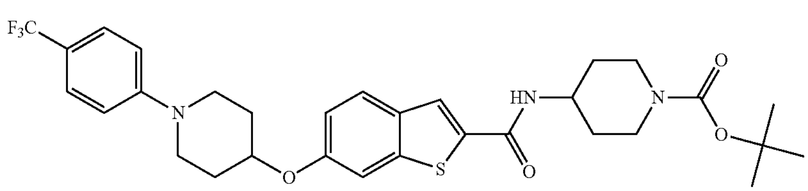 [SMILES: CC(C)(C)OC(=O)N1CCC(NC(=O)c2cc3ccc(OC4CCN(c5ccc(C(F)(F)F)cc5)CC4)cc3s2)CC1] |

TABLE 1-continued

| No. | Name | Structure |
|---|---|---|
| 141 | N-(piperidin-4-yl)-6-(1-(4-(trifluoromethyl)phenyl)piperidin-4-yloxy)benzo[b]thiophene-2-carboxamide | 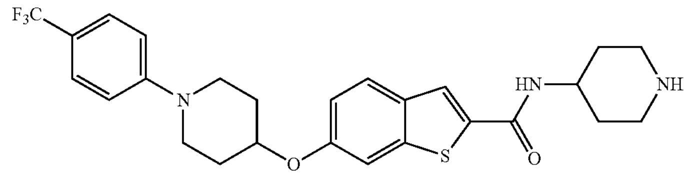 [SMILES: O=C(NC1CCNCC1)c1cc2ccc(OC3CCN(c4ccc(C(F)(F)F)cc4)CC3)cc2s1] |
| 142 | N-(1-(pyridin-4-ylmethyl)piperidin-4-yl)-6-(1-(4-(trifluoromethyl)phenyl)piperidin-4-yloxy)benzo[b]thiophene-2-carboxamide | 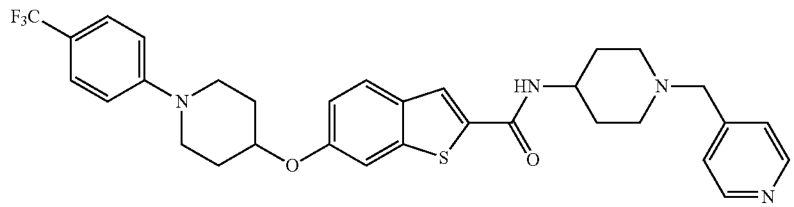 [SMILES: O=C(NC1CCN(Cc2ccncc2)CC1)c1cc2ccc(OC3CCN(c4ccc(C(F)(F)F)cc4)CC3)cc2s1] |
| 143 | N-(1-(pyridin-2-ylmethyl)piperidin-4-yl)-6-(1-(4-(trifluoromethyl)phenyl)piperidin-4-yloxy)benzo[b]thiophene-2-carboxamide | 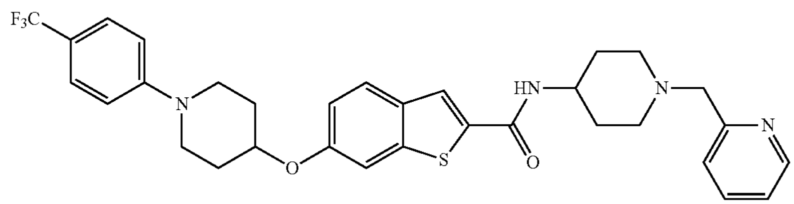 |
| 144 | N-(1-(4-cyanobenzyl)piperidin-4-yl)-6-(1-(4-(trifluoromethyl)phenyl)piperidin-4-yloxy)benzo[b]thiophene-2-carboxamide | 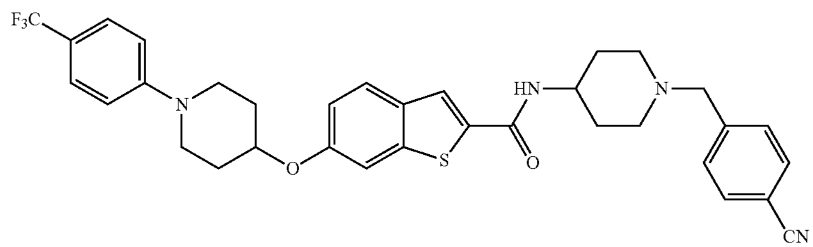 |
| 145 | N-(1-(3-cyanobenzyl)piperidin-4-yl)-6-(1-(4-(trifluoromethyl)phenyl)piperidin-4-yloxy)benzo[b]thiophene-2-carboxamide | 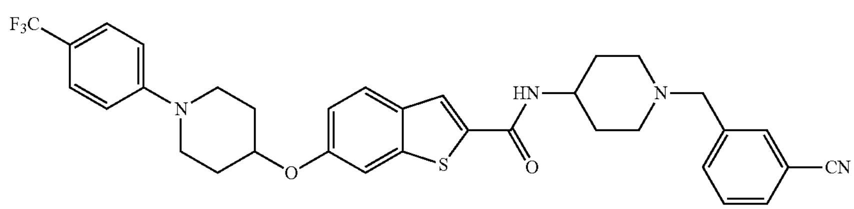 [SMILES: N#Cc1cccc(CN2CCC(NC(=O)c3cc4ccc(OC5CCN(c6ccc(C(F)(F)F)cc6)CC5)cc4s3)CC2)c1] |
| 146 | N-(1-(2-cyanobenzyl)piperidin-4-yl)-6-(1-(4-(trifluoromethyl)phenyl)piperidin-4-yloxy)benzo[b]thiophene-2-carboxamide | 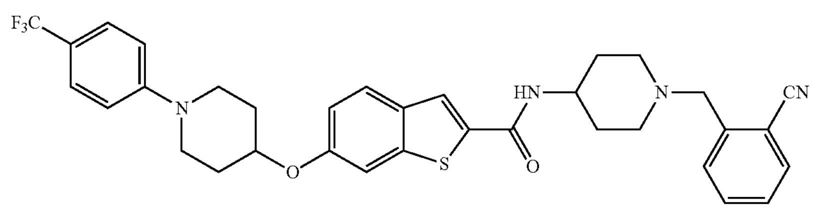 [SMILES: N#Cc1ccccc1CN1CCC(NC(=O)c2cc3ccc(OC4CCN(c5ccc(C(F)(F)F)cc5)CC4)cc3s2)CC1] |
| 147 | tert-butyl 4-(3-chloro-6-(1-(4-(trifluoromethyl)phenyl)piperidin-4-yloxy)benzo[b]thiophene-2-carboxamido)piperidine-1-carboxylate | 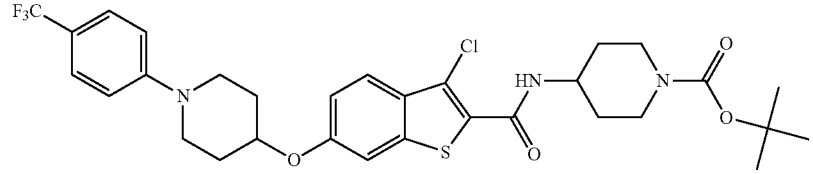 [SMILES: CC(C)(C)OC(=O)N1CCC(NC(=O)c2sc3cc(OC4CCN(c5ccc(C(F)(F)F)cc5)CC4)ccc3c2Cl)CC1] |

TABLE 1-continued

| No. | Name | Structure |
|---|---|---|
| 148 | 3-chloro-N-(piperidin-4-yl)-6-(1-(4-(trifluoromethyl)phenyl)piperidin-4-yloxy)benzo[b]thiophene-2-carboxamide | 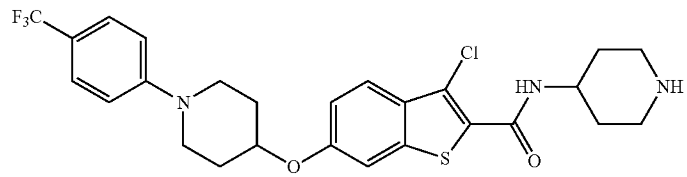 [SMILES: O=C(NC1CCNCC1)c1sc2cc(OC3CCN(c4ccc(C(F)(F)F)cc4)CC3)ccc2c1Cl] |
| 149 | tert-butyl 4-(5-(1-(4-(trifluoromethyl)phenyl)piperidin-4-yloxy)benzo[b]thiophene-2-carboxamido)piperidine-1-carboxylate | 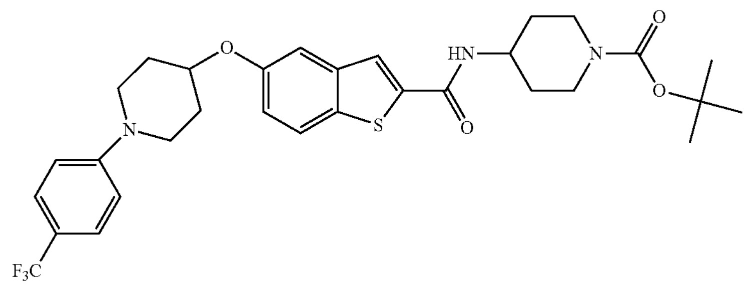 [SMILES: CC(C)(C)OC(=O)N1CCC(NC(=O)c2cc3cc(OC4CCN(c5ccc(C(F)(F)F)cc5)CC4)ccc3s2)CC1] |
| 150 | N-(piperidin-4-yl)-5-(1-(4-(trifluoromethyl)phenyl)piperidin-4-yloxy)benzo[b]thiophene-2-carboxamide | 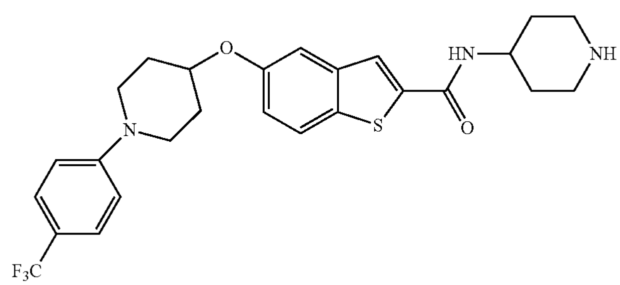 [SMILES: O=C(NC1CCNCC1)c1cc2cc(OC3CCN(c4ccc(C(F)(F)F)cc4)CC3)ccc2s1] |
| 151 | 3-chloro-N-(1-(pyridin-4-ylmethyl)piperidin-4-yl)-6-(1-(4-(trifluoromethyl)phenyl)piperidin-4-yloxy)benzo[b]thiophene-2-carboxamide | 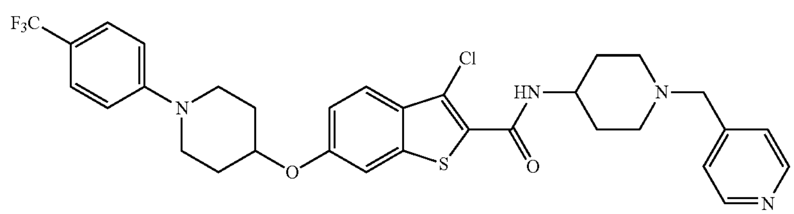 [SMILES: O=C(NC1CCN(Cc2ccncc2)CC1)c1sc2cc(OC3CCN(c4ccc(C(F)(F)F)cc4)CC3)ccc2c1Cl] |
| 152 | 3-chloro-N-(1-(pyridin-3-ylmethyl)piperidin-4-yl)-6-(1-(4-(trifluoromethyl)phenyl)piperidin-4-yloxy)benzo[b]thiophene-2-carboxamide | 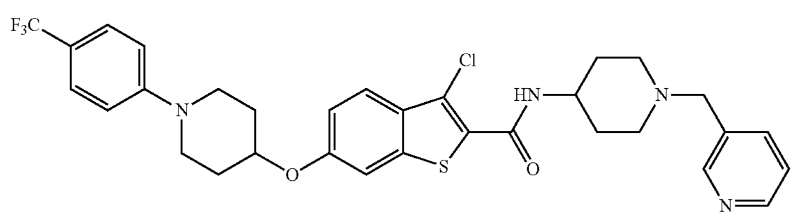 [SMILES: O=C(NC1CCN(Cc2cccnc2)CC1)c1sc2cc(OC3CCN(c4ccc(C(F)(F)F)cc4)CC3)ccc2c1Cl] |
| 153 | 3-chloro-N-(1-(pyridin-2-ylmethyl)piperidin-4-yl)-6-(1-(4-(trifluoromethyl)phenyl)piperidin-4-yloxy)benzo[b]thiophene-2-carboxamide | 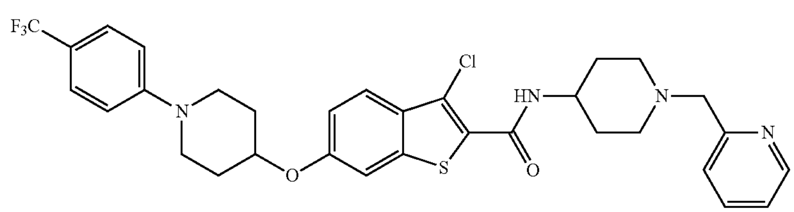 |

TABLE 1-continued

| No. | Name | Structure |
|---|---|---|
| 154 | 3-chloro-N-(1-(4-cyanobenzyl)piperidin-4-yl)-6-(1-(4-(trifluoromethyl)phenyl)piperidin-4-yloxy)benzo[b]thiophene-2-carboxamide | 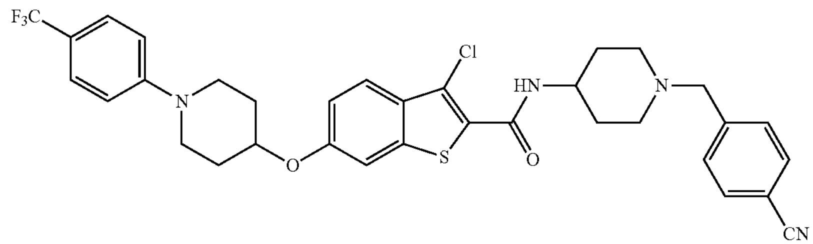 [SMILES: N#Cc1ccc(CN2CCC(NC(=O)c3sc4cc(OC5CCN(c6ccc(C(F)(F)F)cc6)CC5)ccc4c3Cl)CC2)cc1] |
| 155 | 3-chloro-N-(1-isonicotinoylpiperidin-4-yl)-6-(1-(4-(trifluoromethyl)phenyl)piperidin-4-yloxy)benzo[b]thiophene-2-carboxamide | 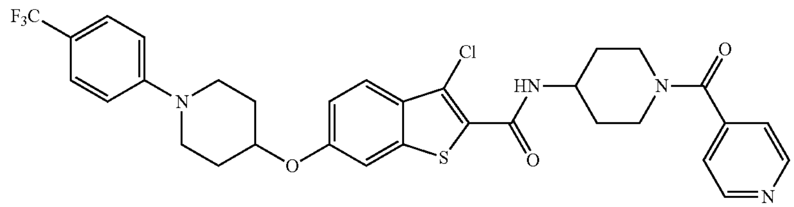 [SMILES: O=C(NC1CCN(C(=O)c2ccncc2)CC1)c1sc2cc(OC3CCN(c4ccc(C(F)(F)F)cc4)CC3)ccc2c1Cl] |
| 156 | tert-butyl 4-(5-(1-(4-(trifluoromethyl)phenyl)piperidin-4-yloxy)-2,3-dihydro-1H-inden-1-ylamino)piperidine-1-carboxylate | 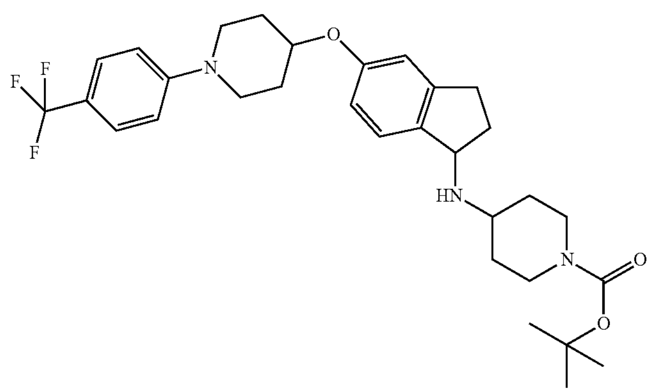 [SMILES: CC(C)(C)OC(=O)N1CCC(NC2CCc3cc(OC4CCN(c5ccc(C(F)(F)F)cc5)CC4)ccc32)CC1] |
| 157 | N-(5-(1-(4-(trifluoromethyl)phenyl)piperidin-4-yloxy)-2,3-dihydro-1H-inden-1-yl)piperidin-4-amine | 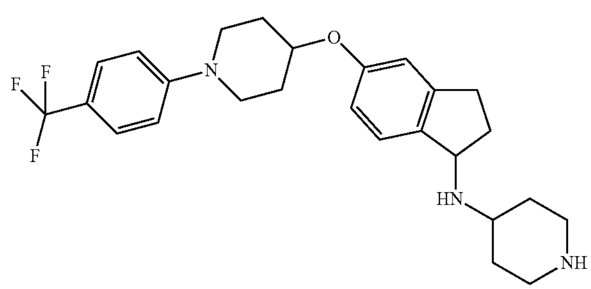 [SMILES: FC(F)(F)c1ccc(N2CCC(Oc3ccc4c(c3)CCC4NC3CCNCC3)CC2)cc1] |
| 158 | 1-(pyridin-4-ylmethyl)-N-(5-(1-(4-(trifluoromethyl)phenyl)piperidin-4-yloxy)-2,3-dihydro-1H-inden-1-yl)piperidin-4-amine | 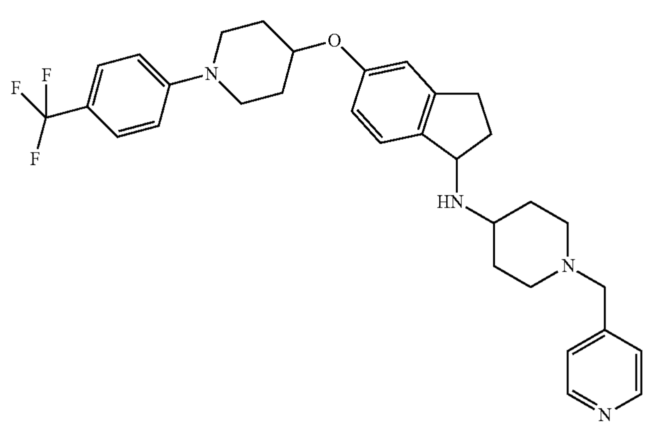 [SMILES: FC(F)(F)c1ccc(N2CCC(Oc3ccc4c(c3)CCC4NC3CCN(Cc4ccncc4)CC3)CC2)cc1] |

TABLE 1-continued

| No. | Name | Structure |
|---|---|---|
| 159 | 1-(4-fluorobenzyl)-N-(5-(1-(4-(trifluoromethyl)phenyl)piperidin-4-yloxy)-2,3-dihydro-1H-inden-1-yl)piperidin-4-amine | 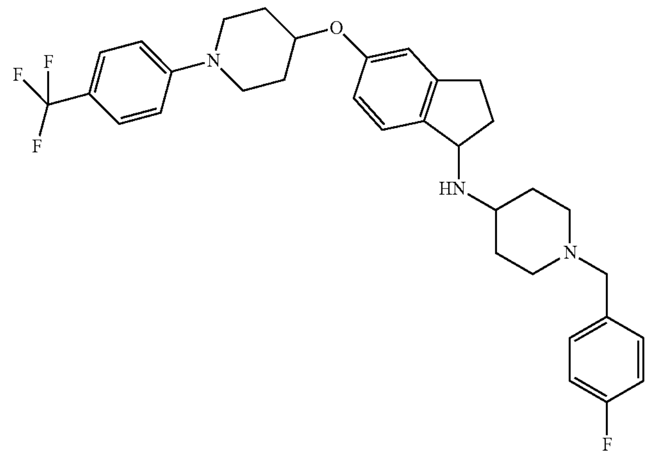 [SMILES: Fc1ccc(CN2CCC(NC3CCc4cc(OC5CCN(c6ccc(C(F)(F)F)cc6)CC5)ccc43)CC2)cc1] |
| 160 | 4-((4-(5-(1-(4-(trifluoromethyl)phenyl)piperidin-4-yloxy)-2,3-dihydro-1H-inden-1-ylamino)piperidin-1-yl)methyl)benzonitrile | 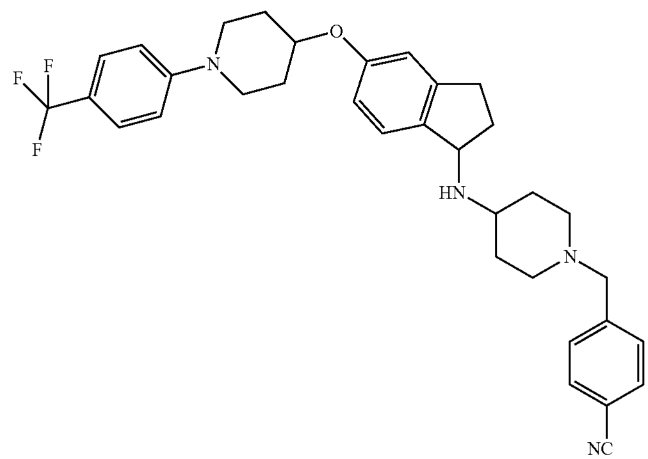 [SMILES: N#Cc1ccc(CN2CCC(NC3CCc4cc(OC5CCN(c6ccc(C(F)(F)F)cc6)CC5)ccc43)CC2)cc1] |

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. CH$_3$—CH$_2$—), in some circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as (A)$_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, desirably from 1 to about 12 carbons (i.e., inclusive of 1 and 12). The term "C$_m$-C$_n$ alkyl" means an alkyl group having from m to n carbon atoms (i.e., inclusive of m and n). The term "C$_m$-C$_n$ alkyl" means an alkyl group having from m to n carbon atoms. For example, "C$_1$-C$_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "C$_o$ alkyl"), the group is simply a single covalent bond if it is a divalent radical or is a hydrogen atom if it is a monovalent radical. For example, the moiety "—(C$_0$-C$_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic carbocyclic ring system having a single ring (e.g., phenyl) which is optionally fused to other aromatic hydrocarbon rings or non-aromatic hydrocarbon rings. "Aryl" includes ring systems having multiple condensed rings and in which at least one is aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, 2,3-dihydrobenzofuranyl and 6,7,8,9-tetrahydro-5H-benzo[a]cycloheptenyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). The heterocycloalkyl ring is optionally with fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2 (1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Preferred cycloalkyl groups have from 3 to 7 members in a single ring. More preferred cycloalkyl groups have 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O) O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —$OSO_2OR^{71}$, —$P(O)(O^-)_2(M^+)_2$, —$P(O)(OR^{71})O^-M^+$, —$P(O)(OR^{71})_2$, —$C(O)R^{71}$, —$C(S)R^{71}$, —$C(NR^{71})R^{71}$, —$C(O)O^-M^+$, —$C(O)OR^{71}$, —$C(S)OR^{71}$, —$C(O)NR^{81}R^{81}$, —$C(NR^{71})NR^{81}R^{81}$, —$OC(O)R^{71}$, —$OC(S)R^{71}$, —$OC(O)O^-M^+$, —$OC(O)OR^{71}$, —$OC(S)OR^{71}$, —$NR^{71}C(O)R^{71}$, —$NR^{71}C(S)R^{71}$, —$NR^{71}CO_2^-M^+$, —$NR^{71}CO_2R^{71}$, —$NR^{71}C(S)OR^{71}$, —$NR^{71}C(O)NR^{81}R^{81}$, —$NR^{71}C(NR^{71})R^{71}$ and —$NR^{71}C(NR^{71})NR^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{72}$, —$SR^{72}$, —$S^-M^+$, =S, —$NR^{82}R^{82}$, =$NR^{72}$, =N—$OR^{72}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{72}$, —$OSO_2R^{72}$, —$OSO_2O^-M^+$, —$OSO_2OR^{72}$, —$P(O)(O^-)_2(M^+)_2$, —$P(O)(OR^{72})O^-M^+$, —$P(O)(OR^{72})_2$, —$C(O)R^{72}$, —$C(S)R^{72}$, —$C(NR^{72})R^{72}$, —$C(O)O^-M^+$, —$C(O)OR^{72}$, —$C(S)OR^{72}$, —$C(O)NR^{82}R^{82}$, —$C(NR^{72})NR^{82}R^{82}$, —$OC(O)R^{72}$, —$OC(S)R^{72}$, —$OC(O)O^-M^+$, —$OC(O)OR^{72}$, —$OC(S)OR^{72}$, —$NR^{72}C(O)R^{72}$, —$NR^{72}C(S)R^{72}$, —$NR^{72}CO_2^-M^+$, —$NR^{72}CO_2R^{72}$, —$NR^{72}C(S)OR^{72}$, —$NR^{72}C(O)NR^{82}R^{82}$, —$NR^{72}C(NR^{72})R^{72}$ and —$NR^{72}C(NR^{72})NR^{82}R^{82}$; and each $R^{81}$ is independently $R^{71}$ or alternatively, two $R^{81}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$ alkyl) or ($C_1$-$C_6$ fluoroalkyl); each $R^{82}$ is independently $R^{72}$ or alternatively, two $R^{82s}$, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —$NR^{80}R^{80}$ is meant to include —$NH_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups for hydrogens on nitrogen atoms in "substituted" heteroalkyl and heterocycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

The compounds disclosed herein can also be provided as solvates, hydrates or N-oxides.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound) can be chosen as hits and further screened using the below-described functional assays to identify adiponectin receptor agonists.

An in-cell western assay can be performed to demonstrate the activation of AMPK in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds of structural formulae (I)-(XCIV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(XCIV).

In the pharmaceutical compositions disclosed herein, one or more compounds of structural formulae (I)-(XCIV) may be present in association with one or more pharmaceutically acceptable carriers, diluents or excipients, and, if desired, other active ingredients. The pharmaceutical compositions containing compounds of structural formulae (I)-(XCIV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(XCIV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(XCIV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described herein. For example, compounds of structural formulae (II)-(VI) can be prepared according to Scheme 1, below, or analogous synthetic schemes:

Scheme 1

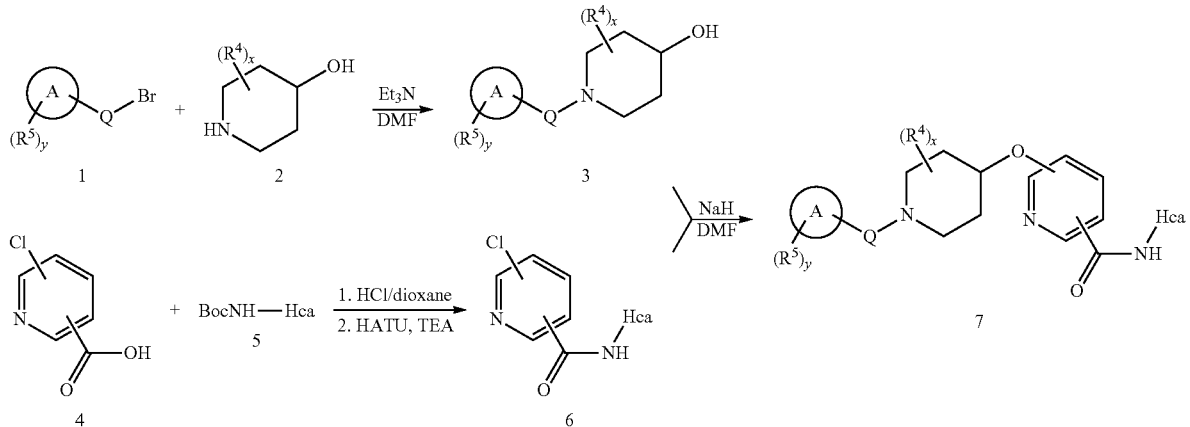

Referring to Scheme 1, bromide 1, for example, is coupled with 4-hydroxypiperidine 2 to provide 1-substituted 4-hydroxypiperidine 3. In a separate reaction, protected Hca-amine 5 is deprotected and coupled with chloropiperidinecarboxylic acid 4 to provide chloropyridineamide 6, which is then coupled with 3 under Mitsonobu conditions to yield 4-(piperidin-4-yloxy)pyridineamide 7.

One of ordinary skill in the art can adapt the reaction sequence of Scheme 1 to fit the desired target molecule. For example, a benzyl bromide can be used as a starting material to afford compounds in which the "A" ring system is a phenyl and Q is methylene. Similarly, a (heteroaryl)methyl bromide may be used as a starting material to afford compounds in which the "A" ring system is a heteroaryl. Alternatively, reductive amination of an aryl or heteroaryl aldehyde, for example, with the nitrogen of azacycloalkyl 2 would also afford 3. In certain situations one of ordinary skill in the art will use different reagents to effect one or more of the individual steps or to use protected versions of certain of the $R^1$, $R^2$, $R^3$, $R^4$ and $R^5$ substituents. An example of the synthesis of a compound according to Scheme 1 is provided below in Example 1.

Compounds of structural formulae (VIII)-(XIII) can be prepared according to Scheme 2, below, or analogous synthetic schemes:

Scheme 3

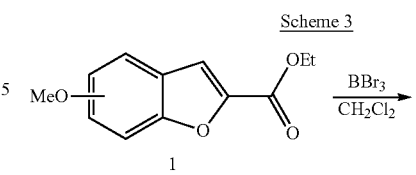

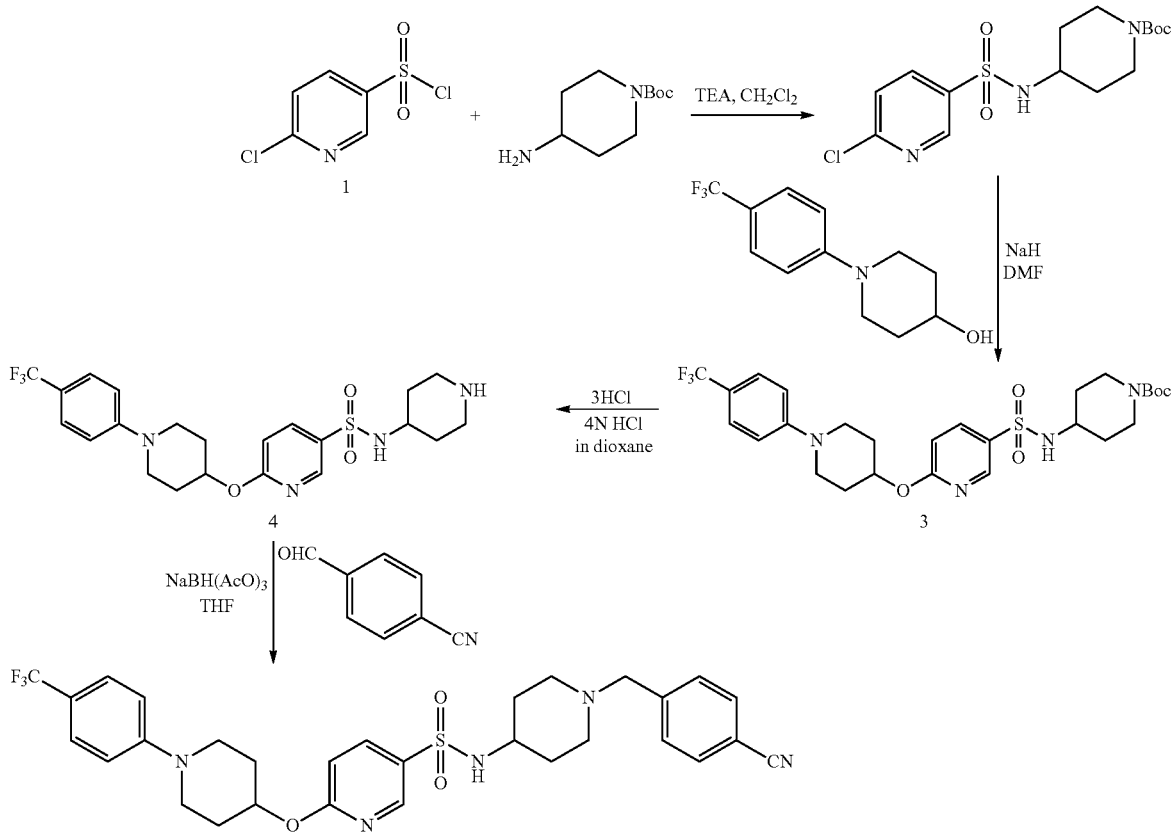

Referring to Scheme 2, chloropyridinesulfonyl chloride 1, for example, is coupled with BOC-protected 4-aminopiperidine to provide sulfonamide 2. Sulfonamide 3 is coupled with a piperidinol to form protected N-piperidinyl sulfonamide 3, which is deprotected to yield N-piperidinyl sulfonamide 4. Finally, a benzaldehyde is reductively coupled to N-piperidinyl sulfonamide 4 to provide the final product. Of course, in certain situations one of ordinary skill in the art will use different reagents to affect one or more of the individual steps or to use protected versions of certain of the substituents. As well, one of ordinary skill in the art would appreciate that other synthetic routes or sequence of steps can be used to make the presently disclosed compounds. An example of the synthesis of a compound according to Scheme 2 is provided below in Example 2.

Compounds of structural formulae (XIV)-(XV) can be prepared according to Scheme 3, below, or analogous synthetic schemes:

-continued

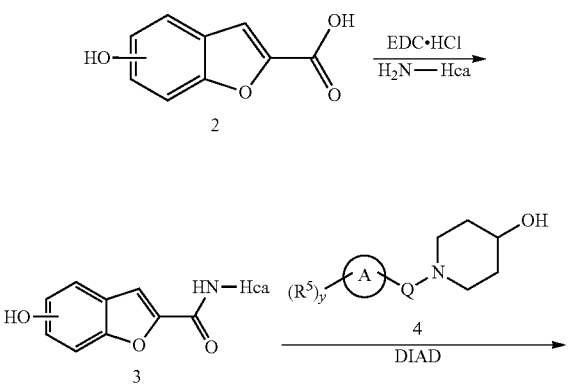

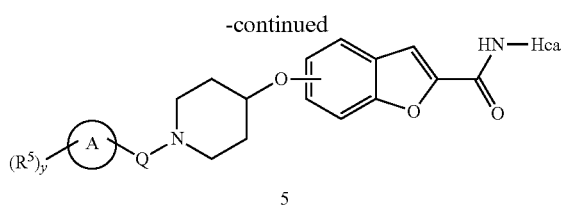

Referring to Scheme 3, methoxybenzofuran ester 1, for example, is converted to the corresponding hydroxybenzofuran carboxylic acid 2 with boron tribromide. Carboxylic acid 2 is coupled with Hca amine to yield hydroxybenzofuranamide 3. 1-Substituted 4-hydroxypiperidine 4 is coupled with amide 3 to yield (piperidin-4-yloxy)benzofuranamide 5.

One of skill in the art can adapt the reaction sequence of Scheme 3 to fit the desired target molecule. Of course, in certain situations one of skill in the art will use different reagents to affect one or more of the individual steps or to use protected versions of certain of the substituents. An example of the synthesis of a compound according to Scheme 3 is provided below in Example 3.

Compounds of structural formulae (XVI)-(XVII) can be prepared according to Scheme 4, below, or analogous synthetic schemes:

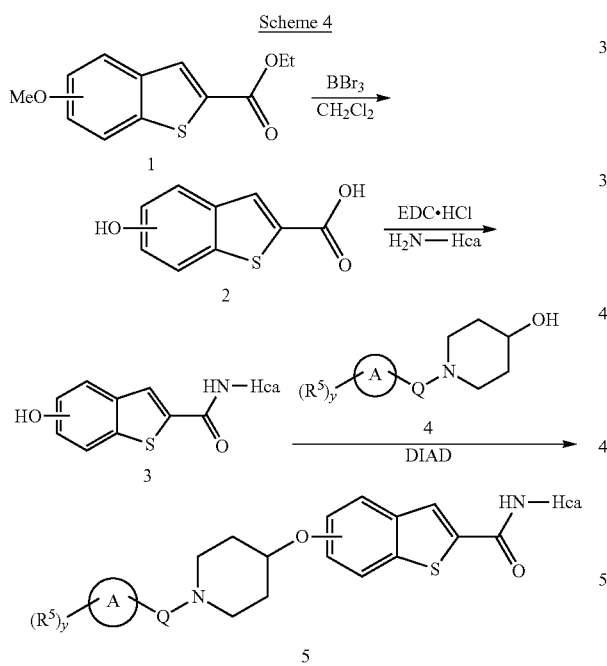

Referring to Scheme 4, methoxybenzothiophene ester 1, for example, is converted to the corresponding hydroxybenzothiophene carboxylic acid 2 with boron tribromide. Carboxylic acid 2 is coupled with Hca amine to yield hydroxybenzothiophene amide 3. 1-Substituted 4-hydroxypiperidine 4 is coupled with amide 3 to yield (piperidin-4-yloxy)benzothiopheneamide 5.

One of skill in the art can adapt the reaction sequence of Scheme 4 to fit the desired target molecule. Of course, in certain situations one of skill in the art will use different reagents to affect one or more of the individual steps or to use protected versions of certain of the substituents.

Compounds of structural formulae (XVIII)-(XIX) can be prepared according to Scheme 5, below, or analogous synthetic schemes:

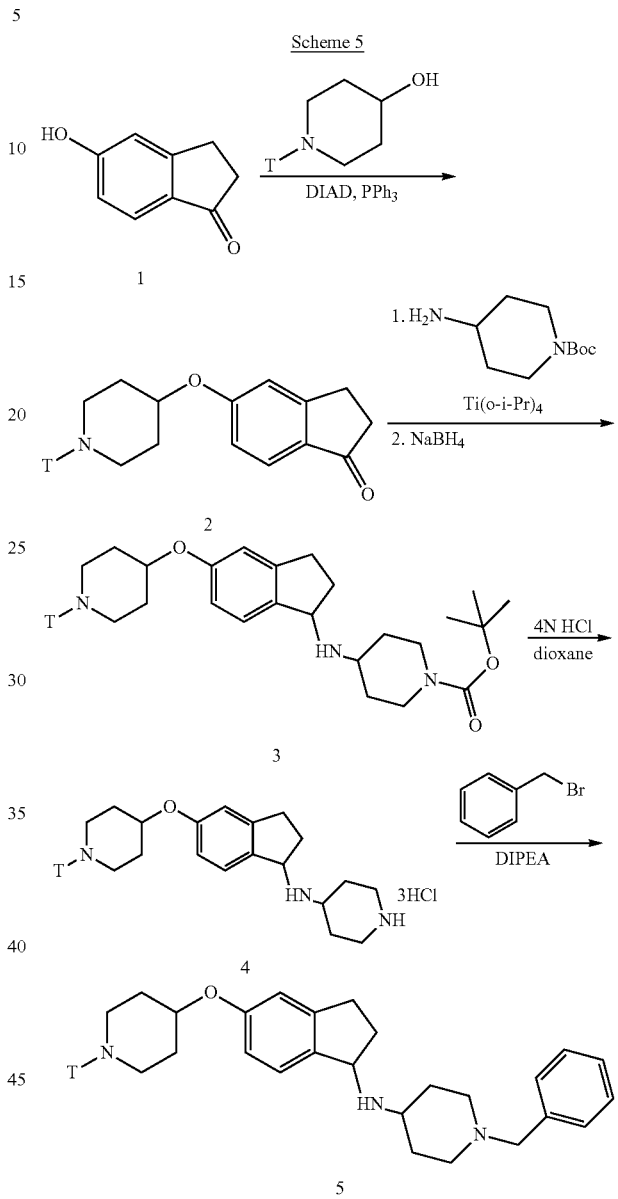

Referring to Scheme 5, hydroxydihydroindenone 1, for example, is coupled with a 1-substituted 4-hydroxypiperidine to provide (piperidin-4-yloxy)dihydroindenone 2. One of ordinary skill in the art would appreciate that the 5-hydroxy group of 1 could be at other positions on the aromatic ring, e.g. at the 6-position, to make other regiosiomeric compounds, e.g. regioisomeric versions of compound 5 where the ether linkage is at the 6-position instead of the 5-position. Hca-amine (shown here as a BOC-protected 4-piperidineamine) is reductively coupled to (piperidin-4-yloxy)dihydroindenone 2 to yield (piperidin-4-yloxy)dihydroindeneamine 3. Further manipulations can be performed to provide desired substitutions. For example, in Scheme 5, BOC-protected (piperidin-4-yloxy)dihydroindeneamine 3 is deprotected, then coupled with a benzyl bromide to provide compound 5. Of course, in certain situations one of ordinary skill in the art will use different reagents to affect one or more of the individual steps or to use protected versions of certain of the substituents. An example of the synthesis of a compound according to Scheme 5 is provided below in Example 5.

Compounds suitable for use in the presently disclosed pharmaceutical compositions include compounds of Table 1, above. These compounds can be made according to the general schemes described above, for example using a procedure similar to that described below in the Examples.

While not intending to be bound by theory, the inventors surmise that compounds of structural formulae (I)-(XCIV) are mimics of adiponectin which act as adiponectin receptor agonists, thereby activating the AMPK pathway. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(XCIV) should also inhibit the inflammatory processes which occur during the early phases of atherosclerosis. Accordingly, compounds of structural formulae (I)-(XCIV) can be useful in the treatment of type II diabetes and in the treatment and prevention of atherosclerosis, cardiovascular disease, obesity and non-alcoholic fatty liver disease.

Accordingly, another aspect of the present disclosure relates to a method of activating the AMPK pathway. According to this aspect, a method for activating the AMPK pathway in a cell includes contacting the cell with an effective amount of a compound, pharmaceutically acceptable salt, prodrug, solvate, hydrate, N-oxide or composition described above.

In one embodiment, a method of increasing fatty acid oxidation in a cell includes contacting the cell with an effective amount of a compound, pharmaceutically acceptable salt, prodrug, solvate, hydrate, N-oxide or composition described above. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because the presently disclosed compounds can increase the rate of phosphorylation of ACC, they can reduce the inhibition of fatty acid oxidation and therefore increase its overall rate.

In another embodiment, a method of decreasing glycogen concentration in a cell includes contacting the cell with an effective amount of a compound, pharmaceutically acceptable salt, prodrug, solvate, hydrate, N-oxide or composition described above.

In another embodiment, a method of increasing glucose uptake in a cell includes contacting the cell with an effective amount of a compound, pharmaceutically acceptable salt, prodrug, solvate, hydrate, N-oxide or composition described above.

In another embodiment, a method of reducing triglyceride levels in a subject includes administering to the subject an effective amount of a compound, pharmaceutically acceptable salt, prodrug, solvate, hydrate, N-oxide or composition described above.

In another embodiment, a method of increasing insulin sensitivity of a subject includes administering to the subject an effective amount of a compound, pharmaceutically acceptable salt, prodrug, solvate, hydrate, N-oxide or composition described above.

Accordingly, the compounds and compositions disclosed herein can be used to treat a variety of metabolic disorders. For example, in one embodiment, a method of treating type II diabetes in a subject in need of such treatment includes administering to the subject an effective amount of a compound, pharmaceutically acceptable salt, prodrug, solvate, hydrate, N-oxide or composition described above. In another embodiment, a method of treating or preventing atherosclerosis or cardiovascular disease in a subject includes administering to the subject an effective amount of a compound, pharmaceutically acceptable salt, prodrug, solvate, hydrate, N-oxide or composition described above.

As described above, the compounds disclosed herein can act as activators of the AMPK pathway. Accordingly, in another embodiment, a method comprises modulating the AMPK pathway (either in vitro or in vivo) by contacting a cell with a compound, pharmaceutically acceptable salt, prodrug, solvate, hydrate, N-oxide or composition described above, or administering a compound, pharmaceutically acceptable salt, prodrug, solvate, hydrate, N-oxide or composition described above to a mammal (e.g., a human) in an amount sufficient to modulate the AMPK activity and study the effects thereby induced. Such methods are useful for studying the AMPK pathway and its role in biological mechanisms and disease states both in vitro and in vivo.

Another embodiment is the use of a compound, pharmaceutically acceptable salt, prodrug, solvate, hydrate or N-oxide or composition as described above in the manufacture of a medicament for any of the therapeutic purposes described above. For example, the medicament can be for the reduction of triglyceride levels in a subject, the treatment of type II diabetes in a subject, or the treatment or prevention of atherosclerosis or cardiovasclular disease in a subject.

The compounds disclosed herein can be linked to labeling agents, for example for use in variety of experiments exploring their receptor binding, efficacy and metabolism. Accordingly, another embodiment is a labeled conjugate comprising a compound as disclosed herein covalently linked to a labeling agent, optionally through a linker. Suitable linker and labeling agents will be readily apparent to those of skill in the art upon consideration of the present disclosure. The labeling agent can be, for example, an affinity label such as biotin or strepavidin, a hapten such as digoxigenin, an enzyme such as a peroxidase, or a fluorophoric or chromophoric tag. Any suitable linker can be used. For example, in some embodiments, an ethylene glycol, oligo(ethylene glycol) or poly (ethylene glycol) linker is used. Other examples of linkers include amino acids, which can be used alone or in combination with other linker groups, such as ethylene glycol, oligoethylene glycol or polyethylene glycol. Suitable linkers include, without limitation, single amino acids, as well as di- and tripeptides. In one embodiment, the linker includes a glycine residue. The person of skill in the art will realize, of course, that other linkers and labeling agents can be used. In other embodiments, an alkylene chain is the linker. In other embodiments, the linker has the structure —[($C_0$-$C_3$ alkyl)-$Y^m$—]$_m$—, in which each $Y^m$ is —O—, —N($R^9$)—, or L, and m is in the range of 1-40. For example, in certain embodiments, a labeled conjugate has structural formula (XCV):

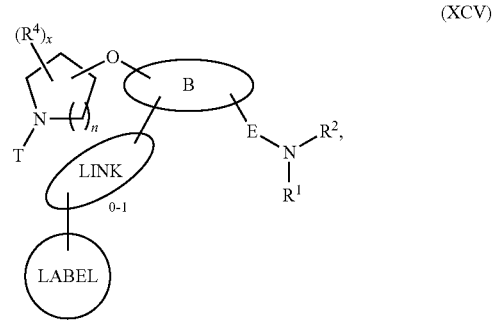

(XCV)

in which the "LINK" moiety is a linker and is optional, and the "LABEL" moiety is a labeling agent, and all other variables are as described above, for example with respect to structural formula (I). Any of the compounds disclosed with respect to structural formulae (I)-(XCIV) can be used in the labeled conjugate of structural formula (XCV).

In certain embodiments, the -(LINK)$_{0-1}$-(LABEL) moiety is attached the "B" ring system at a benzo or pyrido ring position meta to the alicyclic ethereal oxygen. For example, in one embodiment, a labeled conjugate has structural formula (XCVI):

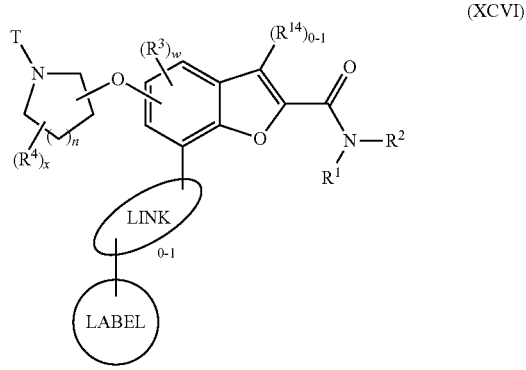

(XCVI)

in which the "LINK" moiety is a linker and is optional, and the "LABEL" moiety is a labeling agent, and all other variables are as described above, for example with respect to structural formulae (XIV), (XV), (XXXII), (XXXIII), (XXX-VIII)-(XLVII), (LX), (LXI), (LXVI)-(LXXIV) and (LXXXIII)-(LXXXVI).

For example, in one particular embodiment, a labeled conjugate has structural formula (XCVII):

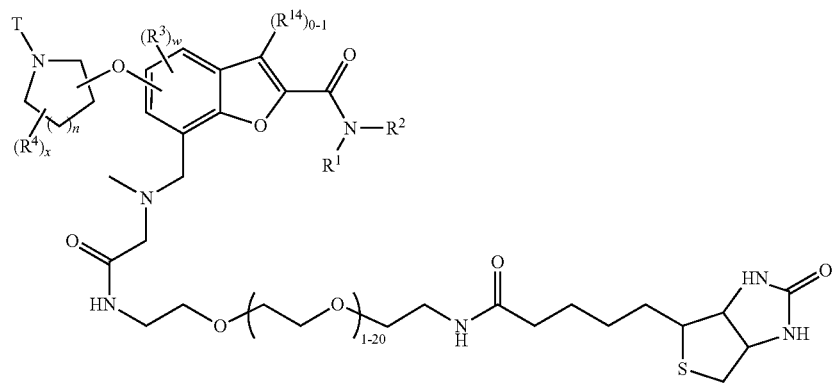

(XCVII)

in which all variables are as described above, for example with respect to structural formulae (XIV), (XV), (XXXII), (XXXIII), (XXXVIII)-(XLVII), (LX), (LXI), (LXVI)-(LXXIV) and (LXXXIII)-(LXXXVI).

The following examples are intended to further illustrate certain embodiments and are not intended to limit the scope of the invention.

EXAMPLES

Example 1

(a) Synthetic Example

N-(1-(Pyridin-4-ylmethyl)piperidin-4-yl)-6-(1-(4-(trifluoromethyl)phenyl)-piperidin-4-yloxy)picolinamide (compound 43)

Step 1

A solution of t-butyl 1-(pyridin-4-ylmethyl)piperidin-4-ylcarbamate (1.80 g, 6.2 mmol) in 4M HCl/dioxane (15 mL) was allowed to stir at room temperature for 2 h. The resulting reaction mixture was then concentrated to provide a white crystalline solid, which was triturated with ether, filtered and dried. MS (m/z): 192 (M+H)$^+$.

Step 2

The HCl salt (obtained from step 1 above) was dissolved in DMF (15 mL) and transferred to a flask containing a solution of 6-chloropicolinic acid (1.0 g, 6.3 mmol), and HATU (2.9 g, 7.6 mmol) in DMF (10 mL). N-Methylmorpholine (1.5 mL, 1.38 g, 13.6 mmol) was then added and the resulting reaction mixture was allowed to stir at room temperature under N$_2$ atmosphere overnight. The heterogeneous reaction mixture was then poured into saturated sodium bicarbonate solution (100 mL) and extracted with ethyl acetate (3×50 mL). The combined organic layers were then washed with water (2×50 mL), brine (1×50 mL), dried (MgSO$_4$), filtered and concentrated to give a brown residue, which upon trituration with ethyl ether provided 6-chloro-N-(1-(pyridin-4-ylmethyl)piperidin-4-yl)picolinamide as a yellow crystalline solid (1.31 g, 64%). $^1$H NMR (CDCl$_3$) δ 8.93-8.82 (m, 2H), 8.12-8.06 (m, 1H), 7.96-7.74 (m, 5H), 7.51-7.47 (m, 1H), 4.34 (br s, 2H), 4.26 (br s, 1H), 3.63-3.47 (m, 2H), 3.16-2.92 (m, 2H), 2.60-2.40 (m, 2H), 2.36-2.14 (m, 2H). MS (m/z): 331 (M+H)$^+$ confirmed by LC-MS, t$_r$=3.67 min Step 3

To a solution of 1-(4-(trifluoromethyl)phenyl)-piperidin-4-ol (0.1 g, 0.4 mmol) in anhydrous DMF, NaH (60% in mineral oil, 18 mg, 0.45 mmol) was added. The mixture was allowed to stir at room temperature under N$_2$ atmosphere for 10 min, followed by the addition of 6-chloro-N-(1-(pyridin-4-ylmethyl)piperidin-4-yl)picolinamide (0.15 g, 0.4 mmol). The resulting reaction mixture was then stirred with heating at 105° C. overnight. A significant amount of starting material was still present and hence, an additional amount of NaH was added (82 mg, 2.1 mmol). The reaction mixture was allowed to stir at 105° C. for an additional 8 h, and quenched with saturated sodium bicarbonate solution (20 mL). The aqueous layer was extracted with ethyl acetate (3×20 mL), and the combined organic layer was washed with water (2×20 mL) and brine (1×20 mL), dried (MgSO$_4$), filtered and concentrated to give a yellow residue. Column chromatography (100% CH$_2$Cl$_2$ 3% MeOH/CH$_2$Cl$_2$) provided a yellow solid, which upon trituration with ethyl ether, yielded N-(1-(pyridin-4-ylmethyl)piperidin-4-yl)-6-(1-(4-(trifluoromethyl) phenyl)piperidin-4-yloxy)picolinamide as a tan solid (54 mg, 25%). $^1$H NMR (CD$_3$OD) δ 8.53 (d, J=4.1 Hz, 2H), 8.28 (d, J=7.4 Hz, 1H), 7.80 (t, J=7.7 Hz, 1H), 7.65 (d, J=7.2 Hz, 1H), 7.51 (d, J=4.1 Hz, 2H), 7.46 (d, J=8.5 Hz, 2H), 7.05 (d, J=8.3 Hz, 2H), 6.96 (d, J=8.3 Hz, 1H), 5.43 (br s, 1H), 4.10-3.95 (m, 1H), 3.90 (s, 2H), 3.77-3.56 (m, 2H), 3.23-2.98 (m, 3H), 2.71-2.57 (m, 2H), 2.23-1.81 (m, 9H). MS (m/z): 540 (M+H)$^+$.

(b) Analytical Data

The following compounds were prepared using methods analogous to those described in Example 1(a) and in Scheme 1.

Compound 1: $^1$H NMR (CDCl$_3$, 300 MHz) δ 8.54 (m, 2H), 8.20 (m, 1H), 8.14 (m, 1H), 7.77 (m, 1H), 7.50 (m, 2H), 7.29 (m, 3H), 6.89 (m, 2H), 4.65 (m, 1H), 3.99 (m, 1H), 3.63 (m, 2H), 3.52 (s, 2H), 3.35 (m, 2H), 2.83 (m, 2H), 2.23 (m, 2H), 2.03 (m, 6H), 1.66 (m, 2H) ppm; MS (ES) 497.5 (M+H).

Compound 2: $^1$H NMR (CDCl$_3$, 300 MHz) δ 8.20 (m, 2H), 8.13 (m, 1H), 7.77 (m, 1H), 7.61 (m, 2H), 7.47 (m, 4H), 7.30 (m, 1H), 6.89 (m, 2H), 4.66 (m, 1H), 3.98 (m, 1H), 3.60 (m, 4H), 3.35 (m, 2H), 2.81 (m, 2H), 2.23 (m, 2H), 2.04 (m, 6H), 1.62 (m, 2H) ppm; MS (ES) 521.6 (M+H).

Compound 3: $^1$H NMR (CDCl$_3$, 300 MHz) δ 8.54 (m, 2H), 8.20 (m, 1H), 8.13 (m, 1H), 7.77 (m, 1H), 7.49 (m, 2H), 7.29 (m, 3H), 6.95 (m, 2H), 4.63 (m, 1H), 3.99 (m, 1H), 3.60 (m, 2H), 3.52 (s, 2H), 3.27 (m, 2H), 2.82 (m, 2H), 2.23 (m, 2H), 2.06 (m, 6H), 1.66 (m, 2H) ppm; MS (ES) 540.5 (M+H).

Compound 4: $^1$H NMR (CDCl$_3$, 300 MHz) δ 8.20 (m, 1H), 8.12 (m, 1H), 7.77 (m, 1H), 7.61 (m, 2H), 7.47 (m, 4H), 7.30 (m, 1H), 6.95 (m, 2H), 4.63 (m, 1H), 3.99 (m, 1H), 3.58 (m, 4H), 3.27 (m, 2H), 2.80 (m, 2H), 2.31-1.88 (m, 8H), 1.64 (m, 2H) ppm; MS (ES) 564.5 (M+H).

Compound 5: $^1$H NMR (CDCl$_3$, 300 MHz) δ 8.53 (m, 2H), 8.20 (m, 1H), 8.13 (m, 1H), 7.77 (m, 1H), 7.66 (m, 1H), 7.48 (m, 2H), 7.29 (m, 2H), 6.95 (m, 2H), 4.63 (m, 1H), 3.99 (m, 1H), 3.59 (m, 2H), 3.53 (s, 2H), 3.27 (m, 2H), 2.84 (m, 2H), 2.27-1.88 (m, 8H), 1.64 (m, 2H) ppm; MS (ES) 540.6 (M+H).

Compound 6: $^1$H NMR (CDCl$_3$, 300 MHz) δ 8.54 (m, 2H), 8.20 (m, 1H), 8.13 (m, 1H), 7.76 (m, 1H), 7.66 (m, 1H), 7.50 (m, 2H), 7.29 (m, 2H), 6.89 (m, 2H), 4.65 (m, 1H), 3.98 (m, 1H), 3.63 (m, 2H), 3.53 (s, 2H), 3.35 (m, 2H), 2.83 (m, 2H), 2.22 (m, 2H), 2.03 (m, 6H), 1.63 (m, 2H) ppm; MS (ES) 497.6 (M+H).

Compound 7: $^1$H NMR (CDCl$_3$, 300 MHz) δ 8.20 (m, 1H), 8.13 (m, 1H), 7.99 (m, 2H), 7.76 (m, 1H), 7.50 (m, 2H), 7.40 (m, 2H), 7.30 (m, 1H), 6.89 (m, 2H), 4.66 (m, 1H), 3.99 (m, 1H), 3.91 (s, 3H), 3.63 (m, 2H), 3.56 (s, 2H), 3.33 (m, 2H), 2.83 (m, 2H), 2.21 (m, 2H), 2.04 (m, 6H), 1.64 (m, 2H) ppm; MS (ES) 554.6 (M+H).

Compound 8: $^1$H NMR (CDCl$_3$, 300 MHz) δ 8.20 (m, 1H), 8.13 (m, 1H), 7.98 (m, 1H), 7.77 (m, 1H), 7.48 (m, 2H), 7.41 (m, 2H), 7.309 (m, 1H), 6.95 (m, 2H), 4.62 (m, 1H), 3.97 (m, 1H), 3.91 (s, 3H), 3.580 (m, 4H), 3.27 (m, 2H), 2.83 (m, 2H), 2.27-1.89 (m, 8H), 1.64 (m, 2H) ppm; MS (ES) 597.6 (M+H).

Compound 9: $^1$H NMR (CDCl$_3$, 300 MHz) δ 8.52 (s, 1H), 7.96 (m, 1H), 7.46 (m, 2H), 6.94 (m, 2H), 6.74 (m, 1H), 5.82 (d, J=7.5 Hz, 1H), 5.32 (m, 1H), 4.02 (m, 2H), 3.62 (m, 2H), 3.24 (m, 2H), 2.83 (m, 2H), 2.27-1.76 (m, 8H), 1.59 (m, 2H), 1.46 (s, 9H) ppm; MS (ES) 549.5 (M+H).

Compound 10: $^1$H NMR (CDCl$_3$, 300 MHz) δ 8.54 (m, 3H), 7.96 (m, 1H), 7.47 (m, 2H), 7.28 (m, 2H), 6.95 (m, 2H), 6.75 (m, 1H), 5.85 (d, J=7.5 Hz, 1H), 5.32 (m, 1H), 4.01 (m, 1H), 3.62 (m, 2H), 3.52 (s, 2H), 3.24 (m, 2H), 2.83 (m, 2H), 2.27-1.76 (m, 8H), 1.59 (m, 2H) ppm; MS (ES) 540.6 (M+H).

Compound 11: $^1$H NMR (CDCl$_3$, 300 MHz) δ 8.52 (s, 1H), 7.96 (m, 1H), 7.47 (m, 2H), 7.29 (m, 2H), 6.98 (m, 4H), 6.73 (m, 1H), 5.81 (d, J=7.8 Hz, 1H), 5.32 (m, 1H), 3.99 (m, 1H), 3.62 (m, 2H), 3.47 (s, 2H), 3.24 (m, 2H), 2.82 (m, 2H), 2.22-1.84 (m, 8H), 1.54 (m, 2H) ppm; MS (ES) 557.6 (M+H).

Compound 12: $^1$H NMR (CDCl$_3$, 300 MHz) δ 8.32 (m, 1H), 8.01 (m, 1H), 7.74 (m, 1H), 7.47 (m, 2H), 6.93 (m, 3H), 4.74 (m, 1H), 3.99 (m, 1H), 3.56 (m, 2H), 3.26 (m, 2H), 2.84 (m, 2H), 2.34-1.79 (m, 8H), 1.65 (m, 2H), 1.46 (s, 9H) ppm; MS (ES) 549.6 (M+H).

Compound 13: $^1$H NMR (CDCl$_3$, 300 MHz) δ 8.54 (m, 2H), 8.34 (m, 1H), 8.00 (m, 1H), 7.72 (m, 1H), 7.48 (m, 2H), 7.27 (m, 2H), 6.93 (m, 3H), 4.74 (m, 1H), 3.99 (m, 1H), 3.58 (m, 2H), 3.52 (s, 2H), 3.27 (m, 2H), 2.83 (m, 2H), 2.31-1.78 (m, 8H), 1.66 (m, 2H) ppm; MS (ES) 540.6 (M+H).

Compound 14: $^1$H NMR (CDCl$_3$, 300 MHz) δ 8.48 (m, 4H), 7.67 (m, 1H), 7.47 (m, 2H), 7.27 (m, 2H), 6.95 (m, 2H), 6.07 (d, J=7.5 Hz, 1H), 4.63 (m, 1H), 4.03 (m, 1H), 3.60 (m, 2H), 3.53 (s, 2H), 3.25 (m, 2H), 2.85 (m, 2H), 2.24 (m, 2H), 2.18-1.88 (m, 6H), 1.62 (m, 2H) ppm; MS (ES) 540.6 (M+H).

Compound 15: $^1$H NMR (CDCl$_3$, 300 MHz) δ 7.74 (m, 3H), 7.51 (m, 2H), 6.98 (m, 2H), 6.88 (m, 1H), 5.21 (m, 1H), 4.02 (m, 1H), 3.60 (m, 2H), 3.31 (m, 2H), 2.80 (m, 2H), 2.35-1.91 (m, 8H), 1.64 (m, 2H), 1.46 (s, 9H) ppm; MS (ES) 549.3 (M+H).

Compound 16: $^1$H NMR (CDCl$_3$, 300 MHz) δ 8.44 (m, 2H), 7.66 (m, 1H), 7.48 (m, 2H), 7.28 (m, 2H), 6.98 (m, 4H), 5.97 (d, J=7.5 Hz, 1H), 4.63 (m, 1H), 4.01 (m, 1H), 3.60 (m, 2H), 3.48 (s, 2H), 3.25 (m, 2H), 2.83 (m, 2H), 2.22-1.91 (m, 8H), 1.56 (m, 2H) ppm; MS (ES) 557.6 (M+H).

Compound 17: $^1$H NMR (CDCl$_3$, 300 MHz) δ 8.48 (m, 1H), 8.42 (m, 1H), 7.64 (m, 3H), 7.48 (m, 4H), 6.95 (m, 2H), 4.63 (m, 1H), 4.05 (m, 1H), 3.60 (m, 4H), 3.25 (m, 2H), 2.87 (m, 2H), 2.27 (m, 2H), 2.18-1.88 (m, 6H), 1.54 (m, 2H) ppm; MS (ES) 564.5 (M+H).

Compound 18: $^1$H NMR (CDCl$_3$, 300 MHz) δ 8.51 (m, 4H), 7.69 (m, 2H), 7.48 (m, 2H), 7.28 (m, 1H), 6.95 (m, 2H), 6.17 (d, J=7.8 Hz, 1H), 4.63 (m, 1H), 4.03 (m, 1H), 3.61 (m, 4H), 3.25 (m, 2H), 2.89 (m, 2H), 2.25 (m, 2H), 2.18-1.88 (m, 6H), 1.66 (m, 2H) ppm; MS (ES) 540.6 (M+H).

Compound 19: $^1$H NMR (CD$_3$OD, 300 MHz) δ 7.80 (m, 6H), 7.14 (m, 1H), 7.07 (m, 1H), 5.79 (m, 1H), 4.19 (m, 1H), 3.91-3.44 (m, 6H), 3.16 (m, 2H), 2.43 (m, 2H), 2.11 (m, 7H) ppm; MS (ES) 449.7 (M+H).

Compound 20: $^1$H NMR (CDCl$_3$, 300 MHz) δ 8.53 (m, 2H), 7.70 (m, 3H), 7.49 (m, 2H), 7.28 (m, 2H), 6.97 (m, 2H), 6.89 (m, 1H), 5.22 (m, 1H), 4.01 (m, 1H), 3.61 (m, 2H), 3.52 (s, 2H), 3.30 (m, 2H), 2.81 (m, 2H), 2.31-1.94 (m, 8H), 1.63 (m, 2H) ppm; MS (ES) 540.6 (M+H).

Compound 21: $^1$H NMR (CDCl$_3$, 300 MHz) δ 7.75 (m, 2H), 7.59 (m, 3H), 7.46 (m, 4H), 6.98 (m, 2H), 6.89 (m, 1H), 5.22 (m, 1H), 3.99 (m, 1H), 3.59 (m, 2H), 3.55 (s, 2H), 3.29 (m, 2H), 2.78 (m, 2H), 2.21 (m, 4H), 2.03 (m, 4H), 1.62 (m, 2H) ppm; MS (ES) 564.6 (M+H).

Compound 22: $^1$H NMR (CDCl$_3$, 300 MHz) δ 7.76 (m, 3H), 7.49 (m, 2H), 7.28 (m, 2H), 6.99 (m, 4H), 6.87 (m, 1H), 5.20 (m, 1H), 4.01 (m, 1H), 3.61 (m, 2H), 3.47 (s, 2H), 3.29

(m, 2H), 2.80 (m, 2H), 2.18 (m, 4H), 2.01 (m, 4H), 1.56 (m, 2H) ppm; MS (ES) 557.6 (M+H).

Compound 23: $^1$H NMR (CDCl$_3$, 300 MHz) δ 8.20 (m, 2H), 8.13 (m, 1H), 7.92 (m, 1H), 7.50 (m, 2H), 7.31 (m, 1H), 7.01 (m, 2H), 4.65 (m, 2H), 3.71 (m, 1H), 3.64-3.22 (m, 7H), 2.21 (m, 3H), 2.01 (m, 3H), 1.46 (s, 9H) ppm; MS (ES) 535.2 (M+H).

Compound 24: $^1$H NMR (CD$_3$OD, 300 MHz) δ 8.50 (m, 1H), 8.22 (m, 1H), 7.85 (m, 3H), 7.61 (m, 2H), 5.04 (m, 1H), 4.68 (m, 1H), 3.92 (m, 2H), 3.77-3.52 (m, 4H), 3.41 (m, 2H), 2.42 (m, 3H), 2.25 (m, 2H) ppm; MS (ES) 435.6 (M+H).

Compound 25: $^1$H NMR (CDCl$_3$, 300 MHz) δ 8.54 (m, 2H), 8.20 (m, 1H), 8.11 (m, 2H), 7.48 (m, 2H), 7.31 (m, 3H), 6.96 (m, 2H), 4.63 (m, 2H), 3.68 (s, 2H), 3.60 (m, 2H), 3.26 (m, 2H), 2.72 (m, 2H), 2.42 (m, 2H), 2.11 (m, 3H), 1.98 (m, 3H) ppm; MS (ES) 526.6 (M+H).

Compound 44: $^1$H NMR (CDCl$_3$, 300 MHz) 9.16 (m, 1H), 8.77 (m, 2H), 8.20 (m, 1H), 8.12 (m, 1H), 7.80 (m, 1H), 7.48 (m, 2H), 7.29 (m, 1H), 6.95 (m, 2H), 4.63 (m, 1H), 4.01 (m, 1H), 3.59 (m, 4H), 3.27 (m, 2H), 2.92 (m, 2H), 2.35 (m, 2H), 2.04 (m, 6H), 1.76 (m, 2H) ppm; MS (ES) 541.9 (M+H).

Compound 45: $^1$H NMR (CDCl$_3$, 300 MHz) 8.52 (m, 1H), 7.98 (m, 2H), 7.43 (m, 4H), 7.28 (m, 2H), 6.95 (m, 2H), 6.76 (m, 1H), 5.83 (m, 1H), 5.32 (m, 1H), 3.93 (m, 5H), 3.59 (m, 4H), 3.24 (m, 2H), 2.84 (m, 2H), 2.04 (m, 8H) ppm; MS (ES) 597.8 (M+H).

Compound 46: $^1$H NMR (CD$_3$OD, 300 MHz) 8.62 (m, 1H), 8.12 (m, 3H), 7.64 (m, 2H), 7.46 (m, 2H), 7.06 (m, 2H), 6.82 (m, 1H), 5.32 (m, 1H), 4.41 (m, 2H), 4.15 (m, 1H), 3.66 (m, 2H), 3.51 (m, 2H), 3.26 (m, 4H), 2.19 (m, 4H), 1.89 (m, 4H) ppm; MS (ES) 583.6 (M+H).

Compound 47: $^1$H NMR (CDCl$_3$, 300 MHz) 8.16 (m, 2H), 7.74 (m, 1H), 7.48 (m, 1H), 7.32 (m, 12H), 7.13 (m, 6H), 6.95 (m, 2H), 6.18 (m, 1H), 4.61 (m, 1H), 3.94 (m, 1H), 3.54 (m, 4H), 3.27 (m, 2H), 2.87 (m, 2H), 2.21 (m, 4H), 1.97 (m, 4H), 1.25 (m, 2H) ppm; MS (ES) 529.6 (M+H).

Compound 48: $^1$H NMR (CD$_3$OD, 300 MHz) 9.09 (m, 1H), 8.50 (m, 1H), 8.20 (m, 1H), 7.95 (m, 1H), 7.82 (m, 5H), 4.59 (m, 1H), 4.20 (m, 1H), 3.81 (m, 8H), 2.47 (m, 2H), 2.21 (m, 8H) ppm; MS (ES) 529.7 (M+H).

Compound 49: $^1$H NMR (CDCl$_3$, 300 MHz) 8.12 (m, 3H), 7.52 (m, 2H), 7.22 (m, 1H), 6.94 (m, 2H), 5.10 (m, 1H), 4.62 (m, 1H), 3.55 (m, 3H), 3.24 (m, 3H), 2.11 (m, 2H), 1.97 (m, 2H), 1.76 (m, 4H), 1.44 (s, 9H) ppm; MS (ES) 523.5 (M+H).

Compound 50: $^1$H NMR (CDCl$_3$, 300 MHz) 8.22 (m, 5H), 7.60 (m, 4H), 7.25 (m, 1H), 6.91 (m, 2H), 4.9 (m, 1H), 4.63 (m, 1H), 3.52 (m, 5H), 3.22 (m, 3H), 2.13 (m, 2H), 1.95 (m, 2H), 1.73 (m, 4H) ppm; MS (ES) 514.5 (M+H).

(c) Assay Data

Compounds 1-50 of Table 1 were assayed for their ability to activate AMPK using an enzyme-linked immunosorbent assay. The EC$_{50}$ values for AMPK activation for compounds 1-50 are presented in Table 2 below, in which "A" is less than 0.1 µM; "B" is 0.1-0.5 µM; "C" is 0.5-1 µM; "D" is 1-5 µM; "E" is 5-10 µM; and "F" is >10 µM.

TABLE 2

| Cpd No. | AMPK EC$_{50}$ |
|---|---|
| 1 | B |
| 2 | A |
| 3 | A |
| 4 | A |
| 5 | A |
| 6 | B |
| 7 | A |
| 8 | A |
| 9 | B |
| 10 | A |
| 11 | A |
| 12 | C |
| 13 | B |
| 14 | A |
| 15 | D |
| 16 | A |
| 17 | A |
| 18 | A |
| 19 | D |
| 20 | C |
| 21 | B |
| 22 | D |
| 23 | B |
| 24 | E |
| 25 | B |
| 26 | B |
| 27 | F |
| 28 | A |
| 29 | B |
| 30 | A |
| 31 | A |
| 32 | B |
| 33 | C |
| 34 | C |
| 35 | B |
| 36 | C |
| 37 | C |
| 38 | D |
| 39 | B |
| 40 | A |
| 41 | B |
| 42 | D |
| 43 | D |
| 44 | B |
| 45 | F |
| 46 | D |
| 47 | D |
| 48 | D |
| 49 | A |
| 50 | D |

Example 2

(a) Synthetic Example

N-(1-(4-cyanobenzyl)piperidin-4-yl)-6-(1-(4-(trifluoromethyl)phenyl)piperidin-4-yloxy)pyridine-3-sulfonamide (compound 56)

Step 1. tert-butyl 4-(6-chloropyridine-3-sulfonamido)piperidine-1-carboxylate

To a stirred mixture of 6-chloropyridine-3-sulfonyl chloride (1 g, 4.717 mmol) in anhydrous dichloromethane (5 mL) was added triethylamine (790 µl, 5.66 mmol), and tert-butyl 4-aminopiperidine-1-carboxylate (945 mg, 4.717 mmol). The mixture was stirred at room temperature overnight and then poured into water. The resulting solids were collected by filtration to yield 1.7 g (99%) of tert-butyl 4-(6-chloropyridine-3-sulfonamido)piperidine-1-carboxylate as a white solid. $^1$H-NMR (CDCl$_3$, 300 MHz): δ 9.82 (s, 1H), 8.11 (dd, 1H), 7.43 (d, 1H), 4.62 (d, 1H), 3.91 (m, 2H), 3.36 (m, 1H), 2.80 (m, 2H), 3.97 (m, 1H), 1.81 (m, 2H), 1.40 (s, 9H), 1.18 (m, 2H); LCMS: MS (m/z): 376 (MH$^+$).

Step 2. tert-butyl 4-(6-(1-(4-(trifluoromethyl)phenyl) piperidin-4-yloxy)pyridine-3-sulfonamido)piperidine-1-carboxylate To a stirred solution of 1-(4-(trifluoromethyl)phenyl)-piperidin-4-ol (1.4 g, 5.71 mmol) in dimethylformamide (10 mL) at room temperature was added sodium hydride slowly (0.5 g, 60%, 12.4 mmol). After effervescence subsided, tert-butyl 4-(6-chloropyridine-3-sulfonamido)piperidine-1-carboxylate (1.03 g, 4.75 mmol) was added slowly. The mixture was stirred at room temperature overnight and then poured into ice-water. The residue was purified by flash chromatography (silica gel, 2% methanol in methylene chloride) to afford the title compound as a yellow solid (2.75 g, 99%). $^1$H-NMR (CDCl$_3$, 300 MHz): δ 8.64 (s, 1H), 7.97 (dd, 1H), 7.47 (d, 2H), 6.98 (d, 2H), 6.79 (d, 1H), 5.37 (m, 1H), 4.91 (d, 1H), 3.93 (m, 2H), 3.63 (m, 2H), 3.29 (m, 2H), 2.861 (m, 2H), 1.97 (m, 2H), 1.78 (m, 2H), 1.43 (s, 9H), 1.41 (m, 2H); LCMS: MS (m/z): 585 (MH$^+$)

Step 3. N-(1-(4-cyanobenzyl)piperidin-4-yl)-6-(1-(4-(trifluoromethyl)phenyl)piperidin-4-yloxy)pyridine-3-sulfonamide The compound from step b, above, was dissolved in 4N HCl in dioxane, and stirred for 1 h at room temperature. The reaction mixture was concentrated to dryness. The residue (100 mg, 0.168 mmol) and 4-cyanobenzaldehyde (33 mg, 0.247 mmol) were mixed in THF (5 mL) and treated with sodium triacetoxyborohydride (70 mg, 0.328 mmol). The mixture was stirred at room temperature under N$_2$ overnight. The reaction mixture was quenched with 1N NaOH, and extracted with EtOAc. The combined organic layers were washed with brine and dried over MgSO$_4$. The final product was purified by flash chromatography (2% MeOH/CH$_2$Cl$_2$) to afford the title compound (55 mg, 87%) as a white solid. $^1$H-NMR (CDCl$_3$, 300 MHz): δ 8.62 (s, 1H), 7.97 (dd, 1H), 7.61 (d, 2H), 7.52 (d, 2H), 7.40 (d, 1H), 6.95 (d, 2H), 6.79 (d, 1H), 5.34 (m, 1H), 4.62 (m, 1H), 3.63 (m, 2H), 3.52 (s, 2H), 3.26 (m, 2H), 2.72 (m, 2H), 2.12 (m, 2H), 1.98 (m, 4H), 1.53 (m, 4H); LCMS: MS (m/z): 600 (MH$^+$).

(b) Assay Data

Compounds 51-60 of Table 1 were assayed for their ability to activate AMPK using an enzyme-linked immunosorbent assay. The EC$_{50}$ values for AMPK activation for compounds 51-60 are presented in Table 3 below, in which "A" is less than 0.1 µM; "B" is 0.1-0.5 µM; "C" is 0.5-1 µM; "D" is 1-5 µM; "E" is 5-50 µM; and "F" is >50 µM.

TABLE 3

| Cpd No. | AMPK EC$_{50}$ |
|---|---|
| 51 | B |
| 52 | B |
| 53 | B |
| 54 | D |
| 55 | D |
| 56 | E |
| 57 | C |
| 58 | A |
| 59 | B |
| 60 | F |

Example 3

(a) Synthetic Example

N-(1-benzylpiperidin-4-yl)-5-(1-(4-cyanobenzyl) piperidin-4-yloxy)benzofuran-2-carboxamide (compound 70)

Step 1. 5-Hydroxybenzofuran-2-carboxylic acid

A solution of 5-methoxybenzofuran-2-carboxylic acid ethyl ester (5.506 g, 25 mmol) in anhydrous CH$_2$Cl$_2$ (15 mL) was cooled to −40° C. under N$_2$ atmosphere. BBr$_3$ (1.0 M in CH$_2$Cl$_2$, 27 mL) was added over 1 h using dropping funnel. The reaction mixture was allowed to warm to room temperature. After over-night, the reaction mixture was cooled in an ice-bath and quenched with brine (100 mL) and extracted with ethyl acetate (3×100 mL), dried (Na$_2$SO$_4$) and concentrated. Finally dried under high vacuum to furnish 3.11 g (70%) of the desired product 2. $^1$H NMR (DMSO-d$_6$, 300 MHz): δ 13.3 (s, 1H), 7.48 (m, 2H), 7.02 (s, 1H), 6.94 (m, 1H);
LCMS (m/z): 179 (MH$^+$).

Step 2. N-(1-Benzylpiperidin-4-yl)-5-hydroxybenzofurancarboxamide

To a stirred mixture of 5-hydroxybenzofuran-2-carboxylic acid (1.02 g, 5.74 mmol) in anhydrous dimethylformamide (12 mL) was added triethylamine (0.96 mL), 1-hydroxybenzotriazole (0.91 g), 1-(3-dimethylaminopropyl)-3-ethylcarbodiimide hydrochloride (1.33 g) and 1-benzylpiperidin-4-ylamine (1.33 g). The reaction mixture was stirred at room temperature over-night and then solvents were removed under reduced pressure, poured into water, filter the solid and washed with water. The solid was purified by silica gel column chromatography, eluted with CH$_2$Cl$_2$: MeOH (95:5) to afford 0.72 g (36%) of 3 as a white solid. $^1$H NMR (DMSO-d$_6$, 300 MHz): δ 9.33 (s, 1H), 8.42 (d, J=8.1 Hz, 1H), 7.40 (d, J=8.7 Hz, 1H), 7.34 (s, 1H), 7.28 (m, 5H), 6.98 (d, J=2.1 Hz, 1H), 6.86 (dd, J=2.4 and 8.8 Hz, 1H), 3.74 (br s, 1H), 3.44 (s, 2H), 2.80 (d, J=10.8 Hz, 2H), 1.99 (t, J=11.1 Hz, 2H), 1.99 (m, 4H), 1.66 (m, 4H); LCMS (m/z): 351 (MH$^+$).

Step 3. N-(1-benzylpiperidin-4-yl)-5-(1-(4-cyanobenzyl)piperidin-4-yloxy)benzofuran-2-carboxamide To a stirred mixture of N-(1-Benzylpiperidin-4-yl)-5-hydroxybenzofurancarboxamide (85 mg, 0.245 mmol) in anhydrous toluene (3 mL) at room temperature was added diisopropyl azodicarboxylate (0.05 mL, 0.25 mmol), 1-(4-cyanobenzyl)piperidin-4-ol (53 mg, 0.245 mmol) and triphenylphosphine (64 mg, 0.25 mmol). The reaction was stirred at 80° C. under N$_2$ atmosphere overnight and then concentrated under reduced pressure. The residue thus obtained was purified by silica gel column chromatography, eluted with CH$_2$Cl$_2$: MeOH (97:3) to afford 50 mg (37%) of compound 10 as a white solid. $^1$H NMR (DMSO-d$_6$, 300 MHz): δ 8.48 (d, J=8.1 Hz, 1H), 7.77 (d, J=8.1 Hz, 2H), 7.50 (d, J=7.8 Hz, 3H), 7.38 (s, 1H), 7.28 (m, 6H), 7.01 (d, J=8.1 Hz, 1H), 4.37 (br s, 1H), 3.76 (br s, 1H), 3.57 (s, 2H), 3.44 (s, 2H), 2.80 (d, J=10.5 Hz, 2H), 2.65 (br s, 2H), 2.26 (t, J=9.9 Hz, 2H), 1.99 (m, 4H), 1.66 (m, 6H); LCMS (m/z): 549 (MH$^+$)

(b) Analytical Data

The following compounds were prepared using methods analogous to those described in Example 3(a) and in Scheme 3.

Compound 61: tert-butyl 4-(3-methyl-6-(1-(4-(trifluoromethyl)phenyl)piperidin-4-yloxy)benzofuran-2-carboxamido)piperidine-1-carboxylate. $^1$H NMR (CDCl$_3$, 300 MHz) δ 7.46 (m, 2H), 7.27 (m, 1H), 6.98 (m, 4H), 6.38 (d, J=7.8 Hz, 1H), 4.55 (m, 1H), 3.98 (m, 1H), 3.61 (m, 2H), 3.25 (m, 2H), 2.84 (m, 2H), 2.58 (s, 3H), 2.25-1.92 (m, 8H), 1.56 (m, 2H), 1.46 (s, 9H) ppm; MS (ES) 602.4 (M+H).

Compound 62: 3-methyl-N-(piperidin-4-yl)-6-(1-(4-(trifluoromethyl)phenyl)piperidin-4-yloxy)benzofuran-2-carboxamide. $^1$H NMR (CD$_3$OD, 300 MHz) δ 7.61 (m, 3H), 7.37 (m, 2H), 7.18 (m, 1H), 7.06 (m, 1H), 4.76 (m, 1H), 4.17 (m, 1H), 3.82-3.41 (m, 6H), 3.13 (m, 2H), 2.55 (s, 3H), 2.31-1.82 (m, 9H) ppm; MS (ES) 502.5 (M+H).

Compound 63: N-(1-(4-fluorobenzyl)piperidin-4-yl)-3-methyl-6-(1-(4-(trifluoromethyl)phenyl)piperidin-4-yloxy)benzofuran-2-carboxamide. $^1$H NMR (CDCl$_3$, 300 MHz) δ 7.47 (m, 2H), 7.28 (m, 3H), 6.98 (m, 6H), 6.39 (d, J=7.8 Hz, 1H), 4.56 (m, 1H), 3.99 (m, 1H), 3.60 (m, 2H), 3.48 (s, 2H), 3.24 (m, 2H), 2.84 (m, 2H), 2.58 (s, 3H), 2.22-1.91 (m, 8H), 1.56 (m, 2H) ppm; MS (ES) 610.6 (M+H).

Compound 64: N-(1-(4-cyanobenzyl)piperidin-4-yl)-3-methyl-6-(1-(4-(trifluoromethyl)phenyl)piperidin-4-yloxy)benzofuran-2-carboxamide. $^1$H NMR (CDCl$_3$, 300 MHz) δ 7.61 (m, 2H), 7.47 (m, 5H), 6.96 (m, 4H), 6.40 (d, J=7.2 Hz, 1H), 4.56 (m, 1H), 4.01 (m, 1H), 3.58 (m, 4H), 3.28 (m, 2H), 2.82 (m, 2H), 2.58 (s, 3H), 2.26-1.91 (m, 8H), 1.56 (m, 2H) ppm; MS (ES) 617.6 (M+H).

Compound 65: 3-methyl-N-(1-(pyridin-4-ylmethyl)piperidin-4-yl)-6-(1-(4-(trifluoromethyl)phenyl)piperidin-4-yloxy)benzofuran-2-carboxamide. $^1$H NMR (CD$_3$OD, 300 MHz) δ 8.49 (m, 2H), 7.54 (m, 1H), 7.46 (m, 4H), 7.14 (m, 1H), 7.06 (m, 2H), 6.99 (m, 1H), 4.66 (m, 1H), 3.93 (m, 1H), 3.65 (m, 4H), 3.25 (m, 2H), 2.95 (m, 2H), 2.53 (s, 3H), 2.28 (m, 2H), 2.13 (m, 2H), 2.02-1.69 (m, 6H) ppm; MS (ES) 593.3 (M+H).

Compound 66: N-(1-(3-cyanobenzyl)piperidin-4-yl)-3-methyl-6-(1-(4-(trifluoromethyl)phenyl)piperidin-4-yloxy)benzofuran-2-carboxamide. $^1$H NMR (CD$_3$OD, 300 MHz) δ 7.81 (m, 1H), 7.72 (m, 2H), 7.56 (m, 2H), 7.47 (m, 2H), 7.05 (m, 4H), 4.67 (m, 1H), 3.93 (m, 1H), 3.87 (s, 2H), 3.66 (m, 2H), 3.26 (m, 2H), 3.12 (m, 2H), 2.54 (m, 5H), 2.18-1.74 (m, 8H) ppm; MS (ES) 617.3 (M+H).

Compound 67: N-(1-(2-cyanobenzyl)piperidin-4-yl)-3-methyl-6-(1-(4-(trifluoromethyl)phenyl)piperidin-4-yloxy)benzofuran-2-carboxamide. $^1$H NMR (CD$_3$OD, 300 MHz) δ 7.72 (m, 1H), 7.62 (m, 2H), 7.53 (m, 1H), 7.45 (m, 3H), 7.14 (m, 1H), 7.04 (m, 2H), 6.98 (m, 1H), 4.66 (m, 1H), 3.91 (m, 1H), 3.73 (s, 2H), 3.64 (m, 2H), 3.25 (m, 2H), 2.94 (m, 2H), 2.53 (s, 3H), 2.29 (m, 2H), 2.11 (m, 2H), 1.90 (m, 4H), 1.74 (m, 2H) ppm; MS (ES) 617.3 (M+H);

Compound 71: N-(1-benzylpiperidin-4-yl)-5-(1-(4-cyanophenyl)piperidin-4-yloxy)benzofuran-2-carboxamide formate salt. $^1$H NMR (DMSO-d$_6$, 300 MHz): δ 9.51 (s, 1H), 8.78 (d, J=7.2 Hz, 1H), 7.47 (m, 7H), 7.33 (d, J=2.4 Hz, 1H), 7.05 (m, 3H), 4.63 (br s, 1H), 4.28 (d, J=4.8 Hz, 2H), 3.99 (s, 1H), 3.71 (m, 2H), 3.37 (s, 2H), 3.27 (t, J=8.7 Hz, 3H), 3.10 (m, 2H), 2.00 (m, 4H), 1.84 (m, 2H), 1.66 (m, 2H); LCMS (m/z): 535 (MH$^+$).

Compound 72: N-(1-benzylpiperidin-4-yl)-5-(1-(4-chlorobenzyl)piperidin-4-yloxy)benzofuran-2-carboxamide. $^1$H NMR (DMSO-d$_6$, 300 MHz): δ 8.47 (d, J=7.8 Hz, 1H), 7.49 (d, J=8.7 Hz, 1H), 7.38-7.26 (m, 11H), 7.01 (dd, J=2.1 and 9.1 Hz, 1H), 4.36 (br s, 1H), 3.73 (br s, 1H), 3.47 (s, 2H), 3.45 (s, 2H), 2.81 ((d, J=10.2 Hz, 2H), 2.64 (m, 2H), 2.23 (t, J=9.6 Hz, 2H), 1.96 (m, 4H), 1.71 (m, 6H); LCMS (m/z): 558 (MH$^+$).

Compound 73: N-(1-benzylpiperidin-4-yl)-5-(1-(3-(trifluoromethyl)benzyl)piperidin-4-yloxy)benzofuran-2-carboxamide. $^1$H NMR (DMSO-d$_6$, 300 MHz): δ 8.47 (d, J=8.1 Hz, 1H), 7.60 (m, 4H), 7.49 (d, J=9.3 Hz, 1H), 7.38 (d, J=0.9 Hz, 1H), 7.27 (m, 6H), 7.02 (dd, J=2.4 and 9.0 Hz, 1H), 4.38 (br s, 1H), 3.74 (br s, 1H), 3.59 (s, 2H), 3.46 (s, 2H), 2.82 ((d, J=10.8 Hz, 2H), 2.66 (m, 2H), 2.27 (t, J=9.6 Hz, 2H), 1.95 (m, 4H), 1.67 (m, 7H); LCMS (m/z): 592 (MH$^+$)

Compound 74: N-(1-benzylpiperidin-4-yl)-5-(1-(3,4-difluorobenzyl)piperidin-4-yloxy)benzofuran-2-carboxamide. $^1$H NMR (DMSO-d$_6$, 300 MHz): δ 8.49 (d, J=8.1 Hz, 1H), 7.50 (d, J=8.7 Hz, 1H), 7.33 (m, 9H), 7.14 (m, 1H), 7.02 (dd, J=2.4 and 9.0 Hz, 1H), 4.36 (br s, 1H), 3.73 (br s, 1H), 3.47 (s, 2H), 3.44 (s, 2H), 2.80 (d, J=10.5 Hz, 2H), 2.65 (m, 2H), 2.23 (t, J=9.0 Hz, 2H), 1.95 (m, 4H), 1.65 (m, 6H); LCMS (m/z): 560 (MH$^+$).

Compound 75: N-(1-benzylpiperidin-4-yl)-5-(1-(4-(trifluoromethyl)phenyl)piperidin-4-yloxy)benzofuran-2-carboxamide. $^1$H NMR (DMSO-d$_6$, 300 MHz): δ 8.48 (d, J=7.5 Hz, 1H), 7.62-7.45 (m, 5H), 7.41 (s, 1H), 7.31 (m, 5H), 7.06 (dd, J=2.7 and 9.0 Hz, 1H), 4.61 (m, 1H), 3.70 (m, 3H), 3.45 (s, 2H), 3.22 (t, J=9.9 Hz, 2H), 2.81 (d, J=9.0 Hz, 2H), 2.01 (m, 4H), 1.68 (m, 6H); LCMS (m/z): 578 (MH$^+$).

Compound 76: N-(1-(pyridin-4-ylmethyl)piperidin-4-yl)-5-(1-(4-(trifluoromethyl)phenyl)piperidin-4-yloxy)benzofuran-2-carboxamide. $^1$H NMR (DMSO-d$_6$, 300 MHz): δ 8.50 (m, 2H), 7.52 (d, J=9.3 Hz, 2H), 7.47 (d, J=9.0 Hz, 2H), 7.41 (s, 1H), 7.31 (m, 3H), 7.07 (d, J=8.1 Hz, 3H), 4.61 (m, 1H), 3.76 (m, 1H), 3.67 (m, 2H), 3.50 (s, 2H), 3.22 (t, J=9.6 Hz, 2H), 2.80 (d, J=11.1 Hz, 2H), 2.04 (d, J=10.5 Hz, 4H), 1.71 (m, 6H); LCMS (m/z): 579 (MH$^+$).

Compound 77: 5-(1-(4-chlorobenzyl)piperidin-4-yloxy)-N-(1-(pyridin-4-ylmethyl)piperidin-4-yl)benzofuran-2-carboxamide. $^1$H NMR (DMSO-d$_6$, 300 MHz): δ 8.49 (m, 2H), 7.49 (d, J=9.3 Hz, 2H), 7.39-7.25 (m, 8H), 7.01 (dd, J=2.4 and 9.0 Hz, 1H), 4.36 (m, 1H), 3.75 (m, 1H), 3.49 (s, 2H), 3.47 (s, 2H), 2.79 (d, J=11.4 Hz, 2H), 2.64 (m, 2H), 2.22 (t, J=8.4 Hz, 2H), 2.05 (m, 2H), 1.92 (m, 2H), 1.65 (m, 6H); LCMS (m/z): 559 (MH$^+$).

Compound 78: N-(1-(pyridin-4-ylmethyl)piperidin-4-yl)-5-(1-(4-(trifluoromethoxy)phenyl)piperidin-4-yloxy)benzofuran-2-carboxamide trifluoroacetate salt. $^1$H NMR (DMSO-d$_6$, 300 MHz): δ 9.76 (s, 1H), 8.78 (d, J=7.5 Hz, 1H), 7.71 (d, J=6.0 Hz, 2H), 7.55 (m, 2H), 7.44 (s, 1H), 7.34 (s, 1H), 7.18 (d, J=8.7 Hz, 2H), 7.08 (d, J=9.0 Hz, 2H), 7.02 (d, J=9.0 Hz, 2H), 4.57 (s, 2H), 4.34 (s, 2H), 4.02 (m, 2H), 3.45 (m, 3H), 3.09 (m, 3H), 2.03 (m, 4H), 1.85-1.71 (m, 4H); LCMS (m/z): 595 (MH$^+$).

Compound 79: 5-(1-(4-cyanobenzyl)piperidin-4-yloxy)-N-(1-(pyridin-4-ylmethyl)piperidin-4-yl)benzofuran-2-carboxamide. $^1$H NMR (DMSO-d$_6$, 300 MHz): δ 8.49 (m, 2H), 7.49 (d, J=9.3 Hz, 2H), 7.39-7.25 (m, 8H), 7.01 (dd, J=2.4 and 9.0 Hz, 1H), 4.36 (m, 1H), 3.75 (m, 1H), 3.49 (s, 2H), 3.47 (s, 2H), 2.79 (d, J=11.4 Hz, 2H), 2.64 (m, 2H), 2.22 (t, J=8.4 Hz, 2H), 2.05 (m, 2H), 1.92 (m, 2H), 1.65 (m, 6H); LCMS (m/z): 550 (MH$^+$).

Compound 80: N-(1-benzylpiperidin-4-yl)-5-(1-(4-(trifluoromethoxy)phenyl)piperidin-4-yloxy)benzofuran-2-carboxamide trifluoroacetate salt. $^1$H NMR (DMSO-d$_6$, 300 MHz): δ 9.46 (s, 1H), 8.78 (d, J=7.8 Hz, 1H), 7.47 (m, 6H), 7.33 (s, 1H), 7.16 (d, J=8.7 Hz, 2H), 7.06 (dd, J=2.4 and 8.7 Hz, 1H), 7.01 (d, J=8.7 Hz, 2H), 4.57 (s, 2H), 4.28 (d, J=4.8

Hz, 4H), 3.51 (m, 2H), 3.40 (d, J=11.1 Hz, 2H), 3.09 (t, J=9.6 Hz, 3H), 2.02 (m, 3H), 1.79 (m, 4H); LCMS (m/z): 594 (MH+).

Compound 81: tert-butyl 4-(6-(1-(4-(trifluoromethoxy)phenyl)piperidin-4-yloxy)benzofuran-2-carboxamido)piperidine-1-carboxylate. $^1$H NMR (CDCl$_3$, 300 MHz): δ 7.66 (m, 1H), 7.53 (d, J=9.0 Hz, 1H), 7.45 (m, 1H), 7.39 (s, 1H), 7.10 (d, J=8.7 Hz, 2H), 7.02 (s, 1H), 6.93 (m, 3H), 6.40 (d, J=7.8 Hz, 1H), 6.32 (s, 1H), 4.52 (m, 1H), 4.12 (m, 3H), 3.49 (m, 2H), 3.13 (m, 2H), 2.93 (t, J=12.0 Hz, 2H), 2.04 (m, 5H), 1.48 (s, 9H); LCMS (m/z): 604 (MH+)

Compound 82: tert-butyl 4-(6-(1-(4-(trifluoromethyl)phenyl)piperidin-4-yloxy)benzofuran-2-carboxamido)piperidine-1-carboxylate. $^1$H NMR (DMSO-d$_6$, 300 MHz): δ 8.85 (s, 1H), 8.40 (d, J=7.8 Hz, 1H), 7.61 (d, J=8.7 Hz, 1H), 7.46 (m, 3H), 7.26 (s, 1H), 7.07 (d, J=8.7 Hz, 2H), 6.98 (d, J=8.7 Hz, 1H), 4.72 (m, 2H), 3.93 (m, 3H), 3.68 (m, 2H), 3.23 (t, J=9.6 Hz, 2H), 2.81 (br s, 2H), 2.04 (m, 2H), 1.73 (m, 4H), 1.40 (s, 9H); LCMS (m/z): 588 (MH+).

Compound 83: N-(piperidin-4-yl)-6-(1-(4-(trifluoromethoxy)phenyl)piperidin-4-yloxy)benzofuran-2-carboxamide hydrochloride. $^1$H NMR (DMSO-d$_6$, 300 MHz): δ 8.85 (s, 1H), 8.76 (br s, 1H), 8.65 (d, J=7.5 Hz, 1H), 7.56 (m, 3H), 7.22 (m, 2H), 7.13 (s, 1H), 6.99 (d, J=8.1 Hz, 1H), 4.71 (m, 2H), 3.55 (m, 2H), 3.30 (d, J=11.7 Hz, 2H), 3.15 (t, J=8.7 Hz, 2H), 2.99 (m, 2H), 2.09 (m, 2H), 1.94 (m, 2H), 1.80 (m, 3H); LCMS (m/z): 504 (MH+).

Compound 84: N-(piperidin-4-yl)-6-(1-(4-(trifluoromethyl)phenyl)piperidin-4-yloxy)benzofuran-2-carboxamide hydrochloride. $^1$H NMR (DMSO-d$_6$, 300 MHz): δ 8.82 (m, 1H), 8.65 (d, J=7.5 Hz, 1H), 7.62 (d, J=8.4 Hz, 1H), 7.49 (m, 2H), 7.27 (s, 1H), 7.08 (d, J=9.0 Hz, 2H), 6.99 (dd, J=1.5 and 8.7 Hz, 1H), 4.71 (m, 1H), 4.04 (m, 1H), 3.66 (m, 2H), 3.27 (m, 3H), 2.99 (m, 2H), 2.05 (m, 2H), 1.93 (m, 2H), 1.77 (m, 4H); LCMS (m/z): 488 (MH+).

Compound 85: tert-butyl 4-(5-(1-(4-(trifluoromethyl)phenyl)piperidin-4-yloxy)benzofuran-2-carboxamido)piperidine-1-carboxylate. $^1$H NMR (DMSO-d$_6$, 300 MHz): δ 8.53 (d, J=8.1 Hz, 1H), 7.49 (m, 4H), 7.33 (d, J=2.1 Hz, 1H), 7.07 (d, J=8.7 Hz, 3H), 4.61 (m, 1H), 3.93 (m, 3H), 3.67 (m, 2H), 3.22 (m, 3H), 2.81 (br s, 3H), 2.02 (m, 2H), 1.73 (m, 4H), 1.40 (s, 9H); LCMS (m/z): 588 (MH+).

Compound 86: N-(piperidin-4-yl)-5-(1-(4-(trifluoromethyl)phenyl)piperidin-4-yloxy)benzofuran-2-carboxamide hydrochloride. $^1$H NMR (DMSO-d$_6$, 300 MHz): δ 8.84 (m, 1H), 8.77 (d, J=7.5 Hz, 1H), 7.70 (m, 1H), 7.49 (m, 3H), 7.34 (s, 1H), 7.08 (d, J=9.0 Hz, 3H), 4.62 (m, 1H), 4.05 (m, 1H), 3.66 (m, 2H), 3.27 (m, 3H), 2.99 (m, 2H), 1.97 (m, 4H), 1.78 (m, 4H); LCMS (m/z): 488 (MH+).

Compound 87: $^1$H NMR (DMSO-d$_6$, 300 MHz): δ 8.49 (d, J=5.1 Hz, 2H), 8.37 (d, J=8.4 Hz, 1H), 7.61 (d, J=9.0 Hz, 1H), 7.46 (m, 3H), 7.29 (m, 3H), 7.07 (d, J=8.7 Hz, 2H), 6.98 (d, J=8.4 Hz, 1H), 4.70 (m, 1H), 4.68 (m, 3H), 3.50 (s, 1H), 3.23 (t, J=9.9 Hz, 2H), 2.79 (t, J=11.7 Hz, 2H), 2.06 (t, J=9.3 Hz, 4H), 1.69 (m, 6H); LCMS (m/z): 579 (MH+).

Compound 88: $^1$H NMR (DMSO-d$_6$, 300 MHz): δ 8.48 (d, J=5.4 Hz, 2H), 8.36 (d, J=7.8 Hz, 1H), 7.60 (d, J=8.7 Hz, 1H), 7.44 (s, 1H), 7.30 (d, J=5.7 Hz, 2H), 7.26 (s, 1H), 7.16 (d, J=8.4 Hz, 2H), 7.00 (m, 3H), 4.66 (m, 1H), 3.75 (m, 1H), 3.56 (m, 2H), 3.50 (s, 2H), 3.10 (t, J=9.0 Hz, 2H), 2.79 (d, J=11.1 Hz, 2H), 2.06 (t, J=9.3 Hz, 4H), 1.69 (m, 6H); LCMS (m/z): 595 (MH+).

Compound 89: $^1$H NMR (DMSO-d$_6$, 300 MHz): δ 8.35 (d, J=8.1 Hz, 1H), 7.78 (d, J=8.4 Hz, 2H), 7.56 (m, 3H), 7.43 (s, 1H), 7.26 (s, 1H), 7.16 (d, J=8.4 Hz, 2H), 7.00 (m, 3H), 4.65 (br s, 1H), 3.74 (br s, 1H), 3.55 (s, 2H), 3.50 (m, 2H), 3.10 (t, J=9.3 Hz, 2H), 2.79 (d, J=11.1 Hz, 2H), 2.06 (t, J=10.8 Hz, 4H), 1.74 (m, 4H), 1.63 (m, 2H); LCMS (m/z): 619 (MH+).

Compound 90: $^1$H NMR (DMSO-d$_6$, 300 MHz): δ 8.36 (d, J=7.8 Hz, 1H), 7.78 (d, J=8.1 Hz, 2H), 7.60 (d, J=8.7 Hz, 1H), 7.48 (m, 4H), 7.27 (s, 1H), 7.07 (d, J=8.4 Hz, 2H), 6.97 (d, J=8.1 Hz, 1H), 4.70 (br s, 1H), 3.68 (br s, 3H), 3.55 (s, 2H), 3.23 (t, J=10.2 Hz, 3H), 2.78 (d, J=11.7 Hz, 2H), 2.06 (t, J=10.5 Hz, 4H), 1.69 (m, 6H); LCMS (m/z): 603 (MH+).

Compound 91: $^1$H NMR (DMSO-d$_6$, 300 MHz): δ 8.35 (d, J=7.8 Hz, 2H), 7.60 (d, J=9.0 Hz, 1H), 7.46 (t, J=9.0 Hz, 3H), 7.30 (m, 3H), 7.09 (m, 4H), 6.97 (dd, J=2.1 and 8.4 Hz, 1H), 4.70 (m, 1H), 3.67 (m, 3H), 3.43 (s, 2H), 3.26 (m, 2H), 2.79 (d, J=11.4 Hz, 2H), 2.03 (m, 4H), 1.71-1.54 (m, 6H); LCMS (m/z): 596 (MH+).

Compound 92: $^1$H NMR (DMSO-d$_6$, 300 MHz): δ 8.46 (d, J=4.8 Hz, 1H), 7.37 (d, J=8.1 Hz, 1H), 7.74 (t, J=7.5 Hz, 1H), 7.60 (d, J=8.7 Hz, 1H), 7.44 (s, 1H), 7.41 (d, J=7.5 Hz, 1H), 7.24 (m, 2H), 7.16 (d, J=8.7 Hz, 2H), 6.99 (m, 3H), 4.66 (m, 1H), 3.77 (m, 1H), 3.57 (s, 2H), 3.52 (m, 2H), 2.09 (t, J=9.3 Hz, 2H), 2.83 (d, J=11.7 Hz, 2H), 2.09 (t, J=9.9 Hz, 4H), 1.73 (m, 6H); LCMS (m/z): 595 (MH+).

Compound 93: $^1$H NMR (DMSO-d$_6$, 300 MHz): δ 8.46 (d, J=4.8 Hz, 1H), 7.37 (d, J=7.8 Hz, 1H), 7.75 (t, J=7.8 Hz, 1H), 7.60 (d, J=9.0 Hz, 1H), 7.44 (m, 4H), 7.27 (s, 1H), 7.23 (d, J=7.2 Hz, 1H), 7.07 (d, J=8.7 Hz, 2H), 6.98 (d, J=8.7 Hz, 1H), 4.70 (m, 1H), 3.71 (m, 3H), 3.57 (s, 2H), 2.23 (t, J=9.9 Hz, 2H), 2.83 (d, J=11.4 Hz, 2H), 2.09 (t, J=9.9 Hz, 4H), 1.69 (m, 6H); LCMS (m/z): 579 (MH+).

Compound 94: $^1$H NMR (DMSO-d$_6$, 300 MHz): δ 8.36 (d, J=7.8 Hz, 1H), 7.58 (m, 4H), 7.43 (s, 1H), 7.29 (m, 2H), 7.14 (m, 3H), 6.99 (m, 2H), 4.65 (m, 1H), 3.74 (m, 1H), 3.51 (m, 2H), 3.43 (s, 2H), 3.09 (t, J=10.2 Hz, 2H), 2.79 (d, J=11.1 Hz, 2H), 1.99 (t, J=11.1 Hz, 4H), 1.72 (m, 4H), 1.61 (m, 2H); LCMS (m/z): 612 (MH+).

Compound 95: $^1$H NMR (DMSO-d$_6$, 300 MHz): δ 8.50 (s, 3H), 7.72 (s, 1H), 7.61 (d, J=8.7 Hz, 1H), 7.45 (s, 1H), 7.38 (s, 1H), 7.25 (s, 1H), 7.16 (d, J=8.4 Hz, 2H), 7.00 (t, J=9.3 Hz, 3H), 4.65 (s, 1H), 3.79 (m, 1H), 3.53 (m, 2H), 3.39 (s, 2H), 3.09 (t, J=9.3 Hz, 3H), 2.82 (m, 2H), 2.04 (m, 3H), 1.73 (m, 6H); LCMS (m/z): 595 (MH+).

Compound 96: $^1$H NMR (DMSO-d$_6$, 300 MHz): δ 8.47 (s, 1H), 8.44 (d, J=4.2 Hz, 1H), 7.36 (d, J=8.1 Hz, 1H), 7.68 (d, J=7.8 Hz, 1H), 7.60 (d, J=9.0 Hz, 1H), 7.47 (d, J=8.7 Hz, 2H), 7.43 (s, 1H), 7.33 (dd, J=4.8 and 7.6 Hz, 2H), 7.26 (s, 1H), 7.07 (d, J=8.7 Hz, 2H), 6.97 (dd, J=1.8 and 8.5 Hz, 2H), 4.70 (m, 1H), 3.68 (m, 2H), 3.49 (s, 2H), 3.25 (m, 3H), 2.80 (d, J=11.7 Hz, 2H), 2.03 (t, J=10.2 Hz, 4H), 1.73-1.57 (m, 6H); LCMS (m/z): 579 (MH+).

Compound 97: $^1$H NMR (DMSO-d$_6$, 300 MHz): δ 8.37 (d, J=7.8 Hz, 1H), 7.79 (d, J=7.5 Hz, 1H), 7.69-7.54 (m, 4H), 7.44 (m, 2H), 7.26 (s, 1H), 7.16 (d, J=9.0 Hz, 2H), 6.99 (m, 3H), 4.65 (m, 2H), 3.76 (m, 1H), 3.63 (s, 2H), 3.54 (m, 2H), 3.09 (t, J=10.5 Hz, 2H), 2.81 (d, J=11.1 Hz, 2H), 2.10 (m, 4H), 1.74 (m, 4H), 1.62 (s, 2H); LCMS (m/z): 619 (MH+).

Compound 98: $^1$H NMR (DMSO-d$_6$, 300 MHz): δ 8.37 (d, J=8.4 Hz, 1H), 7.79 (d, J=7.5 Hz, 1H), 7.69-7.53 (m, 4H), 7.44 (m, 3H), 7.27 (s, 1H), 7.07 (d, J=8.7 Hz, 2H), 6.96 (d, J=8.4 Hz, 1H), 4.73 (m, 1H), 3.70 (m, 2H), 3.63 (s, 2H), 3.25 (m, 3H), 2.81 (d, J=11.4 Hz, 2H), 2.10 (m, 4H), 1.73-1.59 (m, 6H); LCMS (m/z): 603 (MH+).

Compound 99: $^1$H NMR (DMSO-d$_6$, 300 MHz): δ 8.34 (d, J=7.5 Hz, 1H), 7.67 (d, J=7.5 Hz, 2H), 7.61 (d, J=9.0 Hz, 1H), 7.49 (m, 5H), 7.26 (s, 1H), 7.07 (d, J=8.7 Hz, 2H), 6.97 (d, J=8.4 Hz, 1H), 4.70 (m, 1H), 3.68 (m, 3H), 3.55 (s, 2H), 3.23 (t, J=9.6 Hz, 2H), 2.80 (d, J=10.5 Hz, 2H), 2.06 (t, J=10.5 Hz, 4H), 1.74-1.61 (m, 6H); LCMS (m/z): 646 (MH+).

Compound 100: ¹H NMR (DMSO-d₆, 300 MHz): δ 8.50 (d, J=7.8 Hz, 1H), 7.67 (d, J=6.9 Hz, 2H), 7.51 (m, 5H), 7.41 (s, 1H), 7.33 (s, 1H), 7.07 (d, J=8.7 Hz, 3H), 4.61 (m, 1H), 3.70 (m, 3H), 3.55 (s, 2H), 3.22 (t, J=10.2 Hz, 2H), 2.80 (d, J=10.5 Hz, 2H), 2.05 (m, 4H), 1.74-1.61 (m, 6H); LCMS (m/z): 646 (MH⁺).

Compound 101: ¹H NMR (DMSO-d₆, 300 MHz): δ 8.47 (s, 3H), 7.68 (d, J=8.1 Hz, 1H), 7.49 (m, 3H), 7.41 (s, 1H), 7.33 (m, 2H), 7.05 (m, 3H), 4.61 (m, 1H), 3.70 (m, 3H), 3.49 (s, 2H), 3.22 (m, 2H), 2.80 (d, J=10.8 Hz, 2H), 2.03 (m, 4H), 1.72-1.59 (m, 6H); LCMS (m/z): 579 (MH⁺)

Compound 102: ¹H NMR (DMSO-d₆, 300 MHz): δ 7.54 (d, J=8.7 Hz, 1H), 7.47 (d, J=8.7 Hz, 2H), 7.29 (d, J=8.7 Hz, 2H), 7.07 (d, J=8.4 Hz, 3H), 4.61 (m, 1H), 4.03 d, J=10.2 Hz, 2H), 3.68 (m, 2H), 3.22 (t, J=10.2 Hz, 2H), 2.98 (s, 3H), 2.02 (br s, 2H), 1.68 (m, 5H), 1.40 (s, 9H); LCMS (m/z): 602 (MH⁺).

Compound 103: ¹H NMR (DMSO-d₆, 300 MHz): δ 8.91 (s, 1H), 7.55 (d, J=9.0 Hz, 1H), 7.48 (d, J=8.1 Hz, 2H), 7.31 (s, 2H), 7.08 (m, 3H), 4.61 (m, 1H), 3.668 (m, 2H), 3.33 (d, J=11.1 Hz, 2H), 3.23 (t, J=9.6 Hz, 2H), 3.01 (br s, 5H), 2.05 (m, 4H), 1.83 (m, 2H), 1.71 (m, 3H); LCMS (m/z): 502 (MH⁺).

Compound 104: ¹H NMR (DMSO-d₆, 300 MHz): δ 8.48 (d, J=4.5 Hz, 2H), 7.53 (d, J=9.0 Hz, 1H), 7.47 (d, J=8.7 Hz, 2H), 7.30 (s, 3H), 7.24 (s, 1H), 7.06 (m, 3H), 4.61 (m, 1H), 3.66 (m, 2H), 3.50 (s, 2H), 3.22 (t, J=10.8 Hz, 2H), 3.01 (m, 2H), 2.86 (d, J=10.5 Hz, 2H), 2.48 (s, 4H), 2.06 (m, 3H), 1.87 (m, 2H), 1.67 (m, 3H); LCMS (m/z): 593 (MH⁺).

Compound 105: ¹H NMR (DMSO-d₆, 300 MHz): δ 8.50 (m, 2H), 7.52 (d, J=9.3 Hz, 2H), 7.47 (d, J=9.0 Hz, 2H), 7.41 (s, 1H), 7.31 (m, 3H), 7.07 (d, J=8.1 Hz, 3H), 4.61 (m, 1H), 3.76 (m, 1H), 3.67 (m, 2H), 3.50 (s, 2H), 3.22 (t, J=9.6 Hz, 2H), 2.80 (d, J=11.1 Hz, 2H), 2.04 (d, J=10.5 Hz, 4H), 1.71 (m, 6H); LCMS (m/z): 579 (MH⁺).

Compound 106: ¹H NMR (DMSO-d₆, 300 MHz): δ 8.89 (m, 2H), 8.45 (d, J=7.8 Hz, 1H), 8.15 (d, J=8.4 Hz, 1H), 7.68 (dd, J=5.1 and 8.2 Hz, 1H), 7.60 (d, J=7.8 Hz, 1H), 7.47 (d, J=9.0 Hz, 2H), 7.42 (s, 1H), 7.25 (s, 1H), 7.07 (d, J=8.7 Hz, 2H), 6.98 (dd, J=1.5 and 8.5 Hz, 1H), 4.70 (m, 1H), 3.78 (m, 1H), 3.68 (d, J=12.0 Hz, 4H), 3.23 (t, J=9.9 Hz, 2H), 2.03 (m, 2H), 1.85 (d, J=10.5 Hz, 2H), 1.65 (m, 6H); LCMS (m/z): 629 (MH⁺).

Compound 107: ¹H NMR (DMSO-d₆, 300 MHz): δ 7.77 (d, J=8.4 Hz, 2H), 7.50 (m, 5H), 7.30 (s, 1H), 7.25 (s, 1H), 7.06 (m, 3H), 4.60 (m, 1H), 3.69 (m, 2H), 3.55 (s, 2H), 3.31 (s, 3H), 3.22 (t, J=10.2 Hz, 2H), 3.02 (m, 2H), 2.85 (d, J=9.9 Hz, 2H), 2.02 (m, 3H), 1.87 (m, 2H), 1.68 (m, 4H); LCMS (m/z): 617 (MH⁺).

Compound 108: ¹H NMR (DMSO-d₆, 300 MHz): δ 8.89 (m, 2H), 8.45 (d, J=7.5 Hz, 1H), 8.15 (d, J=7.8 Hz, 1H), 7.68 (dd, J=5.1 and 8.2 Hz, 1H), 7.59 (m, 2H), 7.42 (s, 1H), 7.24 (s, 1H), 7.16 (d, J=9.0 Hz, 1H), 7.00 (m, 3H), 4.66 (m, 1H), 3.81 (m, 1H), 3.68 (d, J=11.7 Hz, 2H), 3.53 (m, 2H), 3.09 (t, J=9.9 Hz, 2H), 2.05 (m, 3H), 1.85 (d, J=12.6 Hz, 2H), 1.75-1.60 (m, 4H); LCMS (m/z): 645 (MH⁺).

Compound 109: ¹H NMR (DMSO-d₆, 300 MHz): δ 8.45 (m, 2H), 7.68 (d, J=8.1 Hz, 1H), 7.53 (d, J=8.7 Hz, 1H), 7.47 (d, J=8.7 Hz, 2H), 7.30 (m, 3H), 7.06 (m, 3H), 4.60 (m, 1H), 3.67 (m, 2H), 3.49 (s, 2H), 3.31 (s, 3H), 3.22 (m, 4H), 3.01 (m, 2H), 2.88 (d, J=6.9 Hz, 2H), 2.02 (m, 2H), 1.85 (m, 2H), 1.68 (m, 2H); LCMS (m/z): 593 (MH⁺).

Compound 110: ¹H NMR (DMSO-d₆, 300 MHz): δ 7.71 (d, J=7.8 Hz, 2H), 7.64 (d, J=8.4 Hz, 1H), 7.53 (d, J=9.0 Hz, 2H), 7.47 (d, J=9.0 Hz, 2H), 7.30 (d, J=2.1 Hz, 1H), 7.24 (s, 1H), 7.06 (m, 3H), 4.61 (m, 1H), 3.67 (m, 3H), 3.52 (s, 2H), 3.31 (s, 3H), 3.22 (t, J=9.6 Hz, 2H), 3.02 (s, 2H), 2.86 (d, J=9.0 Hz, 2H), 2.02 (m, 3H), 1.87 (m, 2H), 1.68 (m, 4H); LCMS (m/z): 617 (MH⁺).

Compound 111: ¹H NMR (DMSO-d₆, 300 MHz): δ 7.79 (d, J=7.5 Hz, 1H), 7.66 (t, J=7.8 Hz, 1H), 7.56 (d, J=8.1 Hz, 2H), 7.46 (m, 3H), 7.30 (s, 1H), 7.25 (s, 1H), 7.06 (m, 3H), 4.61 (m, 1H), 3.68 (m, 1H), 3.63 (s, 2H), 3.31 (s, 3H), 3.22 (t, J=9.9 Hz, 2H), 2.99 (m, 2H), 2.88 (d, J=9.9 Hz, 2H), 2.13 (m, 2H), 2.04 (m, 2H), 1.81 (m, 2H), 1.67 (m, 4H); LCMS (m/z): 617 (MH⁺).

Compound 112: ¹H NMR (DMSO-d₆, 300 MHz): δ 8.66 (d, J=5.7 Hz, 2H), 8.42 (d, J=7.8 Hz, 1H), 7.62 (d, J=8.4 Hz, 1H), 7.47 (d, J=10.2 Hz, 3H), 7.34 (d, J=6.0 Hz, 2H), 7.26 (s, 1H), 7.07 (d, J=8.7 Hz, 2H), 6.99 (dd, J=2.1 and 8.5 Hz, 1H), 4.71 (m, 1H), 4.44 (d, J=13.2 Hz, 1H), 4.06 (m, 1H), 3.68 (m, 2H), 3.44 (m, 2H), 3.24 (m, 3H), 2.95 (m, 1H), 2.04 (m, 2H), 1.90 (m, 1H), 1.73 (m, 3H), 1.54 (m, 1H); LCMS (m/z): 593 (MH⁺).

Compound 113: ¹H NMR (DMSO-d₆, 300 MHz): δ 8.511 (d, J=8.4 Hz, 1H), 7.77 (d, J=8.1 Hz, 2H), 7.50 (m, 3H), 7.39 (s, 1H), 7.26 (s, 1H), 7.02 (dd, J=2.4 and 8.8 Hz, 1H), 4.38 (m, 1H), 3.93 (d, J=12.0 Hz, 3H), 3.57 (s, 2H), 2.80 (m, 2H), 2.65 (m, 2H), 2.26 (t, J=9.6 Hz, 3H), 1.93 (m, 2H), 1.72 (m, 4H), 1.46 (m, 1H), 1.40 (s, 9H); LCMS (m/z): 559 (MH⁺).

Compound 114: ¹H NMR (DMSO-d₆, 300 MHz): δ 8.49 (d, J=7.8 Hz, 1H), 7.77 (d, J=8.4 Hz, 2H), 7.49 (m, 3H), 7.39 (s, 1H), 7.28 (m, 6H), 7.02 (dd, J=2.1 and 8.8 Hz, 1H), 4.38 (m, 1H), 3.73 (m, 1H), 3.57 (s, 2H), 3.44 (s, 2H), 2.80 (d, J=10.2 Hz, 2H), 2.64 (m, 2H), 2.25 (t, J=9.3 Hz, 2H), 1.95 (m, 4H), 1.66 (m, 6H); LCMS (m/z): 549 (MH⁺).

Compound 115: ¹H NMR (DMSO-d₆, 300 MHz): δ 8.66 (d, J=4.5 Hz, 2H), 8.57 (d, J=7.8 Hz, 1H), 7.49 (m, 4H), 7.35 (m, 3H), 7.07 (d, J=8.4 Hz, 1H), 4.61 (m, 1H), 4.45 (d, J=13.5 Hz, 1H), 4.08 (m, 1H), 3.65 (m, 1H), 3.45 (d, J=12.9 Hz, 1H), 3.22 (t, J=11.4 Hz, 3H), 2.94 (m, 1H), 2.02 (m, 2H), 1.90 (d, J=11.7 Hz, 1H), 1.79-1.49 (m, 6H); LCMS (m/z): 593 (MH⁺)

Compound 116: ¹H NMR (DMSO-d₆, 300 MHz): δ 8.63 (s, 1H), 8.52 (s, 1H), 7.92 (s, 1H), 7.81 (d, J=7.8 Hz, 2H), 7.49 (d, J=9.0 Hz, 2H), 7.30 (m, 8H), 7.02 (d, J=7.8 Hz, 1H), 4.37 (m, 1H), 4.77 (m, 1H), 3.53 (s, 2H), 3.45 (s, 2H), 3.12 (m, 1H), 2.81 (br s, 1H), 2.67 (br s, 2H), 2.25 (br s, 2H), 1.94 (m, 4H), 1.66 (m, 6H); LCMS (m/z): 567 (MH⁺).

Compound 117: ¹H NMR (DMSO-d₆, 300 MHz): δ 8.46 (d, J=4.2 Hz, 1H), 7.74 (t, J=7.5 Hz, 1H), 7.47 (m, 4H), 7.25 (m, 3H), 7.06 (m, 3H), 4.61 (m, 1H), 3.68 (m, 2H), 3.58 (s, 2H), 3.31 (s, 3H), 3.21 (t, J=9.3 Hz, 2H), 3.04 (br s, 1H), 2.91 (d, J=10.5 Hz, 2H), 2.08 (m, 4H), 1.87 (m, 2H), 1.68 (m, 4H); LCMS (m/z): 593 (MH⁺).

Compound 118: ¹H NMR (DMSO-d₆, 300 MHz): δ 8.65 (d, J=5.7 Hz, 2H), 7.54 (d, J=8.4 Hz, 1H), 7.47 (d, J=8.7 Hz, 2H), 7.42 (d, J=5.7 Hz, 2H), 7.49 (d, J=8.4 Hz, 4H), 7.30 (d, J=2.7 Hz, 2H), 7.06 (m, 3H), 4.61 (m, 2H), 3.68 (m, 2H), 3.47 (m, 1H), 3.28 (s, 3H), 3.22 (t, J=10.5 Hz, 2H), 3.05 (m, 2H), 2.88 (m, 1H), 2.02 (m, 4H), 1.81 (m, 2H), 1.70 (m, 4H); LCMS (m/z): 607 (MH⁺).

Compound 119: ¹H NMR (DMSO-d₆, 300 MHz): δ 7.67 (d, J=7.8 Hz, 2H), 7.52 (m, 5H), 7.30 (d, J=2.4 Hz, 1H), 7.25 (s, 1H), 7.06 (m, 3H), 4.61 (m, 1H), 3.68 (m, 2H), 3.55 (s, 2H), 3.29 (s, 3H), 3.22 (t, J=9.3 Hz, 2H), 3.00 (s, 2H), 2.87 (d, J=9.9 Hz, 2H), 2.02 (m, 3H), 1.87 (m, 2H), 1.69 (m, 4H); LCMS (m/z): 660 (MH⁺).

Compound 120: ¹H NMR (DMSO-d₆, 300 MHz): δ 8.81 (d, J=6.9 Hz, 1H), 7.49 (m, 4H), 7.34 (s, 1H), 7.07 (d, J=8.7 Hz, 3H), 4.62 (m, 1H), 4.41 (m, 1H), 3.65 (m, 2H), 3.52 (m, 2H), 3.37 (m, 1H), 3.22 (t, J=9.0 Hz, 4H), 2.06 (m, 3H), 1.93 (m, 1H), 1.70 (m, 2H), 1.39 (s, 9H); LCMS (m/z): 574 (MH⁺).

Compound 121: ¹H NMR (DMSO-d$_6$, 300 MHz): δ 9.14 (s, 2H), 9.00 (d, J=6.9 Hz, 1H), 7.54 (t, J=4.8 Hz, 2H), 7.48 (d, J=9.0 Hz, 2H), 7.36 (d, J=2.7 Hz, 1H), 7.09 (d, J=7.5 Hz, 2H), 4.62 (m, 1H), 4.58 (m, 1H), 3.48 (m, 2H), 3.37 (m, 2H), 3.22 (m, 4H), 2.18 (m, 1H), 2.02 (m, 3H), 1.70 (m, 2H); LCMS (m/z): 474 (MH$^+$).

Compound 122: ¹H NMR (DMSO-d$_6$, 300 MHz): δ 8.71 (d, J=7.5 Hz, 1H), 8.48 (s, 2H), 7.49 (m, 4H), 7.34 (t, J=5.7 Hz, 3H), 7.07 (dd, J=2.4 and 8.8 Hz, 3H), 4.62 (m, 1H), 4.38 (m, 1H), 3.70 (m, 1H), 3.63 (s, 2H), 3.24 (m, 3H), 2.81 (m, 1H), 2.64 (m, 1H), 2.15 (m, 1H), 2.02 (m, 3H), 1.88 (m, 1H), 1.70 (m, 3H); LCMS (m/z): 565 (MH$^+$).

Compound 123: ¹H NMR (DMSO-d$_6$, 300 MHz): δ 8.71 (d, J=7.5 Hz, 1H), 8.48 (s, 2H), 7.49 (m, 4H), 7.34 (t, J=5.7 Hz, 3H), 7.07 (dd, J=2.4 and 8.8 Hz, 3H), 4.62 (m, 1H), 4.38 (m, 1H), 3.70 (m, 1H), 3.63 (s, 2H), 3.24 (m, 3H), 2.81 (m, 1H), 2.64 (m, 1H), 2.15 (m, 1H), 2.02 (m, 3H), 1.88 (m, 1H), 1.70 (m, 3H); LCMS (m/z): 565 (MH$^+$).

Compound 124: ¹H NMR (DMSO-d$_6$, 300 MHz): δ 8.85 (s, 1H), 8.68 (d, J=6.6 Hz, 1H), 8.46 (d, J=2.4 Hz, 1H), 7.74 (m, 1H), 7.46 (m, 4H), 7.34 (d, J=2.7 Hz, 1H), 7.23 (t, J=5.4 Hz, 1H), 7.34 (m, 2H), 7.07 (d, J=9.0 Hz, 3H), 4.62 (m, 1H), 4.38 (m, 1H), 3.72 (s, 2H), 3.65 (m, 1H), 3.22 (t, J=10.5 Hz, 4H), 2.85 (m, 1H), 2.69 (m, 1H), 2.55 (m, 1H), 2.15 (m, 1H), 2.02 (m, 2H), 1.83 (m, 1H), 1.70 (m, 2H); LCMS (m/z): 565 (MH$^+$).

Compound 125: ¹H NMR (DMSO-d$_6$, 300 MHz): δ 8.89 (m, 1H), 8.65 (m, 2H), 7.47 (m, 6H), 7.35 (dd, J=2.4 and 8.1 Hz, 1H), 7.07 (m, 3H), 4.61 (m, 1H), 4.42 (m, 1H), 3.66 (m, 3H), 3.52 (m, 2H), 3.22 (t, J=10.2 Hz, 3H), 2.16 (m, 1H), 2.02 (m, 3H), 1.70 (m, 2H); LCMS (m/z): 579 (MH$^+$).

Compound 126: ¹H NMR (DMSO-d$_6$, 300 MHz): δ 8.93 (d, J=1.8 Hz, 1H), 8.68 (dd, J=1.5 and 4.8 Hz, 1H), 8.61 (d, J=6.0 Hz, 1H), 8.18 (m, 1H), 7.56 (m, 2H), 7.47 (d, J=9.0 Hz, 2H), 7.35 (m, 2H), 7.07 (m, 3H), 4.61 (m, 1H), 4.27 (q, J=6.3 Hz, 1H), 3.68 (m, 2H), 3.46 (m, 2H), 3.23 (m, 4H), 2.03 (m, 3H), 1.91 (m, 1H), 1.70 (m, 2H); LCMS (m/z): 615 (MH$^+$).

Compound 127: ¹H NMR (DMSO-d$_6$, 300 MHz): δ 8.78 (d, J=6.6 Hz, 1H), 7.50 (d, J=9.0 Hz, 1H), 7.43 (s, 1H), 7.34 (m, 5H), 7.02 (dd, J=2.7 and 8.8 Hz, 1H), 4.38 (m, 2H), 3.52 (m, 1H), 3.47 (s, 2H), 3.39 (m, 1H), 2.21 (m, 2H), 2.64 (m, 2H), 2.23 (t, J=11.1 Hz, 2H), 2.06 (m, 1H), 1.92 (m, 3H), 1.63 (m, 2H), 1.39 (s, 9H); LCMS (m/z): 554 (MH$^+$).

Compound 128: ¹H NMR (DMSO-d$_6$, 300 MHz): δ 9.19 (br s, 2H), 9.02 (d, J=6.6 Hz, 1H), 7.65 (t, J=9.0 Hz, 2H), 7.55 (m, 3H), 7.36 (dd, J=2.4 and 9.3 Hz, 1H), 7.15-7.04 (m, 1H), 4.74 (s, 1H), 4.54 (m, 2H), 4.34 (m, 2H), 3.67 (m, 1H), 3.19 (d, J=5.7 Hz, 4H), 3.01 (t, J=11.4 Hz, 2H), 2.18 (m, 3H), 2.02 (m, 3H); LCMS (m/z): 454 (MH$^+$).

Compound 129: ¹H NMR (DMSO-d$_6$, 300 MHz): δ 8.67 (d, J=6.9 Hz, 1H), 8.46 (s, 2H), 7.49 (d, J=8.7 Hz, 1H), 7.41 (s, 1H), 7.32 (m, 6H), 7.01 (d, J=8.7 Hz, 2H), 4.37 (m, 2H), 3.62 (s, 2H), 3.47 (s, 2H), 2.80 (t, J=7.8 Hz, 1H), 2.64 (d, J=5.4 Hz, 3H), 2.22 (t, J=9.9 Hz, 4H), 1.92 (m, 4H), 1.65 (m, 2H); LCMS (m/z): 545 (MH$^+$).

Compound 130: ¹H NMR (DMSO-d$_6$, 300 MHz): δ 8.67 (d, J=7.2 Hz, 1H), 8.49 (s, 1H), 7.43 (d, J=3.0 Hz, 1H), 7.70 (d, J=7.8 Hz, 1H), 7.49 (d, J=8.7 Hz, 1H), 7.33 (m, 6H), 7.01 (dd, J=2.1 and 9.1 Hz, 1H), 4.36 (m, 2H), 3.61 (s, 2H), 3.47 (s, 2H), 2.77 (t, J=7.2 Hz, 1H), 2.63 (m, 2H), 2.46 (m, 3H), 2.19 (m, 3H), 1.91 (m, 2H), 1.82 (m, 1H), 1.64 (m, 2H); LCMS (m/z): 545 (MH$^+$).

Compound 131: LCMS (m/z): 568 (MH$^+$).

(c) Assay Data

Compounds 61-131 of Table 1 were assayed for their ability to activate AMPK using an enzyme-linked immunosorbent assay. The EC$_{50}$ values for AMPK activation for compounds 61-131 are presented in Table 4 below, in which "A" is less than 0.1 μM; "B" is 0.1-0.5 μM; "C" is 0.5-1 μM; "D" is 1-10 μM; "E" is 10-50 μM and "F" is >50 μM.

TABLE 4

| Cpd No. | AMPK EC$_{50}$ |
|---|---|
| 61 | B |
| 62 | E |
| 63 | A |
| 64 | A |
| 65 | A |
| 66 | A |
| 67 | A |
| 68 | A |
| 69 | A |
| 70 | A |
| 71 | A |
| 72 | B |
| 73 | C |
| 74 | B |
| 75 | A |
| 76 | B |
| 77 | B |
| 78 | A |
| 79 | B |
| 80 | A |
| 81 | B |
| 82 | B |
| 83 | B |
| 84 | E |
| 85 | C |
| 86 | F |
| 87 | A |
| 88 | A |
| 89 | A |
| 90 | A |
| 91 | F |
| 92 | C |
| 93 | B |
| 94 | A |
| 95 | A |
| 96 | A |
| 97 | A |
| 98 | A |
| 99 | A |
| 100 | A |
| 101 | A |
| 102 | D |
| 103 | D |
| 104 | B |
| 105 | A |
| 106 | B |
| 107 | A |
| 108 | B |
| 109 | A |
| 110 | A |
| 111 | B |
| 112 | A |
| 113 | B |
| 114 | B |
| 115 | A |
| 116 | B |
| 117 | A |
| 118 | B |
| 119 | A |
| 120 | D |
| 121 | F |
| 122 | B |
| 123 | B |
| 124 | D |
| 125 | D |
| 126 | D |
| 127 | D |
| 128 | F |
| 129 | D |
| 130 | D |
| 131 | D |

145

Example 4

(a) Analytical Data

The following compounds were prepared using methods analogous to those described in Example 3(a) and in Scheme 4.

Compound 137: N-(1-(pyridin-4-ylmethyl)piperidin-4-yl)-5-(1-(4-(trifluoromethoxy)phenyl)piperidin-4-yloxy)benzo[b]thiophene-2-carboxamide. $^1$H NMR (DMSO-$d_6$, 300 MHz): δ 8.56 (m, 3H), 8.04 (s, 1H), 7.92 (d, J=8.4 Hz, 1H), 7.56 (s, 1H), 7.37 (d, J=4.5 Hz, 2H), 7.21 (t, J=8.4 Hz, 3H), 7.08 (d, J=9.0 Hz, 2H), 4.72 (m, 1H), 3.80 (m, 1H), 3.59 (m, 2H), 3.57 (s, 2H), 3.17 (t, J=9.6 Hz, 2H), 2.89 (d, J=11.4 Hz, 2H), 2.13 (t, J=9.9 Hz, 4H), 1.85 (m, 4H), 1.69 (m, 2H); LCMS (m/z): 611 (MH$^+$).

Compound 138: N-(1-(pyridin-4-ylmethyl)piperidin-4-yl)-5-(1-(4-(trifluoromethyl)phenyl)piperidin-4-yloxy)benzo[b]thiophene-2-carboxamide. $^1$H NMR (DMSO-$d_6$, 300 MHz): δ 8.50 (m, 3H), 7.97 (s, 1H), 7.86 (d, J=9.0 Hz, 1H), 7.48 (d, J=8.4 Hz, 3H), 7.30 (d, J=5.4 Hz, 2H), 7.13 (d, J=10.8 Hz, 1H), 7.08 (d, J=8.4 Hz, 2H), 4.69 (m, 1H), 3.67 (m, 3H), 3.50 (s, 2H), 3.24 (t, J=9.3 Hz, 2H), 2.80 (d, J=11.7 Hz, 2H), 2.06 (t, J=9.9 Hz, 4H), 1.83-1.59 (m, 6H); LCMS (m/z): 595 (MH$^+$).

Compound 139: N-(1-(pyridin-4-ylmethyl)piperidin-4-yl)-5-(1-(4-chlorophenyl)piperidin-4-yloxy)benzo[b]thiophene-2-carboxamide formate salt. $^1$H NMR (DMSO-$d_6$, 300 MHz): δ 8.50 (m, 3H), 8.13 (s, 1H), 7.95 (s, 1H), 7.83 (d, J=8.7 Hz, 1H), 7.21 (d, J=1.8 Hz, 1H), 7.33 (m, 5H), 7.07 (dd, J=2.1 and 9.0 Hz, 1H), 4.45 (m, 1H), 3.72 (m, 1H), 3.50 (s, 2H), 3.48 (s, 2H), 2.80 (d, J=9.9 Hz, 2H), 2.67 (m, 2H), 2.25 (t, J=9.3 Hz, 2H), 2.07 (t, J=10.8 Hz, 2H), 1.94 (m, 2H), 1.80 (m, 2H), 1.63 (m, 4H); LCMS (m/z): 575 (MH$^+$).

Compound 140: $^1$H NMR (DMSO-$d_6$, 300 MHz): δ 8.85 (s, 1H), 8.43 (d, J=8.1 Hz, 1H), 7.98 (s, 1H), 7.79 (d, J=9.0 Hz, 1H), 7.66 (s, 1H), 7.47 (d, J=9.0 Hz, 2H), 7.06 (m, 3H), 4.75 (m, 2H), 3.93 (m, 3H), 3.69 (m, 2H), 3.22 (t, J=9.3 Hz, 2H), 2.83 (m, 2H), 2.05 (m, 2H), 1.77 (m, 4H), 1.41 (s, 9H); LCMS (m/z): 604 (MH$^+$).

Compound 141: $^1$H NMR (DMSO-$d_6$, 300 MHz): δ 8.85 (s, 1H), 8.79 (br s, 1H), 7.68 (d, J=7.2 Hz, 1H), 8.07 (s, 1H), 7.79 (d, J=8.7 Hz, 1H), 7.66 (s, 1H), 7.48 (d, J=8.4 Hz, 2H), 7.07 (m, 3H), 4.74 (m, 1H), 4.21 (s, 4H), 4.01 (s, 2H), 3.79 (s, 2H), 3.68 (m, 2H), 3.27 (m, 2H), 3.01 (m, 2H), 1.98 (m, 2H), 1.75 (m, 2H); LCMS (m/z): 504 (MH$^+$).

Compound 142: $^1$H NMR (DMSO-$d_6$, 300 MHz): δ 8.49 (d, J=4.8 Hz, 2H), 8.43 (d, J=7.5 Hz, 1H), 7.99 (s, 1H), 7.78 (d, J=8.7 Hz, 1H), 7.65 (s, 1H), 7.47 (d, J=9.0 Hz, 2H), 7.30 ((d, J=4.8 Hz, 2H), 7.06 (t, J=8.4 Hz, 3H), 4.72 (m, 1H), 3.69 (m, 3H), 3.50 (s, 2H), 3.22 (t, J=9.6 Hz, 2H), 2.80 (d, J=11.1 Hz, 2H), 2.06 (t, J=9.6 Hz, 4H), 1.82-1.58 (m, 6H); LCMS (m/z): 595 (MH$^+$).

Compound 143: $^1$H NMR (CDCl$_3$, 300 MHz): δ 8.46 (d, J=4.8 Hz, 1H), 8.42 (d, J=7.8 Hz, 1H), 7.99 (s, 1H), 7.75 (m, 2H), 7.65 (d, J=1.5 Hz, 1H), 7.47 (d, J=9.0 Hz, 2H), 7.41 (d, J=7.2 Hz, 1H), 7.24 (t, J=6.9 Hz, 1H), 7.07 (d, J=8.7 Hz, 2H), 7.03 (d, J=2.1 Hz, 1H), 4.72 (m, 1H), 4.71 (m, 2H), 3.58 (s, 2H), 3.22 (t, J=9.6 Hz, 3H), 2.84 (d, J=11.4 Hz, 2H), 2.10 (m, 4H), 1.81-1.54 (s, 6H); LCMS (m/z): 595 (MH$^+$).

Compound 144: $^1$H NMR (DMSO-$d_6$, 300 MHz): δ 8.41 (d, J=8.1 Hz, 1H), 7.99 (s, 1H), 7.78 (d, J=8.1 Hz, 3H), 7.64 (s, 1H), 7.49 (d, J=8.4 Hz, 4H), 7.06 (m, 3H), 4.75 (m, 1H), 3.69 (m, 1H), 3.56 (s, 2H), 3.23 (t, J=9.6 Hz, 2H), 2.79 (d, J=11.4 Hz, 2H), 2.06 (m, 4H), 1.78 (m, 2H), 1.65 (m, 4H); LCMS (m/z): 619 (MH$^+$).

Compound 145: $^1$H NMR (DMSO-$d_6$, 300 MHz): δ 8.40 (d, J=7.5 Hz, 1H), 7.99 (s, 1H), 7.78 (d, J=8.7 Hz, 1H), 7.72 (m, 2H), 7.65 (d, J=2.1 Hz, 2H), 7.54 (d, J=7.8 Hz, 1H), 7.47 (d, J=9.0 Hz, 2H), 7.06 (m, 3H), 4.72 (m, 1H), 3.69 (m, 3H), 3.53 (s, 2H), 3.23 (t, J=9.6 Hz, 2H), 2.80 (d, J=10.5 Hz, 2H), 2.06 (m, 4H), 1.78-1.57 (m, 6H); LCMS (m/z): 619 (MH$^+$).

Compound 146: $^1$H NMR (DMSO-$d_6$, 300 MHz): δ 8.41 (d, J=8.4 Hz, 1H), 7.99 (s, 1H), 7.79 (t, J=4.5 Hz, 2H), 7.66 (m, 2H), 7.55 (d, J=7.5 Hz, 1H), 7.46 (m, 3H), 7.06 (t, J=8.7 Hz, 3H), 4.73 (m, 1H), 3.69 (m, 2H), 3.64 (s, 2H), 3.22 (m, 3H), 2.81 (d, J=10.5 Hz, 2H), 2.11 (m, 4H), 1.81-1.57 (m, 6H); LCMS (m/z): 619 (MH$^+$).

Compound 147: $^1$H NMR (DMSO-$d_6$, 300 MHz): δ 8.18 (d, J=7.8 Hz, 1H), 7.73 (d, J=9.6 Hz, 2H), 7.47 (d, J=9.0 Hz, 2H), 7.19 (d, J=2.1 and 8.7 Hz, 1H), 7.08 (d, J=8.7 Hz, 2H), 4.74 (m, 1H), 3.89 (d, J=12.6 Hz, 3H), 3.67 (m, 2H), 3.23 (t, J=10.5 Hz, 3H), 2.89 (s, 2H), 2.06 (m, 2H), 1.82-1.70 (m, 4H), 1.48 (m, 1H), 1.40 (s, 9H); LCMS (m/z): 638 (MH$^+$).

Compound 148: $^1$H NMR (DMSO-$d_6$, 300 MHz): δ 8.84 (s, 1H), 8.70 (s, 1H), 8.47 (d, J=6.9 Hz, 1H), 7.76 (m, 1H), 7.48 (d, J=8.7 Hz, 2H), 7.20 (d, J=9.0 Hz, 1H), 7.09 (d, J=9.0 Hz, 2H), 4.88 (m, 3H), 4.74 (m, 2H), 3.03 (m, 1H), 3.68 (m, 2H), 3.25 (m, 3H), 3.01 (m, 1H), 2.02 (m, 3H), 1.77 (m, 3H); LCMS (m/z): 538 (MH$^+$).

Compound 149: $^1$H NMR (DMSO-$d_6$, 300 MHz): δ 8.51 (d, J=7.5 Hz, 1H), 7.96 (s, 1H), 7.86 (d, J=9.0 Hz, 1H), 7.47 (d, J=8.4 Hz, 3H), 7.13 (dd, J=2.4 and 9.1 Hz, 1H), 7.07 (d, J=8.7 Hz, 2H), 4.69 (m, 1H), 3.93 (d, J=11.4 Hz, 3H), 3.65 (s, 2H), 3.24 (m, 2H), 2.84 (m, 3H), 2.03 (m, 2H), 1.77 (m, 4H), 1.47 (m, 1H), 1.41 (s, 9H); LCMS (m/z): 604 (MH$^+$).

Compound 150: $^1$H NMR (DMSO-$d_6$, 300 MHz): δ 8.79 (d, J=7.5 Hz, 3H), 8.06 (s, 1H), 7.87 (d, J=9.0 Hz, 1H), 7.49 (m, 2H), 7.14 (dd, J=2.4 and 8.4 Hz, 1H), 7.09 (d, J=9.3 Hz, 2H), 4.02 (m, 1H), 3.66 (m, 3H), 3.46 (m, 1H), 3.28 (m, 3H), 3.00 (m, 2H), 2.03 (m, 4H), 1.75 (m, 4H); LCMS (m/z): 504 (MH$^+$).

Compound 151: $^1$H NMR (DMSO-$d_6$, 300 MHz): δ 8.48 (d, J=5.4 Hz, 2H), 8.15 (d, J=7.8 Hz, 3H), 7.75 (d, J=2.1 Hz, 1H), 7.72 (s, 1H), 7.48 (d, J=9.0 Hz, 2H), 7.30 (d, J=5.7 Hz, 2H), 7.18 (dd, J=1.8 and 8.8 Hz, 1H), 7.08 (d, J=8.7 Hz, 2H), 4.74 (m, 1H), 3.70 (m, 3H), 3.50 (s, 2H), 3.22 (t, J=9.9 Hz, 2H), 2.76 (d, J=11.7 Hz, 2H), 2.10 (m, 4H), 1.81 (m, 2H), 1.65 (m, 4H); LCMS (m/z): 629 (MH$^+$).

Compound 152: $^1$H NMR (DMSO-$d_6$, 300 MHz): δ 8.45 (t, J=4.8 Hz, 2H), 8.14 (d, J=7.2 Hz, 1H), 7.71 (m, 3H), 7.48 (d, J=8.4 Hz, 2H), 7.34 (t, J=6.6 Hz, 1H), 7.18 (d, J=9.3 Hz, 1H), 7.08 (d, J=8.7 Hz, 2H), 4.73 (m, 1H), 3.70 (m, 3H), 3.49 (s, 2H), 3.22 (t, J=9.6 Hz, 2H), 2.76 (d, J=10.5 Hz, 2H), 2.07 (m, 4H), 1.79 (m, 2H), 1.72-1.59 (m, 4H); LCMS (m/z): 629 (MH$^+$)

Compound 153: $^1$H NMR (DMSO-$d_6$, 300 MHz): δ 8.46 (d, J=4.5 Hz, 1H), 8.15 (d, J=7.8 Hz, 3H), 7.75 (m, 3H), 7.48 (d, J=9.0 Hz, 2H), 7.41 (d, J=7.5 Hz, 1H), 7.22 (m, 2H), 7.08 (d, J=8.4 Hz, 2H), 4.74 (m, 1H), 3.70 (m, 3H), 3.58 (s, 2H), 3.22 (t, J=9.3 Hz, 2H), 2.80 (d, J=10.8 Hz, 2H), 2.11 (m, 4H), 1.84-1.58 (m, 6H); LCMS (m/z): 629 (MH$^+$).

Compound 154: $^1$H NMR (DMSO-$d_6$, 300 MHz): δ 8.14 (d, J=7.8 Hz, 1H), 7.76 (m, 4H), 7.48 (t, J=6.7 Hz, 4H), 7.18 (d, J=8.7 Hz, 1H), 7.08 (d, J=8.4 Hz, 2H), 4.74 (m, 1H), 3.70 (m, 3H), 3.55 (s, 2H), 3.22 (t, J=9.0 Hz, 2H), 2.73 (m, 2H), 2.10 (m, 4H), 1.80 (m, 2H), 1.65 (m, 4H); LCMS (m/z): 653 (MH$^+$).

Compound 155: $^1$H NMR (DMSO-$d_6$, 300 MHz): δ 8.66 (d, J=3.6 Hz, 2H), 8.22 (d, J=7.2 Hz, 1H), 7.74 (d, J=9.9 Hz, 2H), 7.48 (d, J=8.7 Hz, 2H), 7.36 (d, J=4.8 Hz, 2H), 7.19 (d, J=8.7 Hz, 1H), 7.08 (d, J=8.4 Hz, 2H), 4.74 (m, 1H), 4.36 (d, J=12.6 Hz, 2H), 4.07 (m, 1H), 3.70 (m, 2H), 3.45 (d, J=14.1

Hz, 1H), 3.22 (m, 3H), 3.04 (t, J=10.8 Hz, 1H), 2.06 (m, 2H), 1.95 (m, 1H), 1.80-1.52 (m, 5H); LCMS (m/z): 643 (MH+).

(b) Assay Data

Compounds 137-141 and 143-155 of Table 1 were assayed for their ability to activate AMPK using an enzyme-linked immunosorbent assay. The $EC_{50}$ values for AMPK activation for compounds 137-141 and 143-155 are presented in Table 5 below, in which "A" is less than 0.1 µM; "B" is 0.1-0.5 µM; "C" is 0.5-1 µM; "D" is 1-50 µM and "F" is >50 µM:

TABLE 5

| Cpd No. | AMPK $EC_{50}$ |
|---|---|
| 137 | A |
| 138 | A |
| 139 | A |
| 140 | C |
| 141 | B |
| 144 | A |
| 145 | B |
| 146 | B |
| 147 | D |
| 148 | F |
| 149 | A |
| 150 | D |
| 151 | A |
| 152 | A |
| 153 | B |
| 154 | A |
| 155 | A |

Example 5

(a) Synthetic Example 1-(4-fluorobenzyl)-N-(5-(1-(4-(trifluoromethyl)phenyl)piperidin-4-yloxy)-2,3-dihydro-1H-inden-1-yl)piperidin-4-amine (compound 159)

Step 1. 5-(1-(4-(trifluoromethyl)phenyl)piperidin-4-yloxy)-2,3-dihydro-1H-inden-1-one To a stirred solution of 5-hydroxy-2,3-dihydro-1H-inden-1-one (0.74 g, 5.0 mmol) in toluene (30 mL) at room temperature was added diisopropyl azodicarboxylate (1.21 g, 6.0 mmol), 1-(4-trifluoromethylphenyl)piperidin-4-ol (1.47 g, 6.0 mmol), and triphenyl phosphine (1.57 g, 6.0 mmol). The mixture was stirred at 60° C. overnight and then concentrated under reduced pressure. The residue obtained was purified by flash chromatography (silica gel, ethyl acetate/hexanes=1/1) to afford the title compound as a pale yellow solid (1.49 g, 79%). ¹H-NMR (CDCl₃, 300 MHz): δ 7.70 (m, 1H), 7.49 (m, 2H), 6.93 (m, 4H), 4.65 (m, 1H), 3.59 (m, 2H), 3.30 (m, 2H), 3.09 (m, 2H), 2.68 (m, 2H), 2.12 (m, 2H), 1.96 (m, 2H) ppm; MS (ESI): 376.6 (M+1).

Step 2. tert-butyl 4-(5-(1-(4-(trifluoromethyl)phenyl)piperidin-4-yloxy)-2,3-dihydro-1H-inden-1-ylamino)piperidine-1-carboxylate Tert-butyl 4-aminopiperidine-1-carboxylate (0.48 g, 2.4 mmol) and 5-(1-(4-(trifluoromethyl)phenyl)piperidin-4-yloxy)-2,3-dihydro-1H-inden-1-one (0.75 g, 2.0 mmol) were mixed in neat titanium(IV) isopropoxide (2.85 g, 10.0 mmol) and stirred at room temperature overnight. Methanol (10 mL) was added followed by addition of sodium borohydride (0.12 g, 3.2 mmol). The reaction was stirred at room temperature for 3 h and then quenched by adding 0.1N aqueous sodium hydroxide. The resulting mixture was filtered through celite, and the residue was washed with ethyl acetate (2×10 mL) and with dichloromethane (10 mL). The organic layer was separated and dried over sodium sulfate. The drying agent was filtered off, and the filtrate concentrated under reduced pressure. The residue obtained was purified by flash chromatography (silica gel, ethyl acetate/hexanes=1/4) to afford the title compound as a off-white solid (0.73 g, 65%). ¹H NMR (CDCl₃, 300 MHz) 7.64 (m, 1H), 7.48 (m, 2H), 6.95 (m, 2H), 6.76 (m, 2H), 4.68 (m, 1H), 4.44 (m, 1H), 3.53 (m, 2H), 3.18 (m, 2H), 2.85 (m, 4H), 2.47 (m, 2H), 2.24-1.79 (m, 12H), 1.46 (s, 9H) ppm; MS (ES) 560.6 (M+H).

Step 3. N-(5-(1-(4-(trifluoromethyl)phenyl)piperidin-4-yloxy)-2,3-dihydro-1H-inden-1-yl)piperidin-4-amine A mixture of tert-butyl 4-(5-(1-(4-(trifluoromethyl)phenyl)piperidin-4-yloxy)-2,3-dihydro-1H-inden-1-ylamino)piperidine-1-carboxylate (0.73 g, 1.3 mmol) and 4N hydrochloric acid in dioxane (4 mL) was stirred at room temperature for 1 h. The reaction mixture was concentrated and washed with diethyl ether (2×5 mL) and then dried under reduced pressure to afford the title compound (as the 3.HCl salt) as a off-white solid (0.57 g, 97%). ¹H NMR (CD₃OD, 300 MHz) 7.73 (m, 2H), 7.58 (m, 3H), 7.07 (s, 1H), 7.01 (m, 1H), 4.93 (m, 1H), 4.78 (m, 1H), 3.65 (m, 6H), 3.20 (m, 5H), 2.62 (m, 1H), 2.35 (m, 6H), 2.08 (m, 5H) ppm; MS (ES) 460.7 (M+H)

Step 4. 1-(4-fluorobenzyl)-N-(5-(1-(4-(trifluoromethyl)phenyl)piperidin-4-yloxy)-2,3-dihydro-1H-inden-1-yl)piperidin-4-amine To a stirred mixture of N-(5-(1-(4-(trifluoromethyl)phenyl)piperidin-4-yloxy)-2,3-dihydro-1H-inden-1-yl)piperidin-4-amine.3HCl (0.06 g, 0.1 mmol) in anhydrous dimethylformamide (0.5 mL) at room temperature was added 1-bromomethyl-4-fluorobenzene (0.02 g, 0.1 mmol) and N,N-diisopropylethylamine (0.07 g, 0.5 mmol). The resulting mixture was stirred at room temperature overnight. After this time the mixture was concentrated under reduced pressure and the resulting residue was purified by flash chromatography (silica gel, methylene chloride/methanol/30% ammonium hydroxide=20/1/0.05) to afford the title compound as a off-white solid (0.05 g, 88%). ¹H NMR (CDCl₃, 300 MHz) 7.46 (m, 2H), 7.25 (m, 3H), 6.96 (m, 4H), 6.75 (m, 2H), 4.47 (m, 1H), 4.29 (m, 1H), 3.58 (m, 2H), 3.48 (s, 2H), 3.06-2.54 (m, 6H), 2.38 (m, 1H), 2.14-1.74 (m, 9H), 1.49 (m, 2H) ppm; MS (ES) 568.6 (M+H).

(b) Analytical Data

The following compounds were prepared using methods analogous to those described in Example 5(a) and in Scheme 5.

Compound 156: ¹H NMR (CDCl₃, 300 MHz) δ 7.64 (m, 1H), 7.48 (m, 2H), 6.95 (m, 2H), 6.76 (m, 2H), 4.68 (m, 1H), 4.44 (m, 1H), 3.53 (m, 2H), 3.18 (m, 2H), 2.85 (m, 4H), 2.47 (m, 2H), 2.24-1.79 (m, 12H), 1.46 (s, 9H) ppm; MS (ES) 558.6 (M+H).

Compound 157: ¹H NMR (CD₃OD, 300 MHz) δ 7.73 (m, 2H), 7.58 (m, 3H), 7.07 (s, 1H), 7.01 (m, 1H), 4.93 (m, 1H), 4.78 (m, 1H), 3.65 (m, 6H), 3.20 (m, 5H), 2.62 (m, 1H), 2.35 (m, 6H), 2.08 (m, 5H) ppm; MS (ES) 460.7 (M+H).

Compound 158: $^1$H NMR (CDCl$_3$, 300 MHz) δ 8.53 (m, 2H), 7.62 (m, 1H), 7.46 (m, 2H), 7.28 (m, 2H), 6.91 (m, 2H), 6.78 (m, 2H), 4.68 (m, 1H), 4.43 (m, 1H), 3.52 (m, 4H), 3.17 (m, 2H), 2.84 (m, 4H), 2.46 (m, 2H), 2.22-1.76 (m, 12H) ppm; MS (ES) 551.6 (M+H).

Compound 159: $^1$H NMR (CDCl$_3$, 300 MHz) δ 7.46 (m, 2H), 7.25 (m, 3H), 6.96 (m, 4H), 6.75 (m, 2H), 4.47 (m, 1H), 4.29 (m, 1H), 3.58 (m, 2H), 3.48 (s, 2H), 3.06-2.54 (m, 6H), 2.38 (m, 1H), 2.14-1.74 (m, 9H), 1.49 (m, 2H) ppm; MS (ES) 568.6 (M+H).

Compound 160: $^1$H NMR (CDCl$_3$, 300 MHz) δ 7.60 (m, 2H), 7.45 (m, 4H), 7.22 (m, 1H), 6.93 (m, 2H), 6.76 (m, 2H), 4.47 (m, 1H), 4.30 (m, 1H), 3.58 (m, 4H), 3.23 (m, 2H), 2.99 (m, 1H), 2.79 (m, 6H), 2.39 (m, 1H), 2.16-1.73 (m, 9H), 1.51 (m, 2H) ppm; MS (ES) 575.6 (M+H).

(c) Assay Data

Compounds 156-160 of Table 1 were assayed for their ability to activate AMPK using an enzyme-linked immunosorbent assay. The EC$_{50}$ values for AMPK activation for compounds 156-160 are presented in Table 6 below, in which "A" is less than 0.5 μM; "B" is 0.5-1 μM; "C" is 1-100 μM; and "D" is >100 μM:

TABLE 6

| Cpd No. | AMPK EC$_{50}$ |
|---|---|
| 156 | B |
| 157 | D |
| 158 | B |
| 159 | B |
| 160 | A |

What is claimed is:
1. A compound having the structural formula

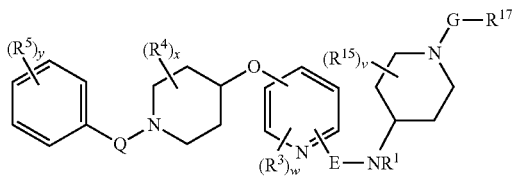

or a pharmaceutically acceptable salt or N-oxide thereof, wherein
the piperidinyloxy group and the -E- group are disposed about the central pyridine in a para or meta relationship to one another;
E is —C(O)— or —S(O)$_2$—;
R$^1$ is H, —(C$_1$-C$_4$ alkyl) or —C(O)O—(C$_1$-C$_4$ alkyl);
each R$^3$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN;
w is 0, 1 or 2;
each R$^4$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^4$ on the same carbon optionally combine to form oxo;
x is 0, 1, 2 or 3;
each R$^5$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN;
y is 0, 1, 2 or 3;
Q and G are each independently a bond, —CH$_2$—, —C(O)—, —CH(CH$_3$)— or —S(O)$_2$—;
v is 0, 1, 2 or 3;
each R$^{15}$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{15}$ on the same carbon optionally combine to form oxo; and
R$^{17}$ is phenyl, pyridyl, pyrimidinyl or imidazolyl, each optionally substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN,
in which
each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^9$)NR$^9$—, —N$^9$SO$_2$—, —SO$_2$NR$^9$— and —NR$^9$SO$_2$NR$^9$—,
each R$^7$, R$^8$ and R$^{10}$ is independently selected from H, —(C$_1$-C$_2$ alkyl), —(C$_1$-C$_2$ haloalkyl), —(C$_0$-C$_2$ alkyl)—L—(C$_0$-C$_2$ alkyl), —(C$_0$-C$_2$ alkyl)-NR$^9$(C$_0$-C$_2$ alkyl), —(C$_0$-C$_2$ alkyl)—O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and
each R$^9$ is independently selected from —H, —(C$_1$-C$_4$ alkyl) and —C(O)O—(C$_1$-C$_4$ alkyl).
2. A compound according to claim 1, wherein R$^1$ is H.
3. A compound according to claim 1, wherein G is —CH$_2$— or —CH(CH$_3$)—.
4. A compound according to claim 1, wherein G is —C(O)— or —S(O)$_2$—.
5. A compound according to claim 1, having the structural formula

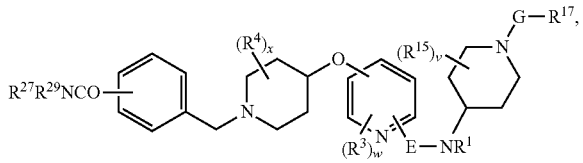

in which R$^{27}$ is selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and R$^{29}$ is —H, —(C$_1$-C$_4$ alkyl) or —CO—O—(C$_1$-C$_4$ alkyl).

6. A compound according to claim 1, having the structural formula

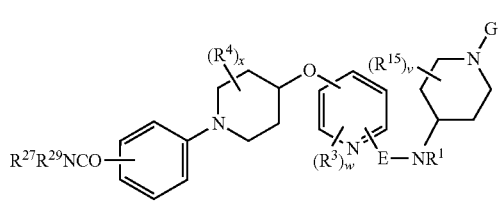

in which $R^{27}$ is selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and $R^{29}$ is —H, —($C_1$-$C_4$ alkyl) or —CO—O—($C_1$-$C_4$ alkyl).

7. A compound according to claim 1, having the structural formula

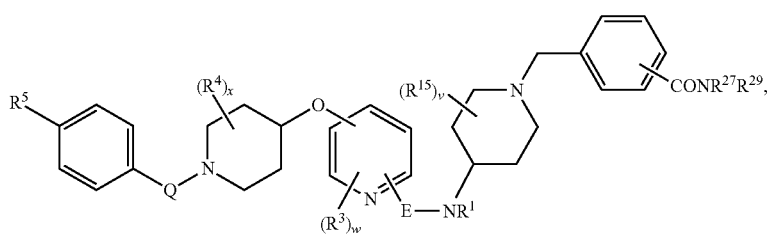

in which $R^{27}$ is selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and $R^{29}$ is —H, —($C_1$-$C_4$ alkyl) or —CO—O—($C_1$-$C_4$ alkyl).

8. A compound according to claim 1, having the structural formula

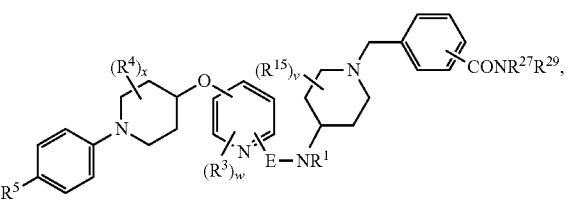

in which $R^{27}$ is selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and $R^{29}$ is —H, —($C_1$-$C_4$ alkyl) or —CO—O—($C_1$-$C_4$ alkyl).

9. A compound according to claim 1, having the structural formula

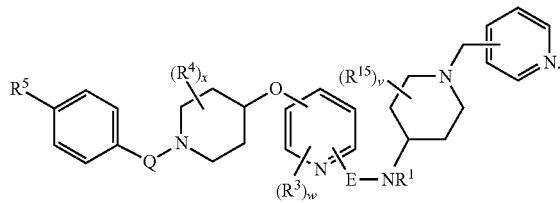

10. A compound according to claim 1, having the structural formula

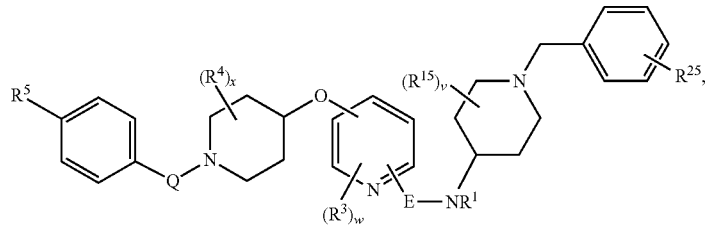

in which $R^{25}$ is selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

11. A compound according to claim 1, having the structural formula

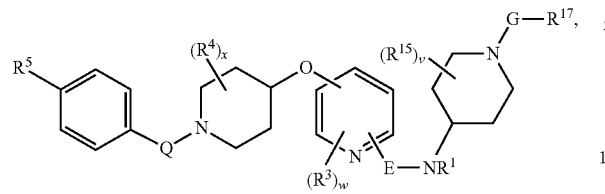

in which Q is —C(O)— or —S(O)₂—.

12. A compound according to claim 1, having the structural formula

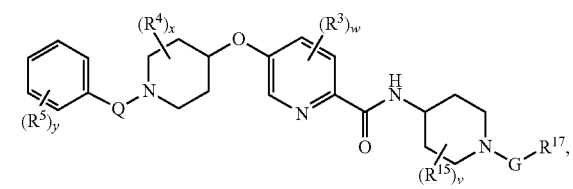

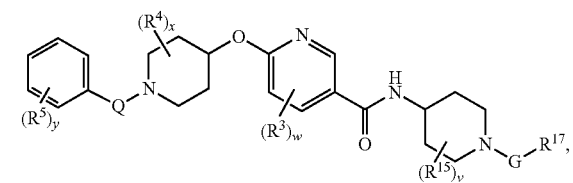

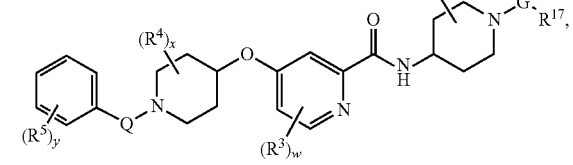

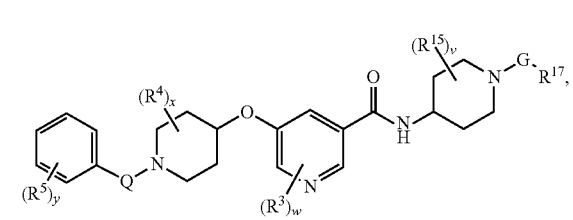

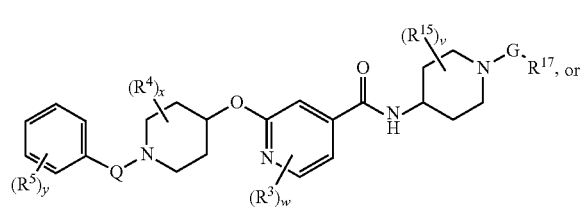

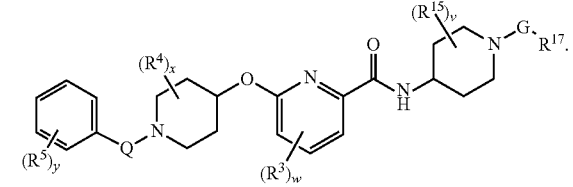

13. A compound according to claim 1, having the structural formula

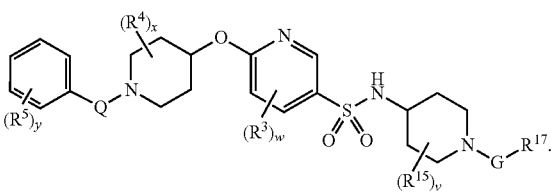

14. The compound according to claim 12, wherein x is 0 and v is 0.

15. The compound according to claim 12, wherein x is 0, v is 0 and w is 0.

16. The compound according to claim 12, wherein x is 0, v is 0, w is 0, and Q is a bond or —CH₂—.

17. The compound according to claim 16; wherein G is —CH₂—.

18. The compound according to claim 1, wherein E is —C(O)—.

19. The compound according to claim 1 wherein $R^{17}$ is pyridyl, or phenyl optionally substituted with 1, 2 or 3 substituents independently selected from —(C₁-C₃ alkyl), —(C₁-C₃ haloalkyl), —(C₀-C₃ alkyl)-L-R⁷, —(C₀-C₃ alkyl)-NR⁸R⁹, —(C₀-C₃ alkyl)-OR¹⁰, —(C₀-C₃ alkyl)-C(O)R¹⁰, —(C₀-C₃ alkyl)-S(O)₀₋₂R¹⁰, -halogen, —NO₂ and —CN.

20. The compound according to claim 12 wherein each R⁷, R⁸ and R¹⁰ is independently selected from H, —(C₁-C₂ alkyl) and —(C₁-C₂ haloalkyl).

21. The compound according to claim 1, having the structure

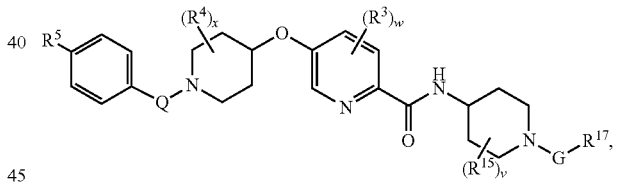

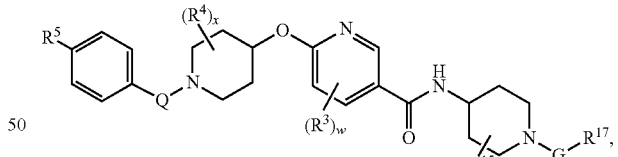

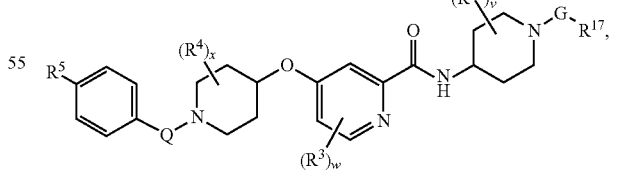

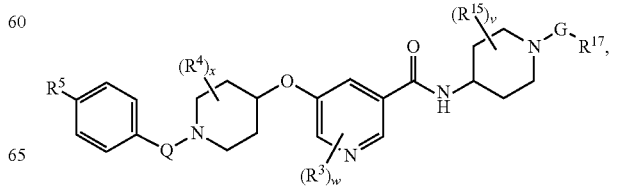

-continued

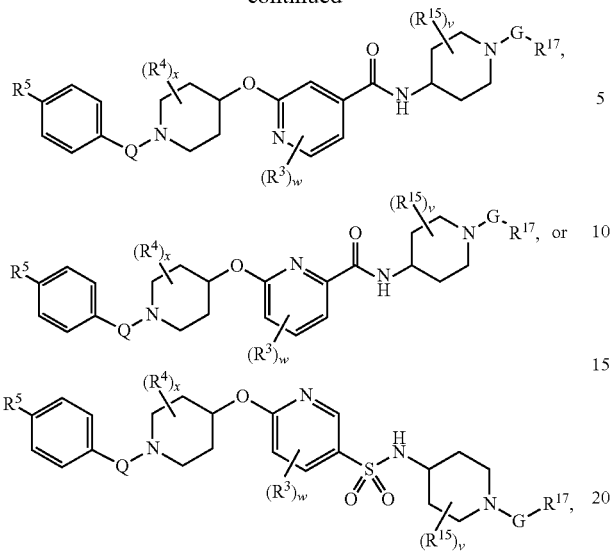

wherein Q is —CH$_2$— or a single bond and R$^{17}$ is selected from

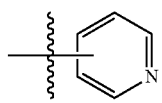

and

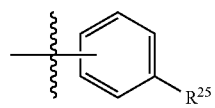

in which R$^{25}$ is selected from halo, cyano, —(C$_1$-C$_3$ haloalkyl), —O—(C$_1$-C$_2$ haloalkyl), —(C$_1$-C$_3$ alkyl), —O—(C$_1$-C$_2$ alkyl), —C(O)—(C$_0$-C$_2$ alkyl), —C(O)O—(C$_0$-C$_2$ alkyl), —C(O)N(C$_0$-C$_2$ alkyl)(C$_0$-C$_4$ alkyl) and NO$_2$.

22. The compound according to claim 21, wherein x is 0, v is 0 and w is 0.

23. The compound according to claim 16; wherein y is 0, or y is not 0 and at least one R$^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$.

24. The compound according to claim 12 wherein each R$^7$, R$^8$ and R$^{10}$ is independently selected from H, —(C$_1$-C$_2$ alkyl) and —(C$_1$-C$_2$ haloalkyl).

25. The compound according to claim 1, wherein y is 0, or y is not 0 and at least one R$^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$.

26. A compound according to claim 1, wherein the compound is
5-(1-(4-cyanophenyl)piperidin-4-yloxy)-N-(1-(pyridin-4-ylmethyl)piperidin-4-yl)picolinamide;
N-(1-(4-cyanobenzyl)piperidin-4-yl)-5-(1-(4-cyanophenyl)piperidin-4-yloxy)picolinamide;
N-(1-(pyridin-4-ylmethyl)piperidin-4-yl)-5-(1-(4-trifluoromethyl)phenyl)piperidin-4-yloxy)picolinamide;
N-(1-(4-cyanobenzyl)piperidin-4-yl)-5-(1-(4-(trifluoromethyl)phenyl)piperidin-4-yloxy)picolinamide;
N-(1-(pyridin-3-ylmethyl)piperidin-4-yl)-5-(1-(4-(trifluoromethyl)phenyl)piperidin-4-yloxy)picolinamide;
N-(1-(pyridin-3-ylmethyl)piperidin-4-yl)-5-(1-(4-cyanophenyl)piperidin-4-yloxy)picolinamide;
methyl 4-((4-(5-(1-(4-cyanophenyl)piperidin-4-yloxy)picolinamido)piperidin-1-yl)methyl)benzoate;
methyl 4-((4-(5-(1-(4-(trifluoromethyl)phenyl)piperidin-4-yloxy)picolinamido)piperidin-1-yl)methyl)benzoate;
N-(1-(pyridin-4-ylmethyl)piperidin-4-yl)-6-(1-(4-(trifluoromethyl)phenyl)piperidin-4-yloxy)nicotinamide;
N-(1-(4-fluorobenzyl)piperidin-4-yl)-6-(1-(4-(trifluoromethyl)phenyl)piperidin-4-yloxy)nicotinamide;
N-(1-(pyridin-4-ylmethyl)piperidin-4-yl)-4-(1-(4-(trifluoromethyl)phenyl)piperidin-4-yloxy)picolinamide;
N-(1-(pyridin-4-ylmethyl)piperidin-4-yl)-5-(1-(4-(trifluoromethyl)phenyl)piperidin-4-yloxy)nicotinamide;
N-(1-(4-fluorobenzyl)piperidin-4-yl)-5-(1-(4-(trifluoromethyl)phenyl)piperidin-4-yloxy)nicotinamide;
N-(1-(4-cyanobenzyl)piperidin-4-yl)-5-(1-(4-(trifluoromethyl)phenyl)piperidin-4-yloxy)nicotinamide;
N-(1-(pyridin-3-ylmethyl)piperidin-4-yl)-5-(1-(4-(trifluoromethyl)phenyl)piperidin-4-yloxy)nicotinamide;
N-(1-(pyridin-4-ylmethyl)piperidin-4-yl)-2-(1-(4-(trifluoromethyl)phenyl)piperidin-4-yloxy)isonicotinamide;
N-(1-(4-cyanobenzyl)piperidin-4-yl)-2-(1-(4-(trifluoromethyl)phenyl)piperidin-4-yloxy)isonicotinamide;
N-(1-(4-fluorobenzyl)piperidin-4-yl)-2-(1-(4-(trifluoromethyl)phenyl)piperidin-4-yloxy)isonicotinamide;
N-(1-(4-cyanobenzyl)piperidin-4-yl)-4-(1-(4-(trifluoromethyl)phenyl)piperidin-4-yloxy)picolinamide;
N-(1-(4-fluorobenzyl)piperidin-4-yl)-4-(1-(4-(trifluoromethyl)phenyl)piperidin-4-yloxy)picolinamide;
N-(1-(4-cyanobenzyl)piperidin-4-yl)-6-(1-(4-(trifluoromethyl)phenyl)piperidin-4-yloxy)nicotinamide;
N-(1-phenethylpiperidin-4-yl)-5-(1-(4-(trifluoromethyl)phenyl)piperidin-4-yloxy)picolinamide;
N-(1-(naphthalen-2-ylmethyl)piperidin-4-yl)-5-(1-(4-(trifluoromethyl)phenyl)piperidin-4-yloxy)picolinamide;
N-(1-benzylpiperidin-4-yl)-5-(1-(4-(trifluoromethyl)phenyl)piperidin-4-yloxy)picolinamide;
N-(1-(4-(dimethylamino)benzyl)piperidin-4-yl)-5-(1-(4-(trifluoromethyl)phenyl)piperidin-4-yloxy)picolinamide;
N-(1-(4-morpholinobenzyl)piperidin-4-yl)-5-(1-(4-(trifluoromethyl)phenyl)piperidin-4-yloxy)picolinamide;
N-(1-(pyridin-4-ylmethyl)piperidin-4-yl)-6-(1-(4-(trifluoromethyl)phenyl)piperidin-4-yloxy)picolinamide;
N-(1-(pyrimidin-5-ylmethyl)piperidin-4-yl)-5-(1-(4-(trifluoromethyl)phenyl)piperidin-4-yloxy)picolinamide;
5-(1-(4-(trifluoromethyl)phenyl)piperidin-4-yloxy)-N-(1-((1-trityl-1H-imidazol-4-yl)methyl)piperidin-4-yl)picolinamide;
N-(1-((1H-imidazol-4-yl)methyl)piperidin-4-yl)-5-(1-(4-(trifluoromethyl)phenyl)piperidin-4-yloxy)picolinamide;
methyl 4-((4-(6-(1-(4-(trifluoromethyl)phenyl)piperidin-4-yloxy)nicotinamido)piperidin-1-yl)methyl)benzoate;
4-((4-(6-(1-(4-(trifluoromethyl)phenyl)piperidin-4-yloxy)nicotinamido)piperidin-1-yl)methyl)benzoic acid;
N-(1-(pyridin-4-ylmethyl)piperidin-4-yl)-6-(1-(4-(trifluoromethyl)phenyl)piperidin-4-yloxy)pyridine-3-sulfonamide;

N-(1-(pyridin-4-ylmethyl)piperidin-4-yl)-6-(1-(4-cyanophenyl)piperidin-4-yloxy)pyridine-3-sulfonamide;

6-(1-(4-cyanobenzyl)piperidin-4-yloxy)-N-(1-(pyridin-4-ylmethyl)piperidin-4-yl)pyridin-3-sulfonamide;

N-(1-(4-cyanobenzyl)piperidin-4-yl)-6-(1-(4-(trifluoromethyl)phenyl)piperidin-4-yloxy)pyridine-3-sulfonamide;

N-(1-(3-cyanobenzyl)piperidin-4-yl)-6-(1-(4-(trifluoromethyl)phenyl)piperidin-4-yloxy)pyridine-3-sulfonamide;

N-(1-(4-(trifluoromethyl)benzyl)piperidin-4-yl)-6-(1-(4-(trifluoromethyl)phenyl)piperidin-4-yloxy)pyridine-3-sulfonamide;

N-(1-(3-(trifluoromethyl)benzyl)piperidin-4-yl)-6-(1-(4-(trifluoromethyl)phenyl)piperidin-4-yloxy)pyridine-3-sulfonamide; or N-(1-(4-fluorobenzoyl)piperidin-4-yl)-6-(1-(4-(trifluoromethyl)phenyl)piperidin-4-yloxy)pyridine-3-sulfonamide.

27. A pharmaceutical composition comprising at least one pharmaceutically acceptable carrier, diluent or excipient; and a compound according to claim 1.

* * * * *